(12) United States Patent
Biesinger et al.

(10) Patent No.: US 10,405,903 B1
(45) Date of Patent: Sep. 10, 2019

(54) FASTENERS WITH SHAPE CHANGING ZIGZAG STRUCTURES AND METHODS USING SAME

(71) Applicant: XTRAVERSE, LLC, Las Vegas, NV (US)

(72) Inventors: David P Biesinger, Las Vegas, NV (US); James A Biesinger, Bethesda, MD (US)

(73) Assignee: Xtraverse, LLC, Las Vegas, NV (US)

( * ) Notice: Subject to any disclaimer, the term of this patent is extended or adjusted under 35 U.S.C. 154(b) by 847 days.

(21) Appl. No.: 14/830,041

(22) Filed: Aug. 19, 2015

Related U.S. Application Data

(63) Continuation-in-part of application No. 13/463,987, filed on May 4, 2012, now Pat. No. 9,138,274.

(51) Int. Cl.
| | | |
|---|---|---|
| *A61B 17/84* | (2006.01) |
| *A61B 17/86* | (2006.01) |
| *A61B 17/68* | (2006.01) |
| *A61B 17/56* | (2006.01) |

(52) U.S. Cl.
CPC .......... *A61B 17/844* (2013.01); *A61B 17/864* (2013.01); *A61B 17/866* (2013.01); *A61B 17/8645* (2013.01); *A61B 17/863* (2013.01); *A61B 17/8685* (2013.01); *A61B 2017/564* (2013.01); *A61B 2017/681* (2013.01); *A61B 2017/8655* (2013.01)

(58) Field of Classification Search
CPC . A61B 17/844; A61B 17/864; A61B 17/8645; A61B 17/866; A61B 17/863; A61B 17/7225; A61B 17/7291; A61B 2017/681; A61B 2017/8655; A61B 2017/564; A61B 17/8685

USPC .................. 606/86 R, 304, 309, 320, 328
See application file for complete search history.

(56) References Cited

U.S. PATENT DOCUMENTS

| | | |
|---|---|---|
| 4,719,917 A | 1/1988 | Barrows et al. |
| 5,246,443 A | 9/1993 | Mai |
| 5,263,973 A | 11/1993 | Cook |
| 5,282,829 A | 2/1994 | Hermes |
| 5,417,692 A | 5/1995 | Goble et al. |
| 5,919,193 A | 7/1999 | Slavitt |

(Continued)

OTHER PUBLICATIONS

Technique Guide dated Jun. 2009 [see pp. 11-15 (Slides 13-17)] found at http://www.synthes.com/MediaBin/International%20DATA/036.000.266.pdf Jun. 1, 2009

*Primary Examiner* — David W Bates
*Assistant Examiner* — Marcela I Shirsat
(74) *Attorney, Agent, or Firm* — Nexsen Pruet, LLC; Townsend M. Belser, Jr.

(57) ABSTRACT

A fastening device having a bellows-like or accordion-like structure made of a material that changes shape when activated by a catalyst, and having pleated or foldable zigzag elements that contract from an extended state to a contracted state upon activation. These elements are formed from zig and zag segments of various shapes. The shape changing material may be a shape memory metal alloy, shape memory polymer or elastic memory composite. A method of using this fastener provides apposition and compression of abutment surfaces to join together two pieces of material, and is suitable for joining apposing bone surfaces together to heal fractures via the use of orthopedic hardware.

17 Claims, 28 Drawing Sheets

(56) References Cited

U.S. PATENT DOCUMENTS

| | | | |
|---|---|---|---|
| 6,059,787 | A | 5/2000 | Allen |
| 7,041,106 | B1 | 5/2006 | Carver et al. |
| 7,819,877 | B2 | 10/2010 | Guzman et al. |
| 7,942,875 | B2 | 5/2011 | Nelson et al. |
| 7,959,652 | B2 | 6/2011 | Zucherman et al. |
| 7,985,231 | B2 | 7/2011 | Sankaran |
| 8,152,775 | B2 | 4/2012 | DeSantis et al. |
| 8,394,097 | B2 | 3/2013 | Peyrot et al. |
| 8,454,653 | B2 | 6/2013 | Hadba et al. |
| 8,475,456 | B2 | 7/2013 | Augoyard et al. |
| 8,556,949 | B2 | 10/2013 | Teisen et al. |
| 8,584,853 | B2 | 11/2013 | Knight et al. |
| 8,834,483 | B2 | 9/2014 | Cheney et al. |
| 9,101,349 | B2 | 8/2015 | Knight et al. |
| 9,138,274 | B1 | 9/2015 | Biesinger et al. |
| 9,161,789 | B2 | 10/2015 | Peyrot et al. |
| D745,163 | S | 12/2015 | Cheney et al. |
| 9,204,932 | B2 | 12/2015 | Knight et al. |
| 9,907,585 | B2 * | 3/2018 | Fox ................. A61B 17/7225 |
| 2002/0165544 | A1 | 11/2002 | Perren et al. |
| 2003/0139746 | A1 | 7/2003 | Groiso |
| 2004/0133204 | A1 | 7/2004 | Davis |
| 2004/0230193 | A1 * | 11/2004 | Cheung ............ A61B 17/7266 606/63 |
| 2008/0015598 | A1 | 1/2008 | Prommersberger |
| 2008/0065153 | A1 * | 3/2008 | Allard ................. A61B 17/064 606/219 |
| 2008/0177262 | A1 | 7/2008 | Augoyard et al. |
| 2009/0062799 | A1 | 3/2009 | Holsten et al. |
| 2009/0182336 | A1 | 7/2009 | Brenzel et al. |
| 2009/0210016 | A1 * | 8/2009 | Champagne ........ A61B 17/863 606/309 |
| 2009/0228048 | A1 | 9/2009 | Duncan et al. |
| 2010/0036430 | A1 * | 2/2010 | Hartdegen ........ A61B 17/1728 606/281 |
| 2010/0070043 | A1 | 3/2010 | Kitchen |
| 2010/0125275 | A1 | 5/2010 | Kinmon et al. |
| 2010/0131014 | A1 | 5/2010 | Peyrot et al. |
| 2010/0241165 | A1 * | 9/2010 | Konieczynski .... A61B 17/7071 606/248 |
| 2011/0004255 | A1 | 1/2011 | Weiner et al. |
| 2011/0054545 | A1 | 3/2011 | Champagne et al. |
| 2011/0082508 | A1 | 4/2011 | Reed |
| 2011/0144645 | A1 | 6/2011 | Saravia et al. |
| 2011/0295255 | A1 * | 12/2011 | Roberts ................ A61B 17/744 606/64 |
| 2015/0201979 | A1 | 7/2015 | Paul |
| 2016/0317198 | A1 | 11/2016 | Fox |

\* cited by examiner

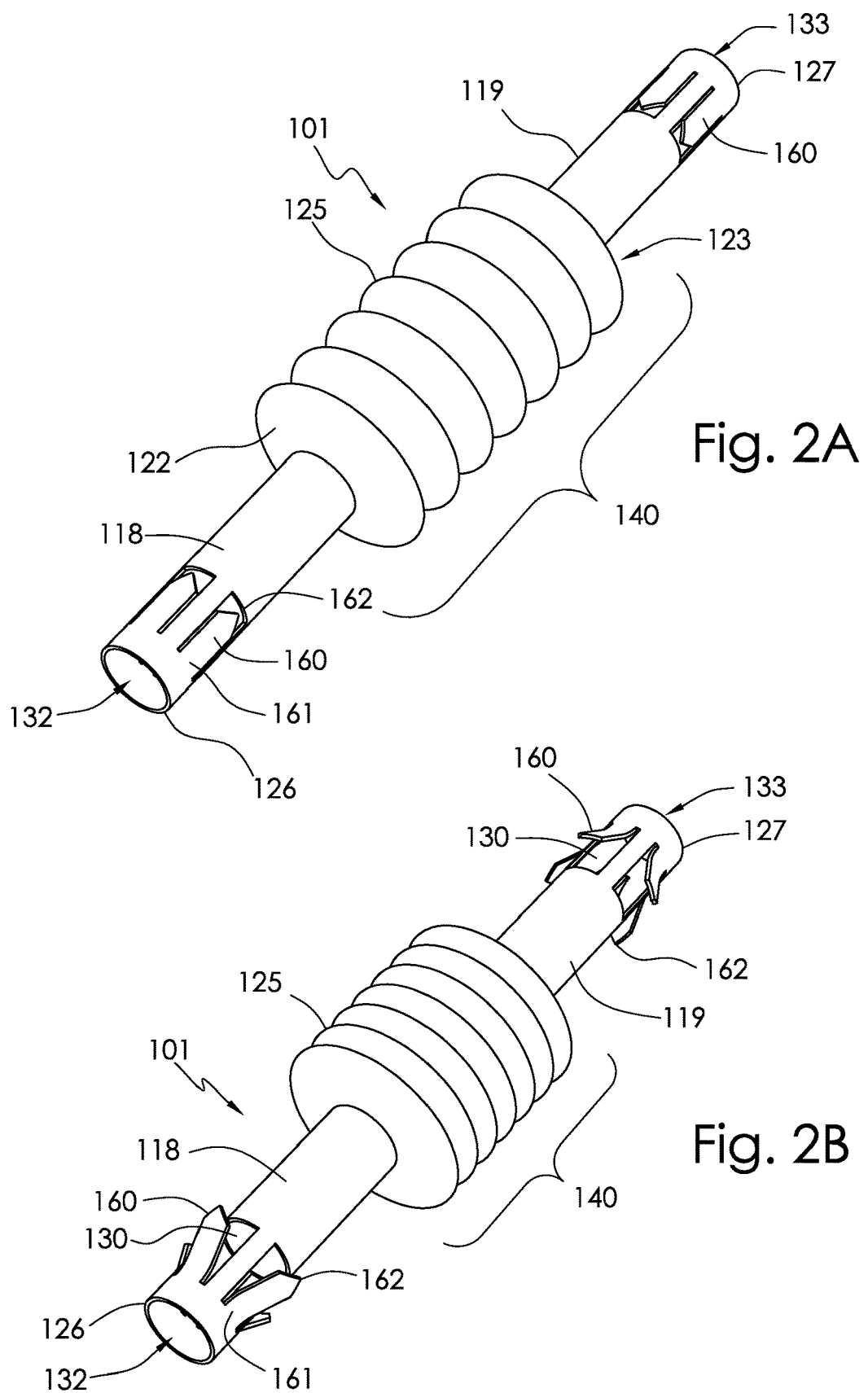

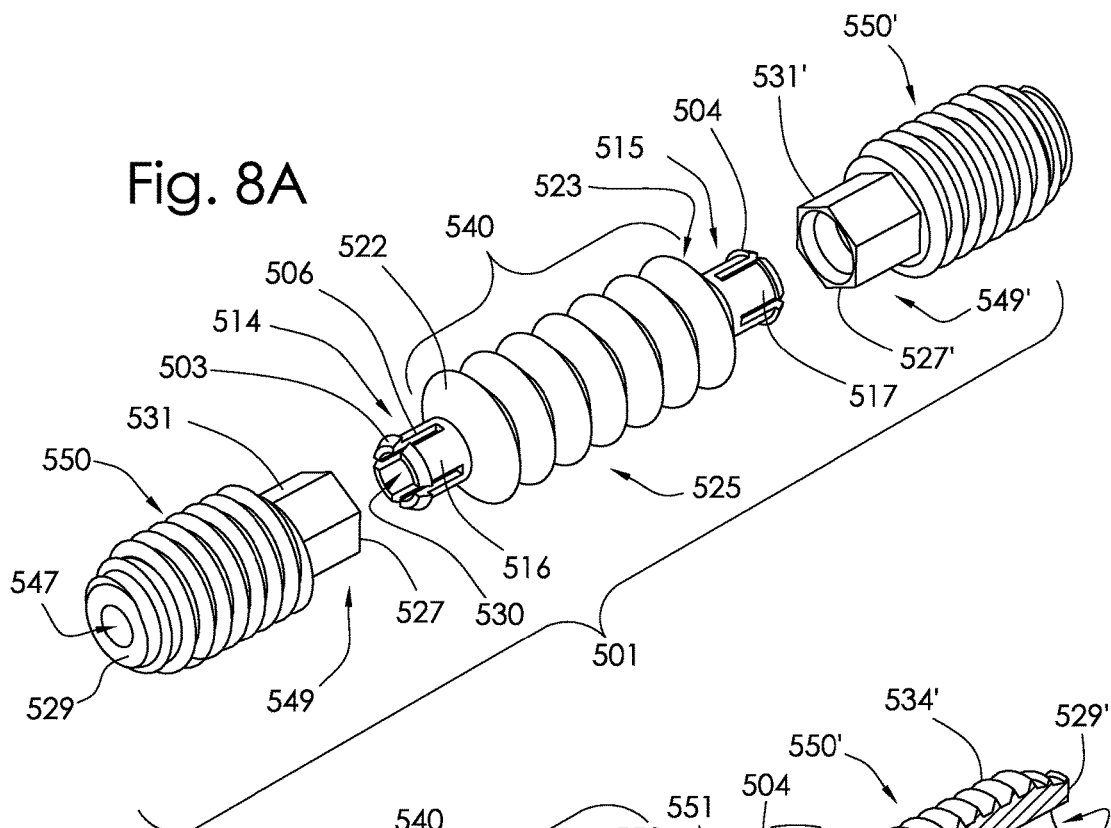
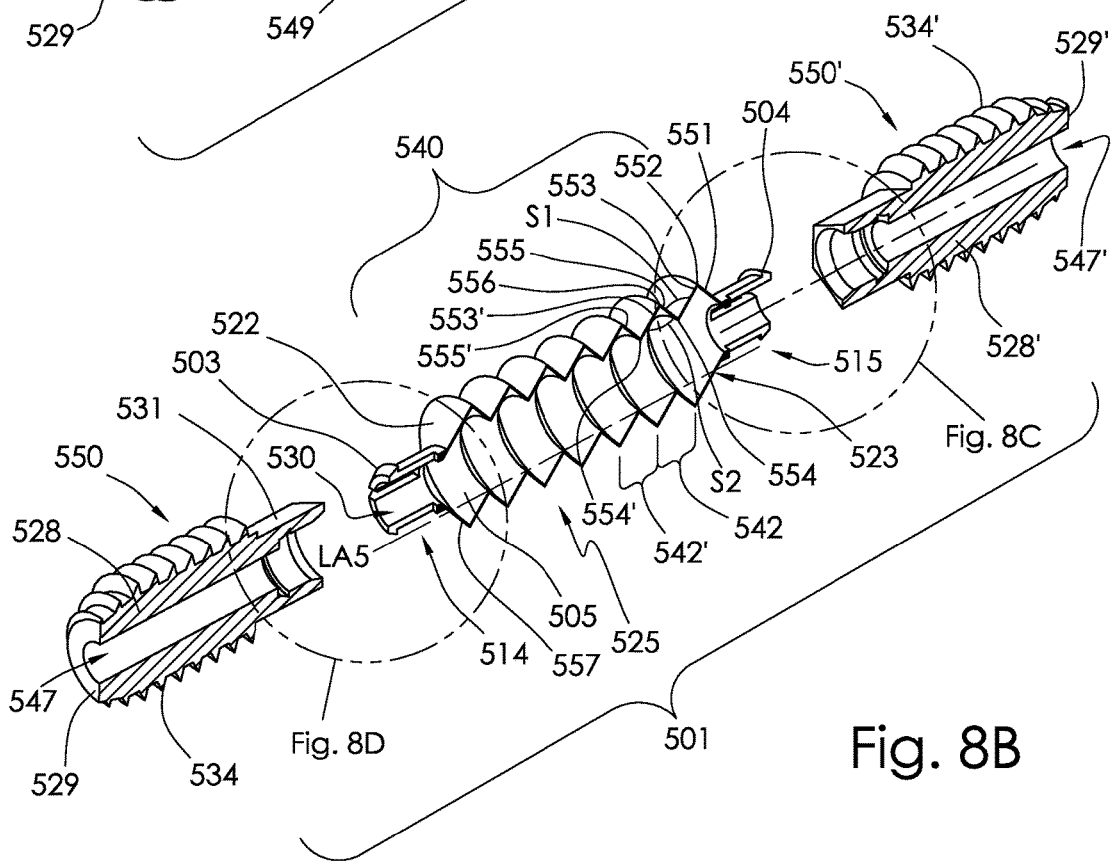

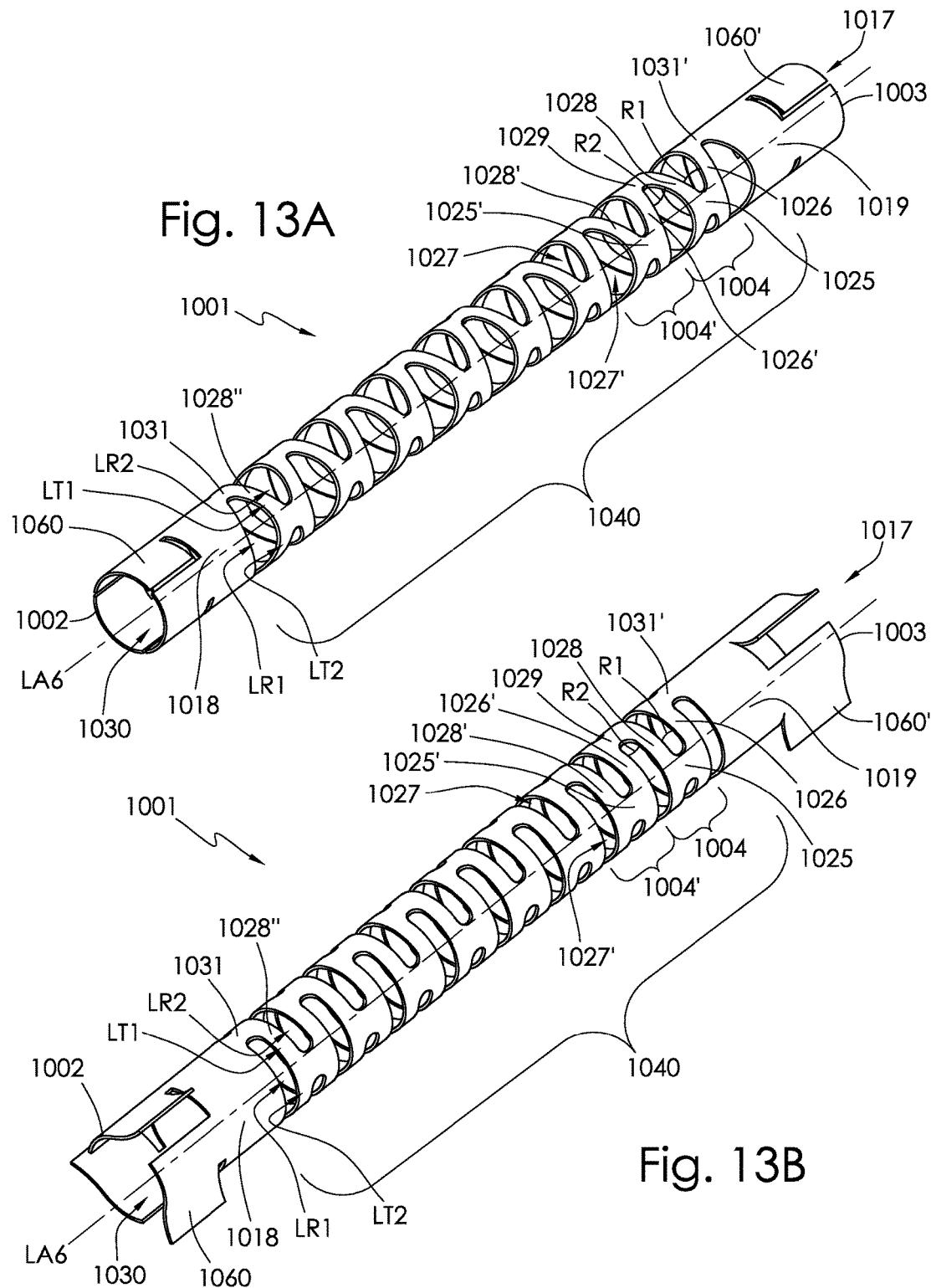

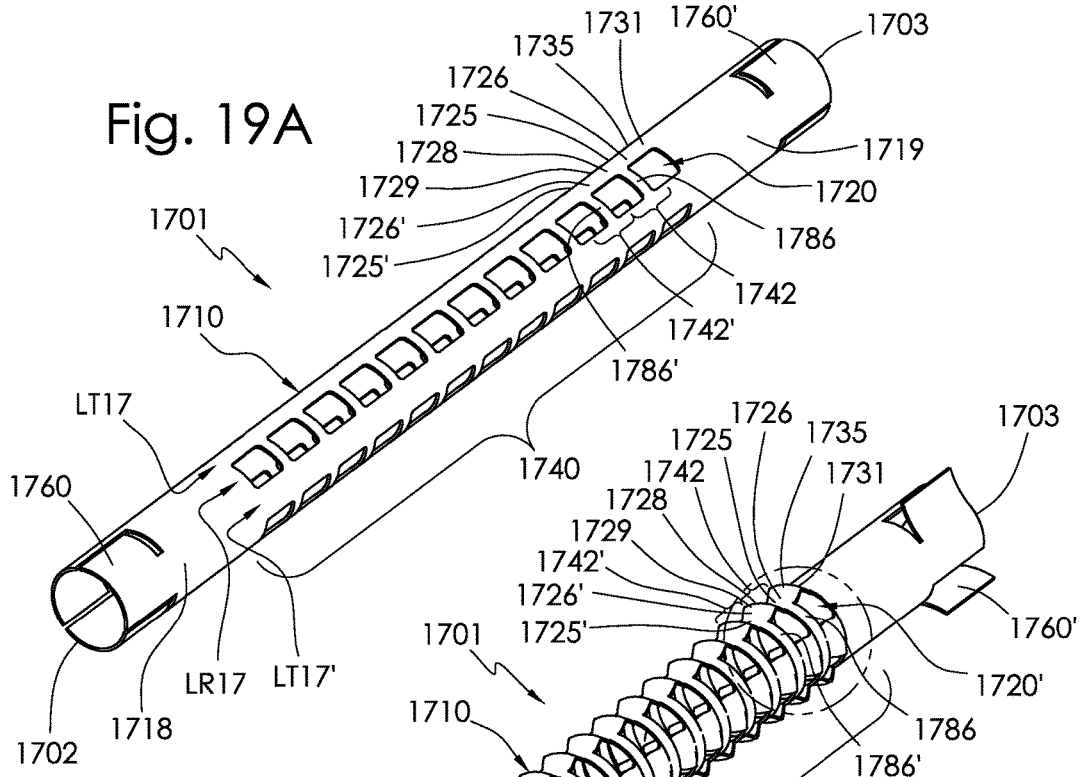
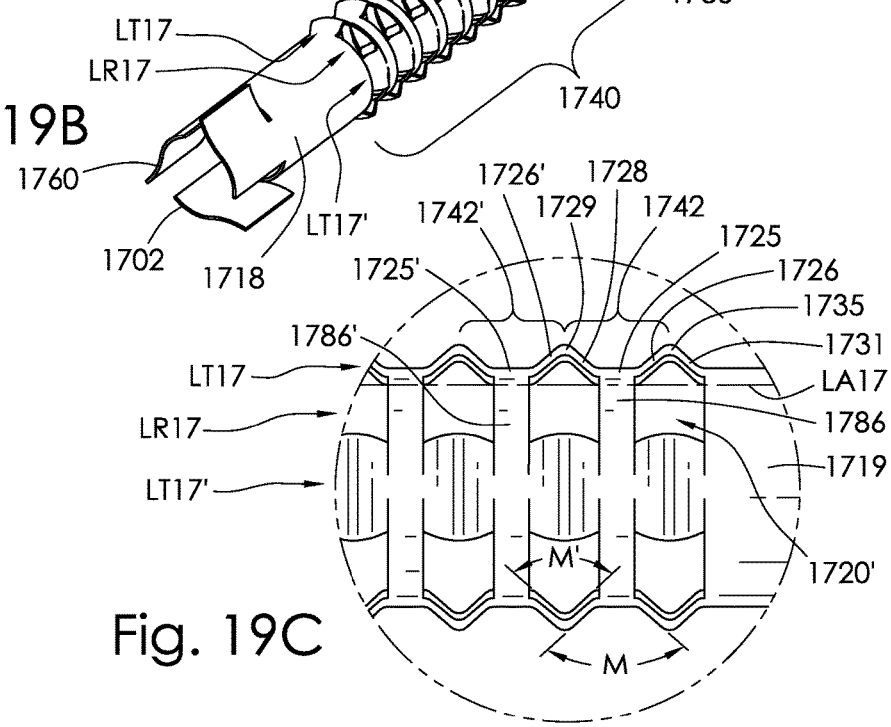
Fig. 19A
Fig. 19B
Fig. 19C

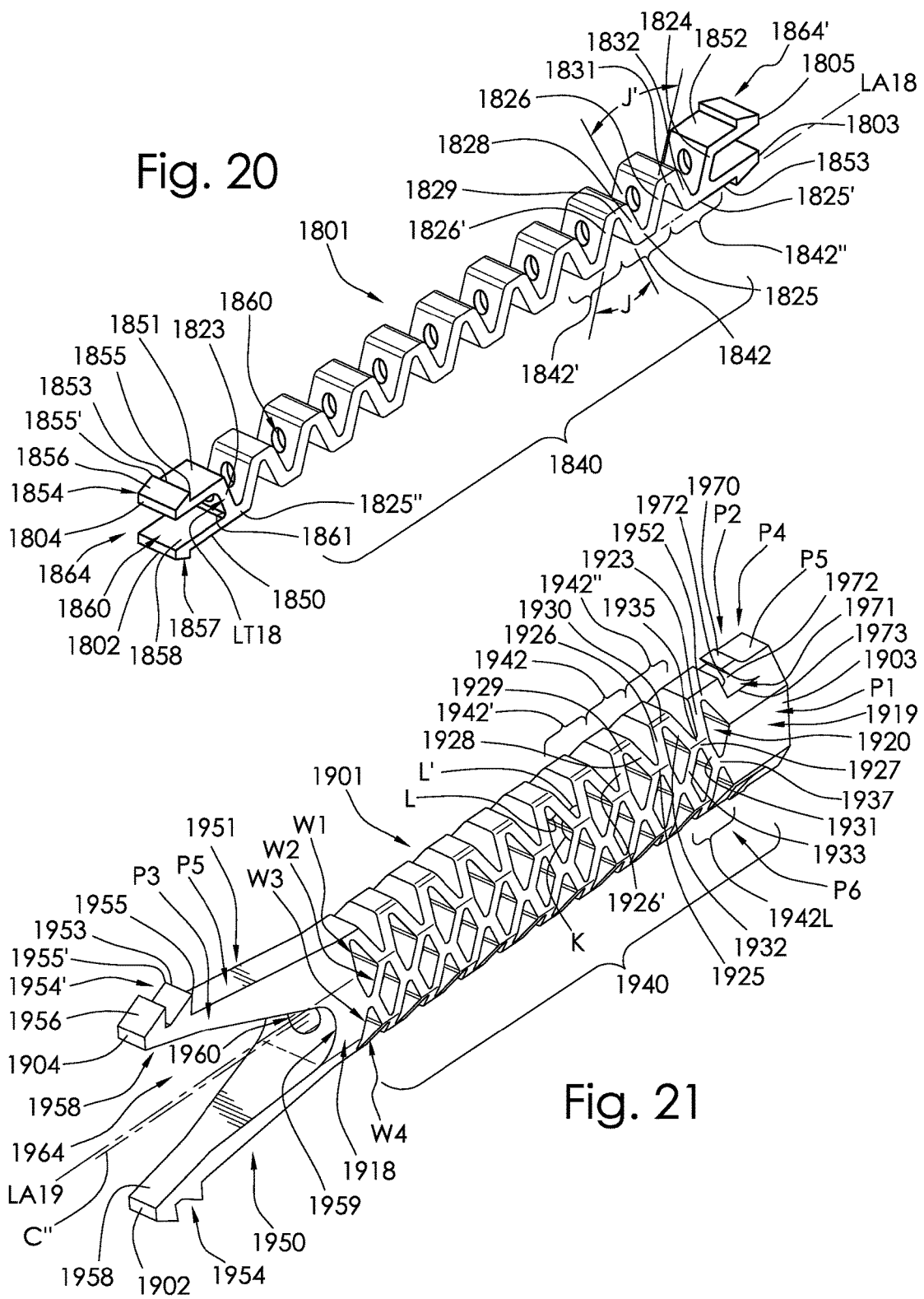

FASTENERS WITH SHAPE CHANGING ZIGZAG STRUCTURES AND METHODS USING SAME

RELATED APPLICATIONS

This is a continuation-in-part of pending U.S. patent application Ser. No. 13/463,987 filed May 4, 2012, for "Fasteners with Shape Changing Bellows and Methods Using Same", which has been allowed and to which the benefit of priority is claimed.

TECHNICAL FIELD

The present invention relates generally to joining and compressing together the surfaces of two or more pieces or parts by utilizing a contractible bellows-like or accordion-like structure having a contractible accordion portion or section made entirely or partially of a shape memory material. Anchoring members are fixedly attached to opposite ends of the contractible structure and are fixedly attachable to the respective pieces or parts to be joined together.

These could be two or more pieces of wood, plastic, metal, bone, or combinations thereof, though not limited to any of these in particular. More specifically, the present invention has an application in the joining of two bone surfaces together for the purposes of osteosynthesis, or of bone fusion, and it relates particularly to a new and improved orthopedic endoprosthesis for fusing the bones together in a toe or finger. As used in this specification, "fixedly attached" and "integral" mean that the two elements being referred to are connected for translational movement together as a unit in a predetermined direction.

BACKGROUND OF THE INVENTION

The medical term for a toe or finger is a phalange and any individual bone within a toe or finger is called a phalanx. Deformities of the phalanges are common conditions encountered by surgeons. These deformities can occur for numerous reasons and the deformities have acquired different names such as mallet toe, claw toe, hammertoe, boutonniere deformity, and swan neck deformity, amongst others. Surgeons often address these deformities surgically in an attempt to straighten the phalanges, to alleviate pain, provide stability to the digit, improve ambulation, gait, or dexterity, or prevent further sequelae of phalangeal deformities.

The fixation of bone fractures or surgically manipulated bones with orthopedic hardware such as screws, plates, pins, and staples helps bone to heal. Bone fixation was originally accomplished with externally applied casts or other forms of immobilization which led to high rates of nonunion or malunion as these forms of immobilization afforded little inherent stability at the bone-bone interface. Stability is a critical factor for obtaining consolidation or bone healing. Eventually metallic rods and pins were utilized to increase stability of bone fixation thereby improving healing rates. Eventually further stability was gained through the use of screws across bone and joint surfaces because they added a compressive force across the opposing bone surfaces. Further improvements were made to screws via cannulation which allowed the more rapid placement of the screws, more accuracy, and greater ease of use whether for the repair of fractures or fusing the bones of a joint.

Of particular interest is the fusion of the proximal interphalangeal joint (PIPJ) of the toes and fingers for stabilizing and correcting deformity of these structures. The procedure normally involves resecting or cutting away the joint surfaces of the PIPJ. The two phalanx bones are then placed end to end and a rod or pin is then driven axially along the internal diameter of the phalange providing stability for osteosynthesis. One end of the pin typically remains outside of the skin of the phalange at the tip of the toe or finger during the healing process.

There is concern for many surgeons about the use of pins with this type of surgery because an exposed pin at the distal toe tip may increase the risk of pin tract infections. There is also the possibility of undesired migration of the pins deeper into a bone or the accidental removal of the pin prior to healing of the bone ends. Placing the pin through the skin like this also introduces the pin across the distal interphalangeal joint (DIPJ) and thus violates that joint. Also, the use of pins provides no rotational stability and may allow the phalangeal bones to "piston" on the pin because it is smooth. Therefore some surgeons look toward devices that can be introduced across the PIPJ alone so they do not stick out through the skin, do not violate the DIPJ or the metatarsal phalangeal joint (MTPJ), do not increase the risk for infection, and will provide stability in all planes. However, though there is some legitimacy to these concerns, the use of pins is often necessary when performing toe or finger surgery.

There are times when the surgery for reduction of a toe or finger deformity requires more than just a joint fusion of the PIPJ for proper correction. The release of ligaments and the transfer of tendons are sometimes necessary more proximally at the MTPJ adjacent to the PIPJ or at the DIPJ. This is done at the surgeon's discretion as he or she sees fit and may thus require the use of a pin across one or both of these joints to provide fixation and stability. The DIPJ and MTPJ are rarely fused. Surgeons currently have the option to use a pin and accept its disadvantages, or use some other commercially available product without the use of a pin, each of these having their own disadvantages.

DESCRIPTION OF THE RELATED ART

One particular prior art device allows the placement of an internal fixation device into a PIPJ that does not violate the adjacent MTPJ or DIPJ. The device is comprised of two members that screw into the bone surfaces and are then joined together. One drawback of the device design is that it does not allow the simultaneous use of a pin in a toe in order to stabilize an MTPJ or a DIPJ. Nor does it provide compression across the joint fusion site which would allow for increased stability and thus improve healing. The device affords no rotational stability. Lastly, during clinical application, the device has been known to separate after implantation due to the patient accidently traumatizing the surgical site. Each of these problems is avoided with the use of the shape memory zigzag fastener of the present invention.

Another prior art device is a bioabsorbable pin that is placed through the skin through the toe tip across the distal, middle and proximal phalanx of the digit. Like standard pins, they provide no rotational stability to the fusion site and no compression of the fusion site and are thus undesirable.

Other prior art intramedullary osteosynthesis devices are made of a material suitable for deformation by thermal or mechanical action. These devices provide increased stability over the above devices by providing compression at the osteosynthesis sites and may afford some rotational stability although their ability to do so effectively is limited. The dependability of these devices to maintain a strong bite or hold, or maintain alignment on the bones they are implanted into, while at the same time providing compression, has not been satisfactory due to design flaws. These devices also fail to provide the surgeon the option of placing percutaneous wires axially through bones of the phalanx and across the DIPJ and MTPJ when necessary. Furthermore, these devices are difficult to implant into bone due to size and tooling restrictions.

Still other devices are too complex to use or have multiple small parts making them impractical to use in a surgical setting. One such device is made up of two parts that screw into bone first and then screw into each other. However, this is not practicable because the bones of the phalange cannot rotate due to their ligament, tendon, and other soft tissue attachments. Another such device is hinged and allows a rectus or angular placement so the bones of the phalange can be fused straight or at an angle other than 180 degrees. However, multiple small parts make its use impractical and cumbersome.

None of the known prior devices used for the fixation or fusion of interphalangeal joints of the hands or feet are considered sufficient for surgical correction of deformed toes or fingers. The deficiencies include: not providing compression across the fusion site, not anchoring or holding well in bone to provide a firm grasp of the bone such that the device may be easily dislodged after implantation, not cannulated to allow for pinning of the DIPJ or MTPJ when this is necessary, causing nearly complete destruction of the adjacent DIPJ or MTPJ in order to implant the device, requiring very specialized tools for its application such that the implant is not useable without these tools, and/or having very small parts which make the device difficult to use in a clinical setting. These faults result in unwanted sequelae of the intended surgery.

SUMMARY OF THE INVENTION

In accordance with the invention, a shape changing fastener comprises an elongated body having a bellows-like or accordion-like portion or section. This accordion-like section comprises a material that changes shape when activated by a catalyst and has a structure that contracts axially from an extended state to a contracted state when the shape changing material is deformed to provide the extended state and is thereafter activated by the catalyst to provide the contracted state, such that the accordion section is shortened to move a first attached anchoring means toward a second attached anchoring means. The accordion-like section has at least one zigzag element comprising a zig segment and a zag segment joined together by a bendable connection (connector) that allows this element to expand and contract. As this element is expanded by deformation, the zig and zag segments converge toward the connector at an acute angle, the size of which increases as the force producing the deformation increases. There are preferably a plurality of sequential zigzag elements wherein each element is connected to the next element by a bendable interconnection (interconnector). In addition, the wall thickness of one or both of the zig and zag segments preferably is sufficiently thin for these segments to also be bendable by deformation.

The fastener is made entirely or partially of the shape memory material and the accordion portion extends along the central aspect of its body for providing compression across two joinable surfaces. The anchoring means of the fastener may comprise tubular sleeves or other shaped members extending from both ends of the accordion-like portion, each of these two members having barbs or other anchoring modality to allow the fastener to grab or bite into the bone or other material of the pieces to be joined. Although the barbed portion is made from the same or a similar shape memory material, the remainder of the sleeves or other anchoring members may be made from other materials.

Shape memory metal alloys, such as nitinol, a nickel titanium alloy, have two closely related and unique properties: shape memory and superelasticity. Shape memory is the ability of nitinol to undergo deformation at one temperature, then recover its original undeformed shape upon heating above its transformation temperature. Superelasticity occurs at a narrow temperature range just above its transformation temperature wherein no heating is required to cause the undeformed shape to recover. The material can exhibit enormous elasticity, some 10-30 times that of ordinary metal, and these properties make it particularly useful for the invention. The accordion-like portion of the embodiment, as well as the anchoring barbs, goes through a shape change allowing the embodiment to perform its function. The barbs change shape to anchor the fastener in the bone while the accordion-like portion changes shape by contracting, in an accordion-like fashion, to pull together and compress opposing faces of the PIPJ.

Many shape memory materials exist. Shape memory metal alloys are probably the most well-known and useful. Nitinol is a medical grade biocompatible memory metal alloy made of nickel and titanium currently used in many industrial and medical applications. There are other shape memory metal alloys available. These include but are not limited to alloys composed of iron, nickel, and manganese or iron, manganese, and silicon, some of which are not biocompatible and therefore not for use in human or animal subjects. Many others exist. The shape memory metal alloys have two primary phases, an austenite phase and a martensite phase. Shape memory metal products are originally manufactured in the austenite phase and annealed to relieve residual manufacturing stresses. The metal may then be cooled sufficiently whereupon it transforms to its highly plastic martensite phase. This phase facilitates manipulation into a new shape by large strain plastic deformation at a low applied stress. The new shape is stable as long as the alloy remains below the phase transition temperature. Above the austenite finish temperature (Af), the parent material is called austenite and has a cubic structure. Upon cooling below the martensite start temperature (Ms), the crystal structure changes to a low-symmetry, monoclinic martensite structure; this martensitic transformation is reversible upon heating. Below the martensite finish temperature (Mf), the alloy is completely martensitic and is termed as thermally-induced martensite (TIM). When the thermally-induced martensite is deformed by an external stress, the shape of the alloy changes to accommodate the loading strains. However, upon heating above the austenite finish temperature, Af, the alloy 'remembers' its original austenite phase structure and the reverse transformation occurs; thus the material exhibits the shape memory effect. By contrast, when the austenite phase is deformed by external stress within the temperature range Af<T<Md, the austenite undergoes a stress-induced martensite (SIM) transformation, Md being the temperature above which austenite will not transition to martensite when stress is applied. Upon removal of the load, however, the martensite structure reverts back to the austenite phase, since austenite is the more stable phase within this temperature 'window'. This is termed as superelasticity if the specimen recovers all of the loading strains; partial unloading is termed pseudoelasticity.

The two unique properties described above are made possible through a solid state phase change, that is, a molecular rearrangement, which occurs in the shape memory alloy. Typically when one thinks of a phase change a solid to liquid or liquid to gas change is the first idea that comes to mind. A solid state phase change is similar in that a molecular rearrangement is occurring, but the molecules remain closely packed so that the substance remains a solid.

Raising the temperature of the martensite phase metal to its transition temperature causes the metal to transform back to its austenite phase, called austenitic transformation, and thus back to its original shape. Martensite is the lower temperature phase and austenite is the higher temperature phase. Austenite is also known as the parent phase, martensite is the daughter phase. Heat induces the shape change. The austenite phase is stable as long as the material is maintained above its transition temperature. Cooling the austenite phase back to its martensite phase after it has been heated, however, does not cause the material to revert back to the previously deformed shape; a deforming force being required.

A step in the manufacture of the fastener may require an intermediate process whereby elements of the fastener are shape-set such that these elements assume a preferred position when in the austenite phase. Elements that may be shape-set are the barbs or even the zig and zag segments. To shape-set an element, the element, or barbs in this instance, are deformed into their open, or austenite, orientation and fixedly constrained. The fastener is then heat treated at a very high temperature for a predetermined amount of time. Upon cooling of the fastener and subsequent release of the constraining fixture, the elements will remain in their constrained orientation. This orientation being the new austenite phase orientation. Shape-setting may also be used to change the contracted length of the zig-zag segments The preferred embodiments of the shape memory fastener are originally manufactured in their austenite or parent phase. The expandable and then contractible accordion-like portion of the fastener comprises a series of folds formed by various arrangements of zig and zag segments joined at an acute angle by a bendable connector or interconnector that lets the accordion-like portion expand as the acute angle is increased by deformation in the martensite phase. The zig and zag segments in their austenite or parent phase may also be arranged in parallel when joined by a bendable connector or interconnector and then bent apart during the beginning of the deformation to form an acute angle. The acute angle of the bendable connector or interconnector thereafter decreases when returning to the austenite phase in response to a predetermined temperature increase. When the accordion-like portion is in its shortened or contracted position (the austenite phase or contracted state), the barbs on the ends of the fastener are displaced radially outward. The fastener is then cooled to its martensite phase and a force is applied to the anchoring barbs forcing them to lie flush or very nearly so, with the surface of the anchoring member to which they are attached. Also a force is applied to the bellows-like or accordion-like portion to stretch and elongate the fastener body into an extended position (extended state) through the process of atomic rearrangement.

As long as the fastener remains below its transition temperature or is mechanically held in this position with an external jig/device, the new shape of the fastener is maintained. The retained memory of the metal fastener allows the deformed device, upon an increase in temperature, to return to its austenite phase again through atomic rearrangement. When this happens, the barbs deploy radially outward to embed themselves into the surrounding substrate and the accordion like portion shortens in an axial fashion, causing the barbs to pull upon the substrate. The return to the original shortened length of the contractible accordion-portion pulls together any surfaces intended to be compressed together. Thus, the fastener in its martensite, daughter, or extended phase may be referred to as a heat responsive fastener that is activated or catalyzed by heat to undergo the transformation from its extended state to its austenite, parent, or contracted phase. Likewise, the fastener can be engineered to expand, rather than contract, as it transitions from martensite to austenite.

Aside from metal alloys there are other shape changing materials, including plastics. Plastics with these characteristics are often referred to as shape memory polymers, elastic memory composites or shape memory composites, and polymeric smart materials. These polymers have different states similar to the phases of the shape memory metal alloys, and these states are generally referred to as a soft phase or a hard phase. These states are also known as a rubbery state or a glassy state, respectively. The glass transition is the reversible transition from a hard phase (extended state) to a soft phase (contracted state) and is responsible for the shape memory effect of the polymer. These materials also need a catalyst for shape changing which may include heat, electricity, electromagnetic fields, light, or chemical solutions.

The hard or glassy state is the resting state of a shape memory polymer. A product made from shape memory polymer is originally manufactured in the glassy state by conventional methods. The shape memory product is then transformed into its soft or rubbery state by heating or some other process. Once in the rubbery state it is manipulated and deformed into a new shape and held constrained in this new shape. The shape memory polymer product is then cooled wherein it then returns to a glassy state. When the constraining forces are then removed, the polymer maintains this newly shaped glassy state. The product is then ready for use based on a utility for which it has been designed or created. For instance, the shape memory polymer product may be implanted into a body wherein body heat or some other process has an effect on the newly shaped glassy product causing it to return back to its rubbery state. This last transition from the glassy state to the rubbery state also causes the product to change back to its original shape. These changes in shapes can be used to do work or cause an effect on the tissues surrounding it.

Some of the shape memory polymers have the ability to take on two, three, and maybe even four shapes and they can have a wide range of properties, from stable to biodegradable or elastic to rigid. Polymers that show shape memory effects include polyurethane, polyethylene oxide, and polyethylene terephthalate, among others. For example, poly(ε-caprolactone) dimethacrylate and n-butyl acrylate are biodegradable and can be made to change shape through the use of heat from a laser. Fasteners according to the invention made with these shape memory polymers could be used in some applications.

Some embodiments of the fastener provide angularity between the anchoring members, and still other embodiments demonstrate that the anchoring members do not need to be made of shape memory material entirely but may instead be of standard surgical materials and joined by an accordion-like or bellows-like structure of shape memory material. Some portions of an embodiment may also be fabricated to have superelastic properties not requiring heat to affect a change in structure. One or more aspects of the invention are as follows: to allow compression across an object's surfaces, to prevent slipping or accidental displacement of the implant, to intrinsically afford rotational and torsional stability, and to prevent destruction of adjacent joints. Several embodiments provide a cannulation for accurate placement, rapid placement, and the option of maintaining a pin across adjacent surgical sites if needed. Other aspects will be apparent from review and consideration of the drawings and the detailed description below. Also, most of the tools required for the placement of the fastener are readily available in most operating rooms, negating the need for large amounts of specialized tooling.

The problems these embodiments resolve as pertains to osteosynthesis include: providing reliable compression across a fusion or osteosynthesis site, preventing unwanted distraction of an osteosynthesis site, provide rotational stability, preventing the destruction of adjacent joints, and allowing the option for a wire to remain in the surgical site and adjacent surgical sites at the same time as the invention if the surgeon so desires.

BRIEF DESCRIPTION OF THE DRAWINGS

The invention may be further understood with reference to the accompanying drawings, which are briefly described as follows:

FIG. 2A is a profile perspective view of a first embodiment of a fastener according to the invention as shown in its martensitic phase. The fastener is in its elongated stressed phase where the central accordion section in the form of a closed bellows is stretched and barbs at the ends of the fastener lie flush with the walls of sleeves integral with and extending outward from the bellows.

FIG. 2B is a profile perspective view of the first embodiment of the fastener which has gone through a shape change from the martensitic phase of FIG. 2A to its axially shortened austenitic phase. This is the resting shape of the fastener and also the shape of the fastener after implantation into a toe or bone or other substrate. Here the closed bellows section has shortened axially and the barbs have deployed outward from the long axis of the fastener.

FIG. 8A is an exploded profile perspective view of a fifth embodiment of the fastener in its martensitic phase and having three separate component parts. There is a central closed bellows or accordion-like section for undergoing a shape change and which is attachable to two identical screws that can be implanted into bones prior to coupling the bellows portion to these screws. One screw is designated to attach to one side of the bellows section while the second screw attaches to the opposite side of the bellows section.

FIG. 8B is an exploded profile perspective cut-away view of FIG. 8A showing the inside of the fastener of FIG. 8A.

FIG. 13A is a profile perspective view of a ninth embodiment in its deformed martensite phase and showing a single piece construct wherein the fastener has an accordion section with an "open" structure. Instead of pleats or folds extending outward radially from a central axis, the "open" pleats or folds of the accordion section are formed by cutting pairs of opposing transversely oriented slots transversely through the wall of a tubular fastener body in alternating directions preferably ninety degrees apart along the length of the accordion section.

FIG. 13B is a profile perspective view of the "open" accordion-like structure of FIG. 13A showing the fastener in its contracted, shortened austenite phase with the barbs of the integral sleeves deployed outward for anchoring into the pieces to be joined, such as bone segments.

FIG. 19A is a profile perspective view of a sixteenth embodiment showing a single piece construct wherein the accordion structure is in its deformed stretched martensite phase and the barbs of the fastener lie flush by deformation to the outer surface of the fastener. The accordion portion is made up of a plurality of longitudinally aligned rows of square openings cut transversely through the wall of a tubular fastener body and beset side by side in parallel around the circumference of the fastener body.

FIG. 19B is a profile perspective view of the embodiment shown in FIG. 19A in the contracted shortened austenite phase. The accordion section in this embodiment assumes an "open" bellows-like shape when changed from the martensite phase to the austenite phase wherein, during this phase change, the pleated arrangement of the bellows-like folds extends outward in a radially corrugated fashion from the central axis of the fastener body.

FIG. 19C is an enlarged profile perspective view of a central portion of the embodiment shown in FIG. 19B detailing the zigzag segmentation of the open bellows-like portion of the fastener in its austenite phase.

FIG. 20 is a profile perspective view of a seventeenth embodiment showing a different central accordion section in the contracted shortened austenite phase. The central accordion section of the fastener is again made up of a series of zigzag structures forming a longitudinal extending zigzag or corrugated wall with a central cannulation. As viewed from one end, each zigzag structure comprises a zig segment slanted longitudinally and radially inward and integrally connected by an inner connector to a zag segment slanted longitudinally and radially outward relative to a lower longitudinal axis, such that these two segments together form a V-shaped zigzag element that is integrally connected by an outer interconnector to an adjacent V-shaped zigzag element. At each end of this accordion section, the embodiment has integrally connected anchoring members for attaching to bone or other substrates.

FIG. 21 is a profile perspective view of an eighteenth embodiment showing a single piece construct in its austenite phase wherein the shape of the fastener body has an octagonal cross-section such that it is longitudinally octagonal instead of longitudinally cylindrical. This alternative accordion structure is made up of a stack of four longitudinal extending zigzag or corrugated walls, each similar in construction to the embodiment of FIG. 20 but with intermediate lower and upper junctures integrally connected to each other. Upper and lower walls abutting two intermediate walls of the stack form a plurality of X's providing diamond shaped transverse openings in the accordion structure which afford it an open accordion-style shape similar to an elevator gate. The accordion section formed by the X's is not arranged circumferentially around the body of the fastener, but instead the X's are full thickness from one octagonal side to an opposite octagonal side. A central cannulation passes longitudinally through the octagonal fastener body. This embodiment shows at opposite ends alternative means for anchoring the fastener into a surrounding substrate.

DETAILED DESCRIPTION OF THE INVENTION

Figure 1A:
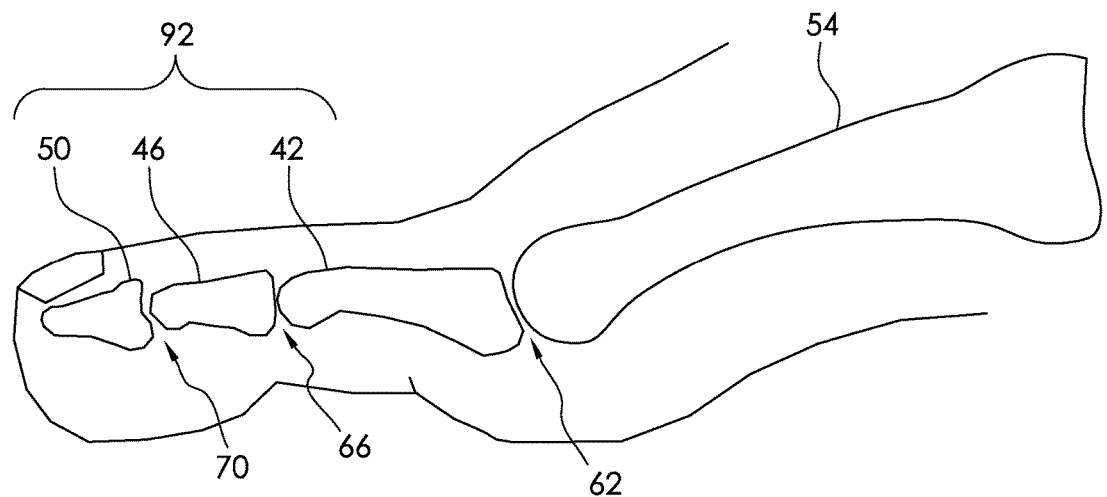
FIG. 1A is a side elevation view of what a normal toe should look like, demonstrating three phalangeal bones that make up the toe and a metatarsal bone of the foot that articulates with the toe, the toe being linear across the joints with no flexion or extension contractures.

The invention is a fastener that provides axial abutment and then axial compression of two opposing surfaces. In several embodiments, the fastener is generally a linear, cylindrical tube made in whole or in part of shape memory metal, super elastic metal, or other material having similar shape changing characteristics. The central portion of this tube is contractible and takes the shape of a bellows-like or accordion-like structure and, for conciseness, this central portion is sometimes referred to as the accordion portion or section. The accordion section has folds or pleats of various configurations that allow elongation and contraction of the fastener in a linear or nonlinear manner. The accordion section preferably is made partially or entirely of a shape memory metal. The shape memory metal may be an alloy produced or made in its austenite phase and partially or fully annealed to relieve residual manufacturing stresses. In the martensite phase, the accordion portion is plastically deformed into an elongated shape, which is its extended state. Additionally in the martensite phase, radially extending anchoring barbs are plastically deformed to lie flush, or approximately so, with the tubular sleeves. The deformed shape is maintained until implantation by use of a retaining jig or harness, or by maintaining the fastener below its phase changing transition temperature, or austenite start temperature (As). The shape memory of the metal allows the deformed device, upon an increase in temperature, to deploy the barbs radially back outward to embed themselves into the interfacing material and the bellows-like accordion section to shorten in an axial fashion, causing the barbs to pull upon the material, and thereby pull and compress together the opposing surfaces of the pieces intended to be joined together. It follows from the foregoing description, that the bellows-like accordion section is self-contractible but not self-extensible.

As an example of its use, the fastener may be implanted into opposing bone surfaces of a resected joint of a finger or a toe and a change in shape of the memory metal due to body heat after implantation causes the two bone surfaces to be drawn and compressed together. The compression imparts a resistance to the bone pieces being pulled apart, as well as resistance to their relative axial rotation, shearing and side to side bending. The forces from the shape change in the implanted fastener are transmitted through the barbs into the bone they are embedded into, pulling the bone together as the fastener contracts. These barbs also add to the rotational stability of the fastener and offer resistance to distractive forces across the fusion surfaces which would delay bone healing. As described in the following embodiments, the fastener may be used for joining together the ends of bones, repair of bone fractures, or stabilizing surgically-induced bone cuts. The embodiments may also be used for joining or coupling other objects as well, such as a piece of plywood to a cement wall or a piece of plastic to a piece of metal, two wood surfaces, or a tooth to a bone.

First Embodiment

Figure 2C:
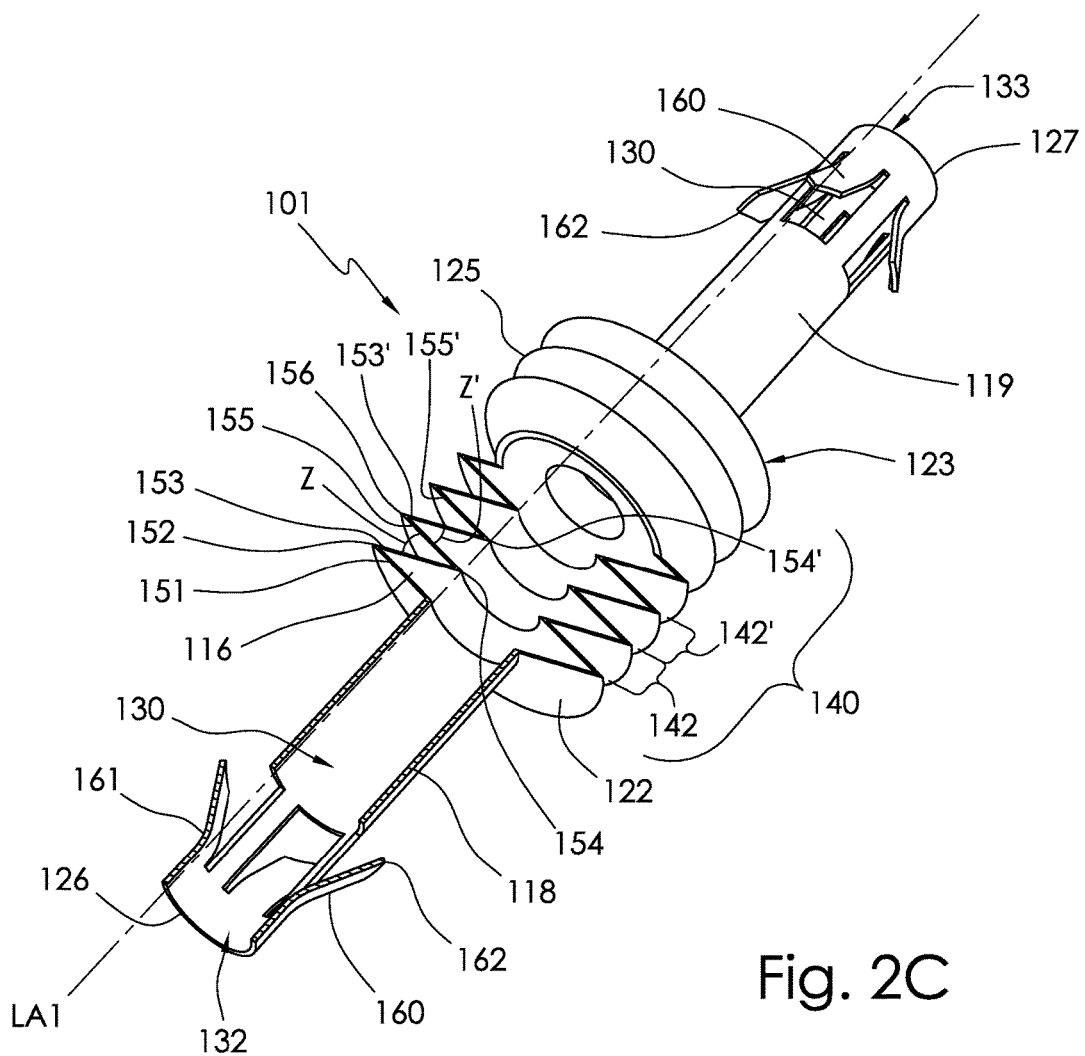
FIG. 2C is a profile perspective view with partial cut away of the fastener in FIG. 2B in its austenitic phase showing the internal aspect of a first embodiment.

A first embodiment of a fastener 101 according to the invention is shown best in FIGS. 2A, 2B and 2C, and FIGS. 3A, 3B and 3C. FIGS. 4A-4H are side elevation views of a stepwise method of using and operating the first embodiment. Fastener 101 is preferably made of a shape memory metal alloy such as Nitinol, commonly used in medical applications, but other shape memory alloys and shape memory polymers could be used for medical and non-medical applications. Shape memory alloys have two phases, an austenite phase and a martensite phase. Fastener 101 is originally manufactured in its austenite phase which is shown in FIG. 2B. After fastener 101 is manufactured, it is cooled to its martensite phase to allow it to be changed by deformation from its original shape to the new shape shown in FIG. 2A. As long as fastener 101 is kept cooled, it will remain in the deformed martensitic phase of FIG. 2A.

In a first embodiment, the fastener 101 is generally tubular or cylindrical in design and preferably is symmetrical around a central longitudinal axis (not shown). In the central aspect of fastener 101, the tubular shape is expanded into a folded, pleated or corrugated shape, hereinafter sometimes referred to as pleated, to provide a closed accordion section taking the form of a closed accordion-like contractible portion or closed bellows 140. As shown in FIG. 2A, bellows 140 has a first end face 122 and a second end face 123 that serve as the ends of the bellows section. Bellows 140 consists of a plurality of folds 125, the number of such folds controlling the development of the compressive force and the length change of the embodiment after the bellows undergo a shape change. Extending axially outward from end faces 122 and 123 of bellows 140 are further elongated tubular structures 118 and 119 respectively, hereinafter called sleeves 118 and 119. Sleeves 118 and 119 have distal ends 126 and 127, respectively, as shown best in FIGS. 2A, 2B and 3C, which are opposite the sleeve end attached to the bellows and serve as the terminal ends of the fastener (hereinafter termed the terminal ends 126 and 127). Terminal ends 126 and 127 are preferably circular in cross section and the axis through the centroid of each circular area is parallel and coincident with the central longitudinal axis of the fastener body. As seen best in FIGS. 2A-2C, terminal ends 126 and 127 each have a centrally placed portal 132 and 133, respectively. Portals 132 and 133 are connected together via a central longitudinal and cylindrical lumen or passage 130. As seen best in FIGS. 2B and 2C, this lumen passes from the terminal ends 126 and 127 axially through the center of sleeves 118 and 119, respectively. Hereinafter, lumen 130 will be termed cannulation 130. Sleeves 118 and 119 and cannulation 130 are all axially aligned with each other.

FIG. 2C shows the internal makeup of the first embodiment. Inside the accordion section 140, which is in the form of a bellows, is a hollow internal chamber 116. Cannulation 130 is contiguous with chamber 116 where sleeves 118 and 119 meet the end faces 122 and 123 of bellows 140. These are axially aligned such that a straight wire can be passed through portal 132 and cannulation 130 of sleeve 118, continue through chamber 116, and further through cannulation 130 of sleeve 119, and finally passed out of portal 133. As shown best in FIGS. 3A-3C, portal 132 and cannulation 130 have a diameter sufficient to accommodate a guide wire 43, which can be used during a surgical procedure, such as described below. The cannulation diameter is preferable only slightly larger than the wire diameter to precisely guide axial transport of the sleeves 118 and 119 and thereby insure accurate placement of the fastener 101 within the bones to be joined. Chamber 116 has an equal or greater diameter to accommodate guide wire 43.

As seen best in its austenite phase as shown in FIG. 2C, the contracted closed bellows 140 in cross-section is made up of a plurality of folds or pleats 125, both terms being interchangeable. These folds are created by a series of contiguously connected zigzag elements 142, 142', which are identical but designated separately for purposes of the description below. In this embodiment, a first leg-like zig segment 153 extends radially inward relative to a non-central longitudinal axis LA1 and a first leg-like zag segment 155 extends radially outward relative to the longitudinal axis LA1 and these segments are joined by a first inner bendable connector 154 to form a first zigzag element 142. A second leg-like zig segment 153' extends radially inward relative to the non-central longitudinal axis LA1 and a second leg-like zag segment 155' extends radially outward relative to the longitudinal axis LA1 and these segments are joined by a second inner bendable connector 154' to form a second zigzag element 142'. The non-central longitudinal axis LA1 passes tangentially along the inner connectors 154 and 154', and is a construct to define the relative directions of the zig segments 153 and 153' on the one hand and the zag segments 155 and 155' on the other hand. The zig segments and the zag segments converge toward the inner connectors at an acute angle Z and thereby form the contiguous zigzag elements 142, 142'.

The zigzag element 142, as formed by the zig segment 153 joined to a zag segment 155 by inner bendable connector 154, is joined at an acute angle Z' to the contiguous zigzag element 142' by an outer bendable interconnector 156 to form the series of contiguously connected zigzag elements 142, 142', etc. Thus, bendable connector 154 and interconnector 156 are angled connectors that face in opposite directions and are fixedly interconnected to the segments joined thereby. Also, each bendable connector joining any zig and zag segments forms either an acute angle Z or an acute angle Z', angles Z and Z' preferable being equal. An end leg-like zag segment 151 extends radially outward from an end of sleeve 118 opposite its terminal end 126 to form the end face 122 of the bellows, and an end leg-like zig segment (not shown) extends radially inward to an inner end of sleeve 119 opposite from its terminal end 127 to form the end face 123 at the opposite end of the bellows section 140.

Alternatively, the zigzag structure of bellows 140 can be considered as a series of alternating zig and zag segments joined by a series of alternating outward and inward, or upper and lower, bendable connections. As further alternatives, each zigzag element can be considered as formed by two leg-like segments joined to form a bendable connection.

The acuteness (sharpness) of angles Z and Z' can increase to provide a smaller acute angle when the accordion like portion of the fastener transitions from the martensite phase to the austenite phase upon a change in temperature, or the acuteness of angles Z and Z' can decrease to provide a larger acute angle when deformed from the austenite to the martensite phase. The plurality of zigzag elements therefore creates the plurality of folds seen in the accordion-like section of the fastener. The total number of folds can vary from one or two to hundreds or more depending on the demands required of the fastener and is not limited to what is shown in the drawings. The end face 122 of bellows 140, as formed by the zag segment 151 and the end face 123, as formed by the unshown zig segment of the bellows, are angled towards each other at a pre-determined angle, say anywhere from one degree to 60 degrees, or from 5 to 50 degrees, or from 15 to 30 degrees. The angle between the bellows end face 122 and the interconnected zig segment 153, and the angle between the bellows end face 123 and its interconnected zag segment (not shown) are preferably the same as the angle Z' above.

As seen best in FIG. 2A, set inward from terminal ends 126 and 127 along the length of each sleeve 118 and 119 are a plurality of anchoring means or tabs 160 cut into each sleeve and shown in their cold state with their surfaces aligned with the surfaces of the sleeves. These anchoring means will hereinafter be called barbs 160, because of the purpose they serve in their heated state of anchoring fastener 101 into a bone substrate and thereby preventing the fastener from being pulled out when axial stress is applied to the fastener. In other words, the barbs 160 transform the sleeves 118 and 119 into anchoring members. FIGS. 2B and 2C show four barbs 160 evenly spaced from each other around the periphery of each sleeve, and in their heated and expanded state wherein they are slanted substantially outward from the fastener axis in the direction of end faces 122 and 123 of bellows 140. At least one and preferably two or more barbs would be acceptable for this embodiment and the other embodiments described herein. Multiple barbs could also be offset from each other length-wise along the sleeves or circumferentially around the outer periphery of the sleeves such that one could conceivably have six, eight or more of these barbs per sleeve.

In forming barbs 160, each sleeve 118 and 119 is cut through its full wall thickness from the external side of its outer diameter to the internal cannulation 130, as most notably seen in FIG. 2C. Each barb 160 thus has the same thickness as the wall of sleeves 118 and 119 and, being cut from the metal of the sleeves, the outer and inner surfaces of the barb in its retracted position are substantially flush with the outer surface of the sleeve and the inner sleeve surface defining the cannulation, respectively, when the sleeve is in its cold or martensitic phase.

Figure 3A:
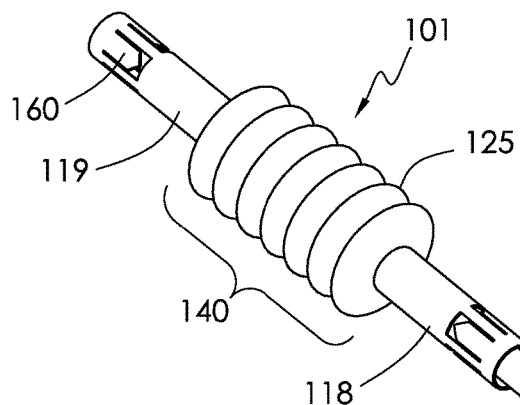
FIG. 3A is a perspective view of the first embodiment of the fastener in its martensitic phase showing a guide wire being introduced into one end of the embodiment.
Figure 3B:
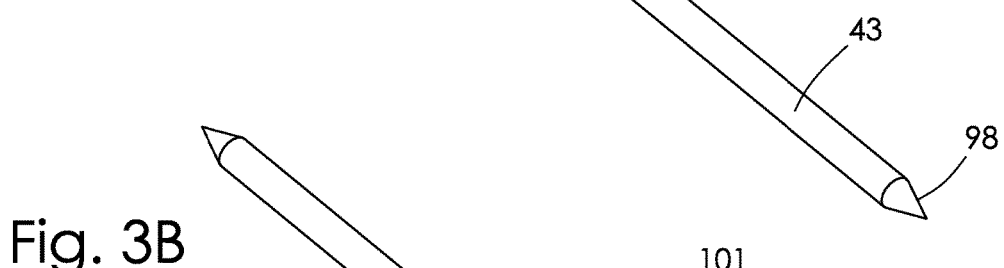
FIG. 3B is a perspective view of the fastener of FIG. 3A in its austenitic phase with a guide wire passing centrally all the way through the hollow core of the fastener's long axis. The guide wire can be passed through the embodiment in either its martensitic or austenitic phases.
Figure 3C:
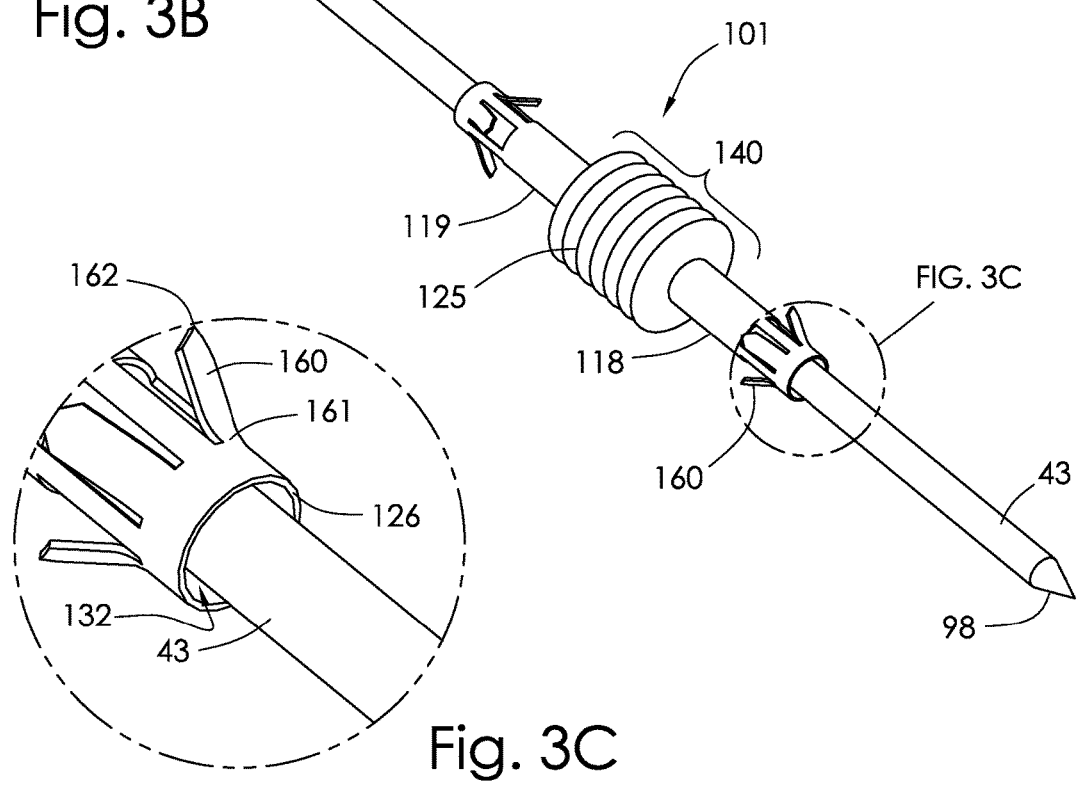
FIG. 3C is an enlarged perspective view of one end of the embodiment as shown in FIG. 3B detailing the guide wire passing into the end of the fastener and the barbs of the fastener deployed outward in their austenitic phase.

Thus, each barb 160, being made from shape memory metal and in its cooled martensitic phase, lies parallel to the long axis of fastener 101. As best shown in FIGS. 2C and 3C, barb 160 has a proximate end set outward from bellows 140 closest to terminal ends 126 and 127 of sleeves 118 and 119, which will be called base 161. Base 161 functions as the hinge point of barb 160 when the barb goes through its shape change. Set opposite base 161 and substantially towards bellows 140 along the length of barb 160 is a distal end portion in the form of an apex 162, which is generally pointed or arrowhead shaped.

Like the bellows, barbs 160 will undergo a shape change when transforming from a cooled martensite phase to an austenite phase as they are warmed to body temperature. This process is best seen in FIG. 2A, wherein fastener 101 is in its extended martensite phase, and FIGS. 2B and 2C, wherein fastener 101 has changed back to its contracted austenite phase. In so doing, each barb 160 will curl or bend outward away from the central longitudinal axis of fastener 101. Base 161 serves as the pivot or bending point for each barb. Apex 162 is designed to help the barb cut into or push its way into the surrounding substrate that fastener 101 is being implanted into in order to anchor fastener 101 and prevent its rotation or pull-out. During this warming process, bellows 140 axially shortens during the change from its martensite phase to the austenite phase as shown best in the shape change from FIG. 2A to FIG. 2B. Alternatively, barbs 160 may be partially deployed in their cold state by being partially bent outwardly at time of insertion into bone in order to mitigate slipping of the fastener and prevent accidental pullout before being fully deployed. Partially deployed barbs may be made of a resilient material.

It is also possible that barb 160 can exhibit superelastic properties wherein the undeformed shape can recover without the application of heat. The shape memory and superelastic properties of nitinol can coexist within a single fastener. For example the accordion like portion can exhibit the shape memory properties of nitinol while the barbs exhibit superelastic properties.

Operation of First Embodiment

Fastener 101, as well as the other embodiments described herein, may be made from a shape memory alloy, such as Nitinol, though there are other shape changing materials available that also may be used. When any of these embodiments are used, say for a surgical procedure like a hammertoe correction, the properties of the metal or other material allow it to exist in different shapes at different temperatures. For example, when the Nitinol embodiment is moved from a cool or cold state, at which time it is in its martensite phase, and then implanted in the body and warmed to body temperature, it will undergo a change in its shape as it transforms to its austenite phase.

As shown again in FIGS. 2A and 2B, bellows 140 will shorten along its axial length, like an accordion, during its phase change from a martensitic phase to an austenitic phase. At the same time, barbs 160 on sleeves 118 in 119 will go through a phase change as well, expanding radially outward from their base 161 such that they will anchor the embodiment into a substrate, for example, the bones of a proximal and middle phalanx of a toe or finger. This axial shortening of bellows 140 provides the necessary compressive force to draw together two bone ends that have been surgically prepared or fractured.

FIG. 1A demonstrates a normal toe which is made up of multiple bones. The parts of a normal toe include a metatarsal bone 54 and a proximal phalanx 42. Together the articulation of metatarsal bone 54 and proximal phalanx 42 make up a metatarsal phalangeal joint 62 or MTPJ 62. More distally along the toe, a second articulation is made between proximal phalanx 42 and a middle phalanx 46. This articulation constitutes a proximal interphalangeal joint 66 or PIPJ 66. Even more distally along the length of the toe, a third articulation occurs between middle phalanx 46 and a distal phalanx 50. This articulation constitutes a distal interphalangeal joint 70, or DIPJ 70. The proximal phalanx 42, the middle phalanx 46, and the distal phalanx 50 together comprise a phalange 92. Anatomically, a normal toe lies in a straight or linear fashion along its length from metatarsal bone 54 to the distal end of distal phalanx 50, as shown best in FIG. 1A. PIPJ 66 and DIPJ 70 generally have no substantial angular deformity while MTPJ 62 normally rests at about a 15 degree angle.

Figure 1B:
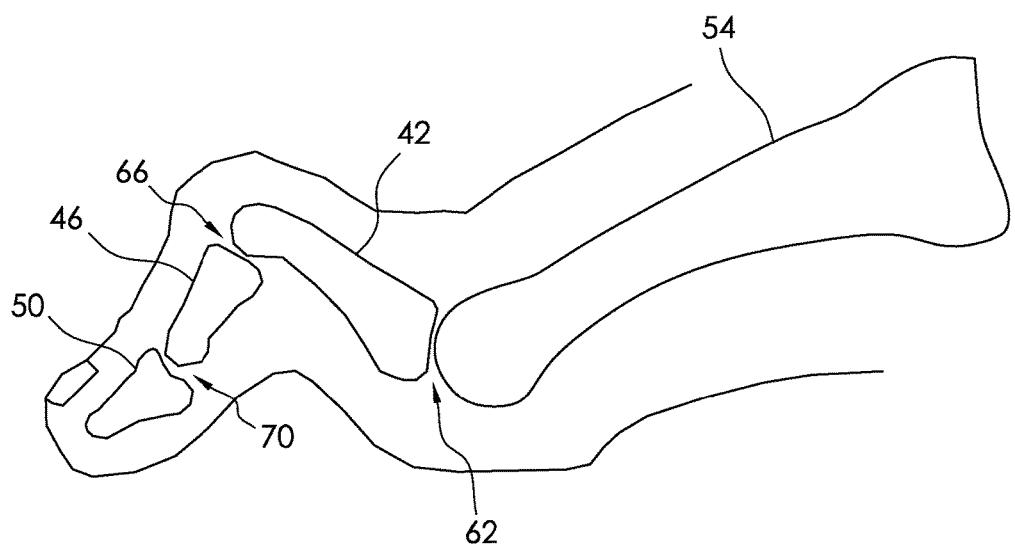
FIG. 1B shows a side elevation view of a hammertoe where the toe is non-linear. There are extension and flexion contractures of the joints of the toe effectively causing the toe to be crooked.

Looking at FIG. 1B, one can see a hammertoe, a toe that is deformed or not straight. Here the toe has angular contraction deformities at the joints along the length of the toe. In a classic hammertoe deformity, as demonstrated in FIG. 1B, there is a contracture of MTPJ 62 well beyond a normal 15 degrees whereby proximal phalanx 42 is upwardly displaced on metatarsal bone 54. Tight ligaments and tendons, not shown, facilitate holding the deformed MTPJ 62 in this position, contributing to the toe's pathology. Then, looking at PIPJ 66, middle phalanx 46 is contracted downward. Again, tight ligaments and tendons facilitate holding deformed PIPJ 66 in this position. Lastly, at DIPJ 70, distal phalanx 50 is contracted upward in relation to the downward positioned middle phalanx 46. Yet again, tight ligaments and tendons facilitate holding the deformed PIPJ in this position.

Figure 4A:
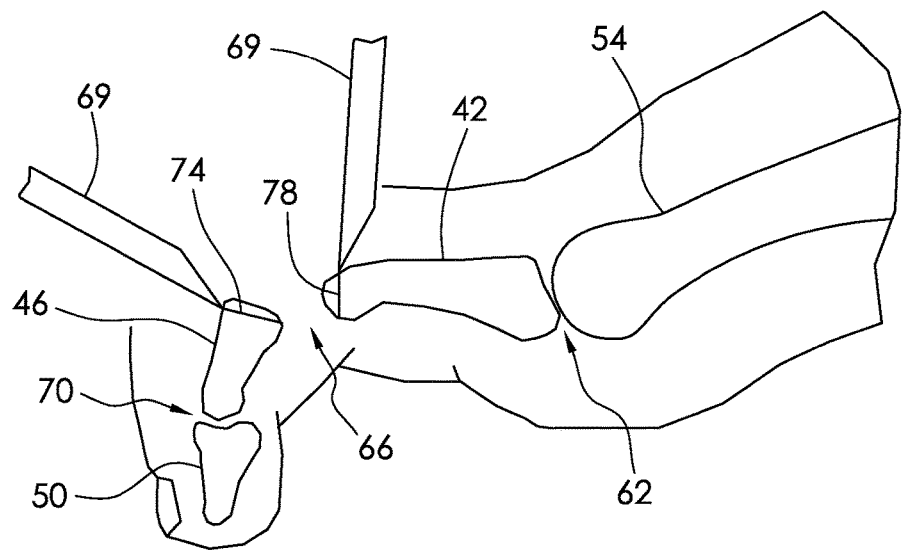
FIG. 4A is a side elevation view of a toe wherein the proximal interphalangeal joint has been surgically opened and a cutting blade demonstrates the resection area of bone from the proximal phalanx and middle phalanx that comprise the joint.

In the surgical correction of a hammertoe, the general principle is to address the primary deformity at the level of PIPJ 66. To do so requires making a surgical incision over PIPJ 66, dissecting the soft tissues down to the ligaments and tendons of the joint, and cutting these to reflect them out of the way such that the surgeon can access the bones of PIPJ 66, namely proximal phalanx 42 and middle phalanx 46. Hereinbelow is the application of the first embodiment. The application and operation can best be seen in FIGS. 4A-4H. FIG. 4A shows a hammertoe where surgical exposure of the bones of PIPJ 66 has been performed. A surgical saw 69 is used to cut the articulating portion of bone from proximal phalanx 42, perpendicular to its long axis, effectively producing a flat cut surface 78 of proximal phalanx 42. Subsequently a surgical saw is again used and the articulating portion of bone from the middle phalanx 46 is cut away, producing a flat cut surface 74 of middle phalanx 46. The flat cut surfaces 74 and 78 are sometimes referred to hereinafter as abutment surfaces.

Figure 4B:
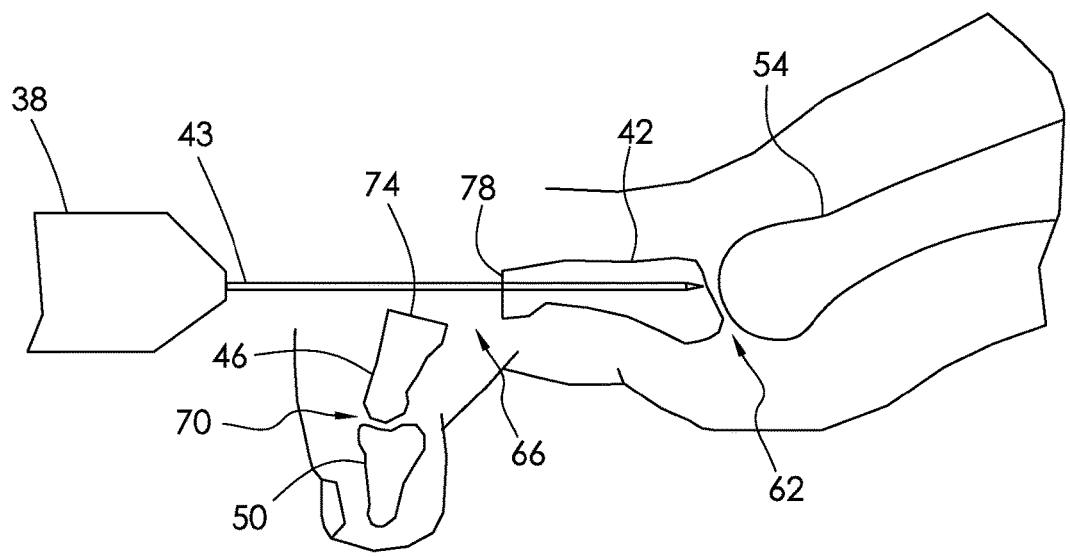
FIG. 4B is a side elevation view showing the joint surfaces resected and creating a flat surface for the two bones to abut against each other. A guide wire has been introduced through the flat resected bone surface of the proximal phalanx and passed or driven down the central axis of the phalanx.
Figure 4C:
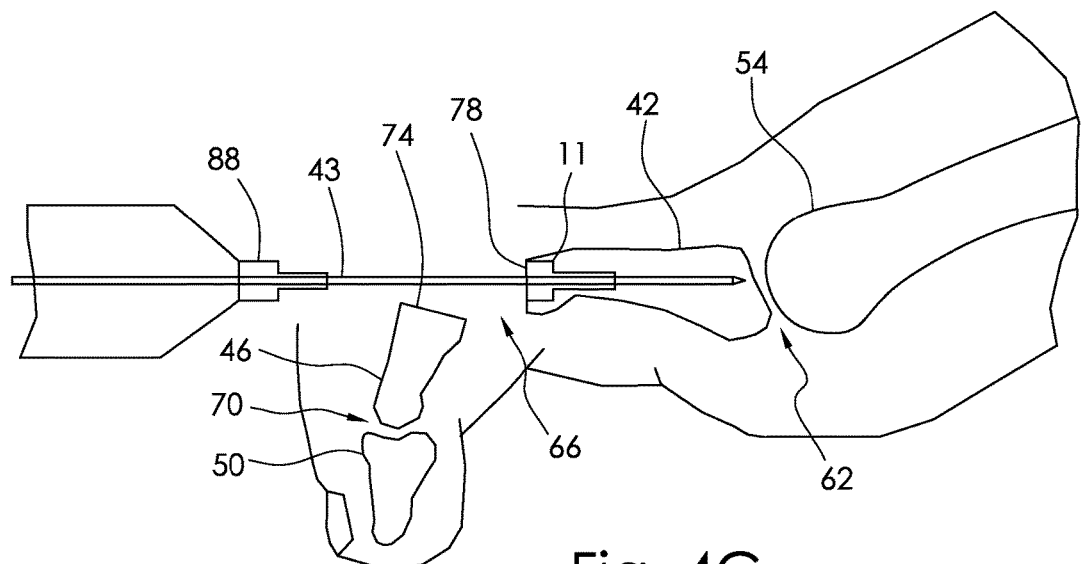
FIG. 4C is a side elevation view showing the guide wire still in place in the proximal phalanx. A counter-borer has been placed over the guide wire and driven into the proximal phalanx, reaming the bone to create a void for placement of the fastener.

In FIG. 4B, a guide wire 43 attached to a wire driver 38 is then inserted into the abutment surface 78 of proximal phalanx 42 and advanced down the center of proximal phalanx 42 to the area of MTPJ 62 but not into it. Wire driver 38 is then removed from over guide wire 43. As shown in FIG. 4C, a counter-borer 88 is then slid over guide wire 43 and used to ream out some of the bone from proximal phalanx 42, leaving a hollow tubular shape or bore in the bone matching the shape of approximately one-half the length of fastener 101. Hereinafter, this matching hollow tubular bore will be termed bore hole 11. If one of the non-round embodiments is used, say a square or triangular embodiment, a similarly shaped broach may be used instead of a counter-borer. Counter-borer 88 is then removed from proximal phalanx 42 and guide wire 43 is subsequently removed with wire driver 38.

Figure 4D:
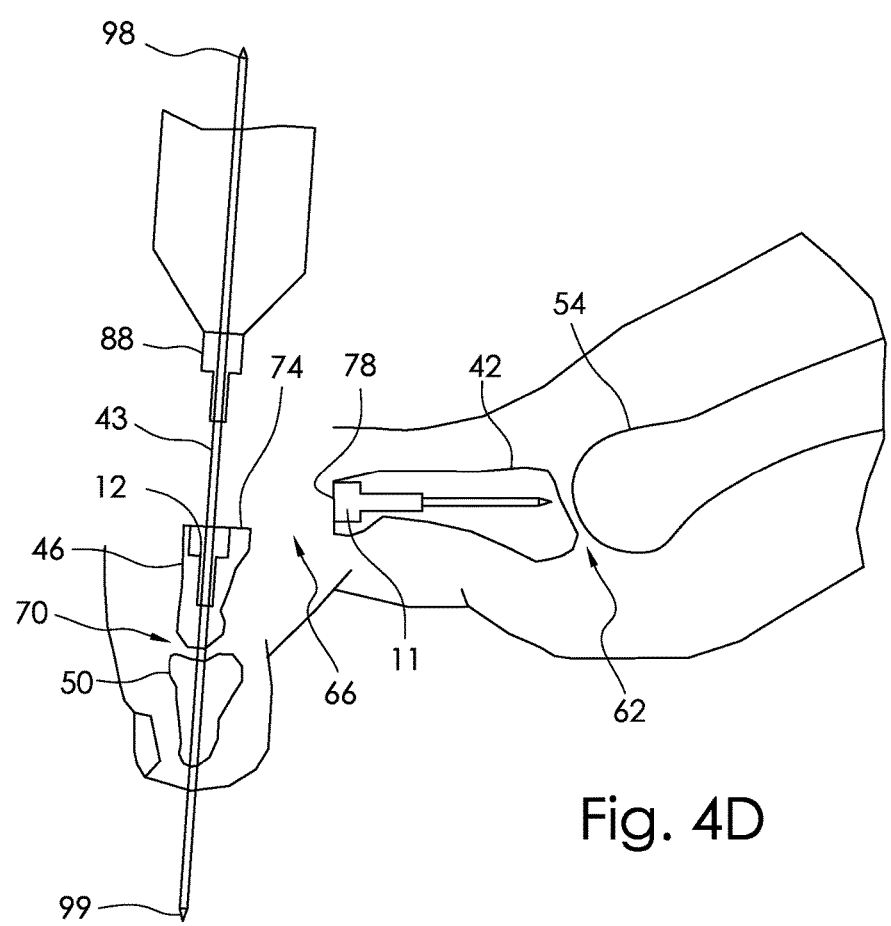
FIG. 4D is a side elevation view showing the guide wire removed from the proximal phalanx and inserted into the middle and distal phalanx and sticking out passed the end of the toe. The counter-borer has been placed over the guide wire and the middle phalanx reamed with the counter-borer, creating a void for placement of the fastener in the middle phalanx.
Figure 4E:
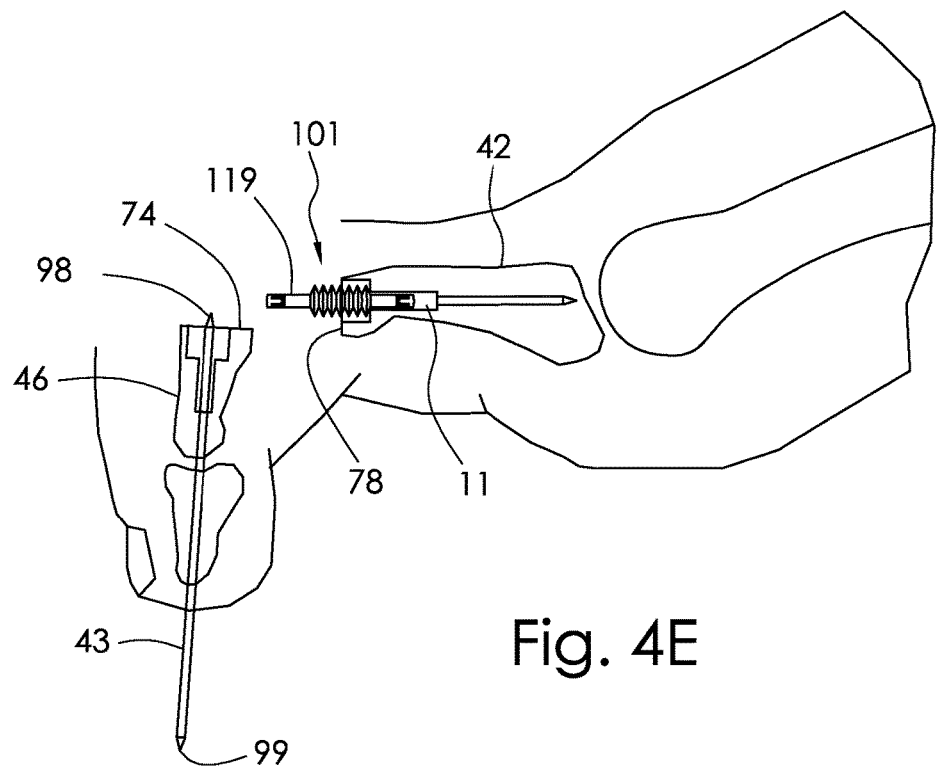
FIG. 4E is a side elevation view showing the guide wire repositioned in the toe so that its tip sits just proud of the resected bone surface of the middle phalanx. The view also shows the first embodiment of the fastener in its martensitic phase inserted into the bore hole created in the proximal phalanx.

In FIG. 4D, guide wire 43 is placed into the center of abutment surface 74 of middle phalanx 46. Guide wire 43 is then driven axially down the central long axis of middle phalanx 46, driven across DIPJ 70 into distal phalanx 50, and then out through the skin on the end of the toe. The wire driver 38 is then removed from a proximal end 98 of guide wire 43. Counter-borer 88, shown in FIG. 4D, is then slid over proximal end 98 of guide wire 43 and used to bore into middle phalanx 46, producing a hollow tubular shape that matches the other one-half of fastener 101, hereinafter termed bore hole 12. It is also contemplated for this embodiment and those described herein below that the respective sleeves and corresponding portions of the bellows of the fastener may differ from each other in size, length and/or shape with corresponding differences in their bore holes. Counter-borer 88 is removed from guide wire 43 and, as shown in FIG. 4E, using wire driver 38, guide wire 43 is then advanced further out the end of the toe so that proximal end 98 of the guide wire is sitting just proud of abutment surface 74 of middle phalanx 46. Up until this point, the fastener has been previously sterilized and has been kept refrigerated so as to maintain the fastener at its martensite phase, elongated and the barbs lying flush with the sleeves of the fastener.

Figure 4F:
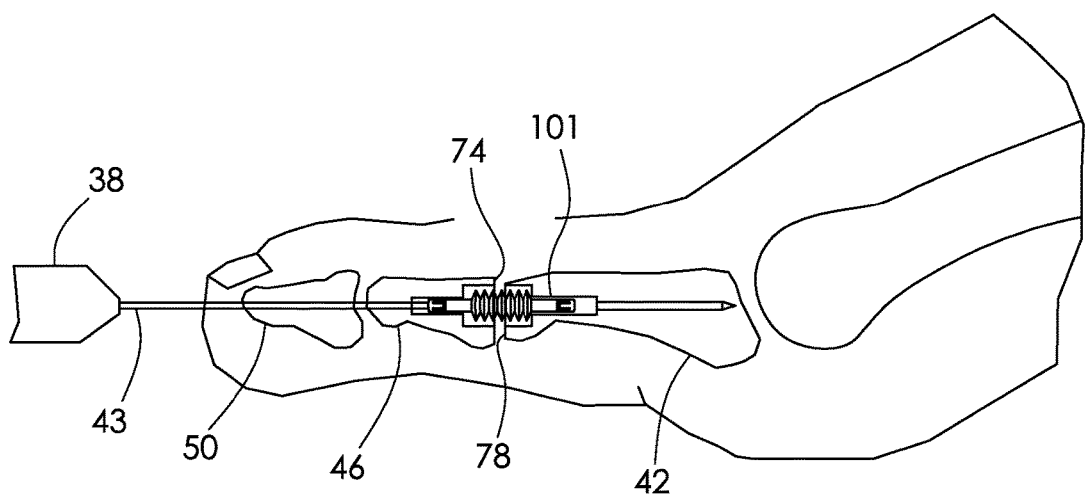
FIG. 4F is a side elevation view showing that the toe has been manipulated and reduced into position wherein the tip of the guide pin just proud of the middle phalanx has been inserted into the end of the first embodiment of the fastener and the fastener inserted into the void of the middle phalanx. The fastener is still in its martensitic phase. The adjoining surfaces of the proximal and middle phalanx have not yet been compressed together.

FIG. 4E shows fastener 101 imparted into matching bore hole 11 of proximal phalanx 42. The surgeon then manipulates the bones by grabbing proximal phalanx 42 and middle phalanx 46 and raising middle phalanx 46 upward and placing proximal end 98 of guide wire 43 into sleeve 119 of the fastener. Middle phalanx 46 is then press fitted onto sleeve 119 and the portion of fastener 101 that remains protruding from proximal phalanx 42. As middle phalanx 46 is imparted onto fastener 101, guide wire 43 passes along cannulation 130 of the fastener. As shown in FIG. 4F, abutment surface 78 of proximal phalanx 42 and abutment surface 74 of middle phalanx 46 are then manually approximated together such that they are contacting each other. At this point, the proximal phalanx 42, middle phalanx 46, and distal phalanx 50 are all now aligned straight and the fastener 101 warms to body temperature.

Figure 4G:
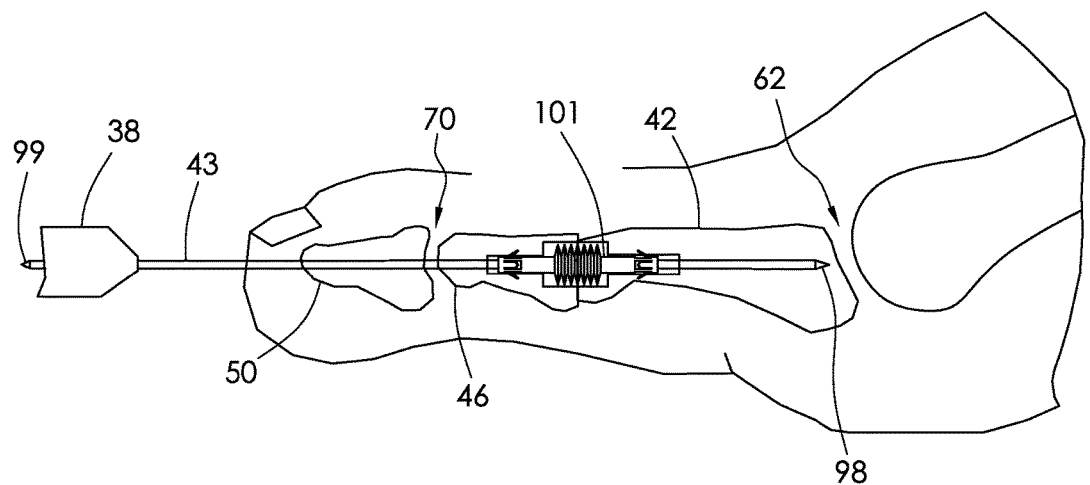
FIG. 4G is a side elevation view of the fastener having undergone its phase change and is now in its austenitic phase. The barbs on the fastener have deployed into the bone and the accordion-like bellows has compressed the bone surfaces together via its shape change. The guide wire has also been driven all the way into the proximal phalanx.

As the fastener 101 warms to body temperature, it changes from its cooled martensite phase to its warmed austenite phase, undergoing a shape change. In so doing, barbs 160 deploy by expanding radially outward from the central axis of the cannulation 130 and embed themselves into the bone of the surrounding proximal phalanx 42 and middle phalanx 46. Transitioning from FIG. 4F, FIG. 4G shows that as this process occurs, the bellows, in accordion fashion, shortens along its axial length, drawing together into abutment and compressing together the cut surface 74 of middle phalanx 46 and the cut surface 78 of proximal phalanx 42. In so doing, acute angles Z and Z' (as seen in FIG. 2C) becomes more acute (smaller). Also, leg-like zig segment 153 and leg-like zag segment 155, as well as corresponding segments along the length of bellows 140, draw closer together through the shape changes in these segments and in the outer bendable interconnectors 152 and 156 and the inner bendable connector 154, as well as in the corresponding bendable connectors and interconnectors along the length of bellows 140. The resulting compressive force across the middle and proximal phalanx provides the stability necessary to allow the two bones to heal together. It is at this point that the surgeon will decide if the procedure is complete. If he or she feels the procedure is complete, the guide wire 43 is removed from the toe as facilitated by use of wire driver 38 on distal end 99 of guide wire 43. Then layered closure of the tendon, ligaments, and skin is performed. Fastener 101 remains in place to provide stability during healing.

Figure 4H:
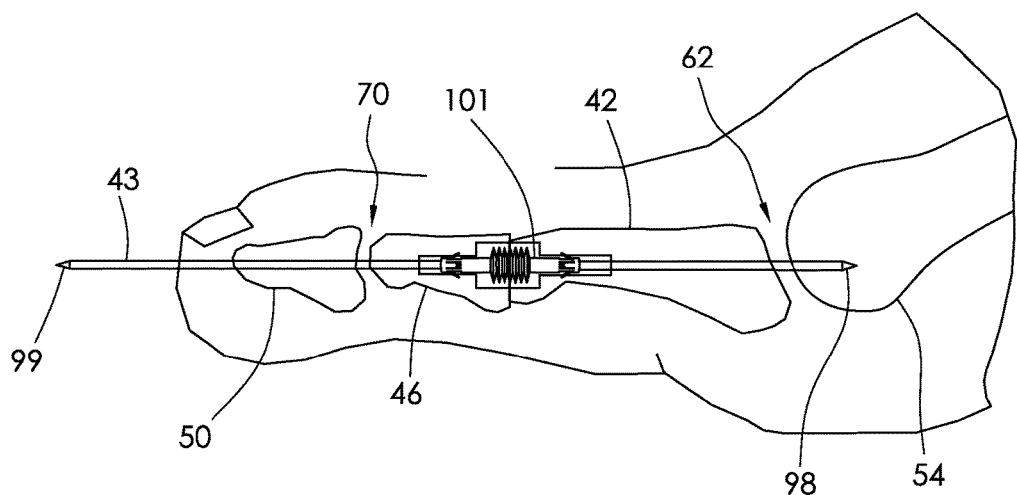
FIG. 4H is a side elevation view showing the fastener again in position across the proximal interphalangeal joint and having compressed together the bone surfaces. The guide wire has been driven across the metatarsal-phalangeal joint into the metatarsal, stabilizing the joint.

There are times however when the surgery is not complete at this point. Oftentimes adjunctive procedures are performed on DIPJ 70 and MTPJ 62 at the same time as the osteosynthesis procedure on PIPJ 66. Typically these procedures involve tendon or ligament surgery, or sometimes cutting of bone. Osteosynthesis is rarely performed on DIPJ 70 or MTPJ 62 but the tendon and ligament procedures that might be performed can leave the joints unstable due to soft tissue imbalances. If the surgeon decides that she or he needs to afford stability to these joints as well, then she or he may decide to utilize another important function of fastener 101, that being cannulation 130, which will allow guide wire 43 to be left within the toe during healing along with fastener 101. As shown in FIG. 4H, instead of removing guide wire 43 after the fastener has gone through its shape change, a surgeon may advance guide wire 43 through cannulation 130 and across MTPJ 62 into metatarsal 54, providing stability to MTPJ 62 so that it cannot be moved during the healing process. Instead, the surgeon may leave the guide wire 43 in place across DIPJ 70 without crossing MTPJ 62, as best shown in FIG. 4G. This then affords stability only to DIPJ 70, if necessary. The distal end 99 of guide wire 43 is then left sticking out the end of phalanx 50. The wire is left in this position for approximately 4-6 weeks after the surgery while osteosynthesis or fusion occurs across proximal phalanx 42 and middle phalanx 46. After healing has occurred, the surgeon may remove guide wire 43 in their office by grasping the exposed distal end 99 with a pliers and pulling it out, thus negating a return to the operating room.

Second Embodiment

Figure 5:
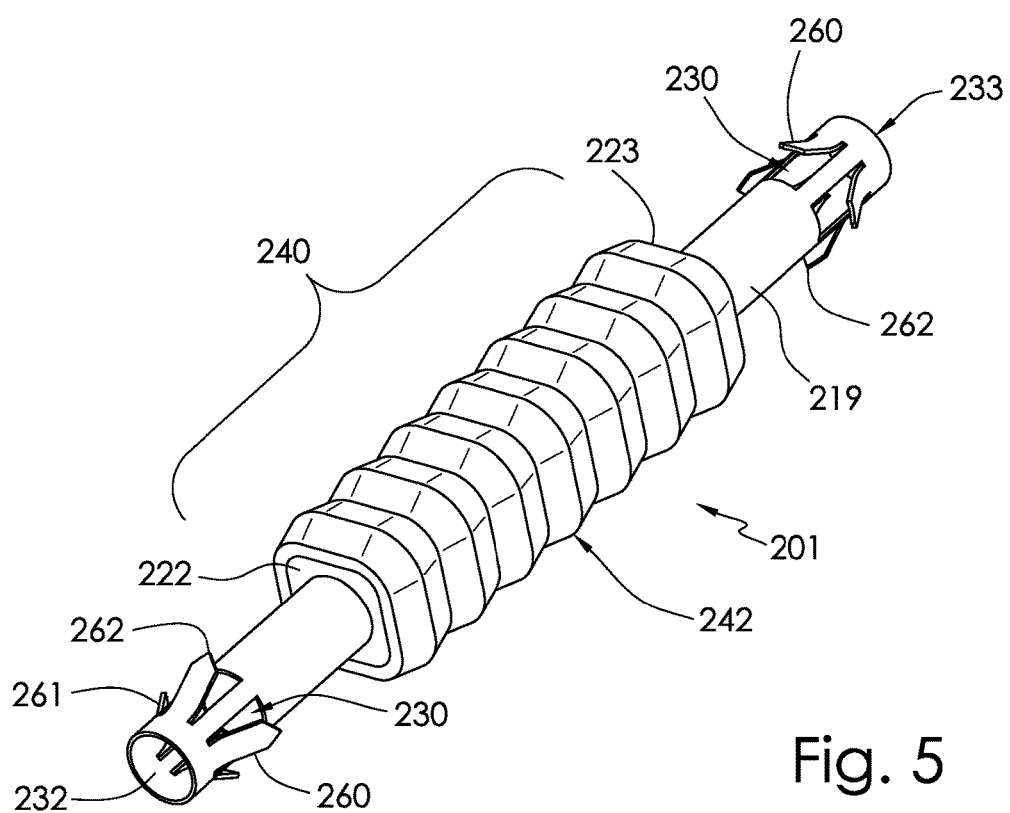
FIG. 5 is a perspective view of a second embodiment of the fastener in its martensitic phase. It shows the bellows portion of the fastener as an elongated square bellows instead of an elongated cylindrical or tubular bellows.

FIG. 5 shows a second embodiment as an alternative to the first embodiment wherein a fastener 201 has a similar appearance to fastener 101 but has a closed accordion-like section in which pleats 242 of a bellows 240 are square shaped instead of round or cylindrical. Still other cross-sectional shapes may be used for the bellows section as well, such as oval, rectangular or triangular, but all of these shapes are still folded or pleated along the longitudinal axis of the contractible portion. Although the structural details of the accordion section and the anchoring members may differ, the second embodiment has the same functional features as described for the first embodiment and as shown best in FIG. 2C. Thus, fastener 201 has a cannulation 230 passing centrally through the long axis of the fastener as in the first embodiment of FIGS. 2A-2C. Anchoring means in the form of a plurality of barbs 260 are also similar to the first embodiment, as is the functionality of the accordion portion. Fastener 201 has a terminal end 232 and a terminal end 233 that serve as the ends of the fastener. A sleeve 219 is fixedly joined to the bellows 240 at an end face 223 of the bellows beset opposite the terminal end 233. The bellows has a similar end face 222 on its opposite side. Again, sleeve 219 has a plurality of anchoring means or barbs 260 that serve to anchor the fastener into the surrounding bone or substrate. Herein, barbs 260 are bendably joined to sleeve 219 at a base 261. Beset opposite the base 261 is an apex 262 of each barb which provides further means for anchoring into bone, these features all having been similarly described in the first embodiment.

Third Embodiment

Figure 6A:
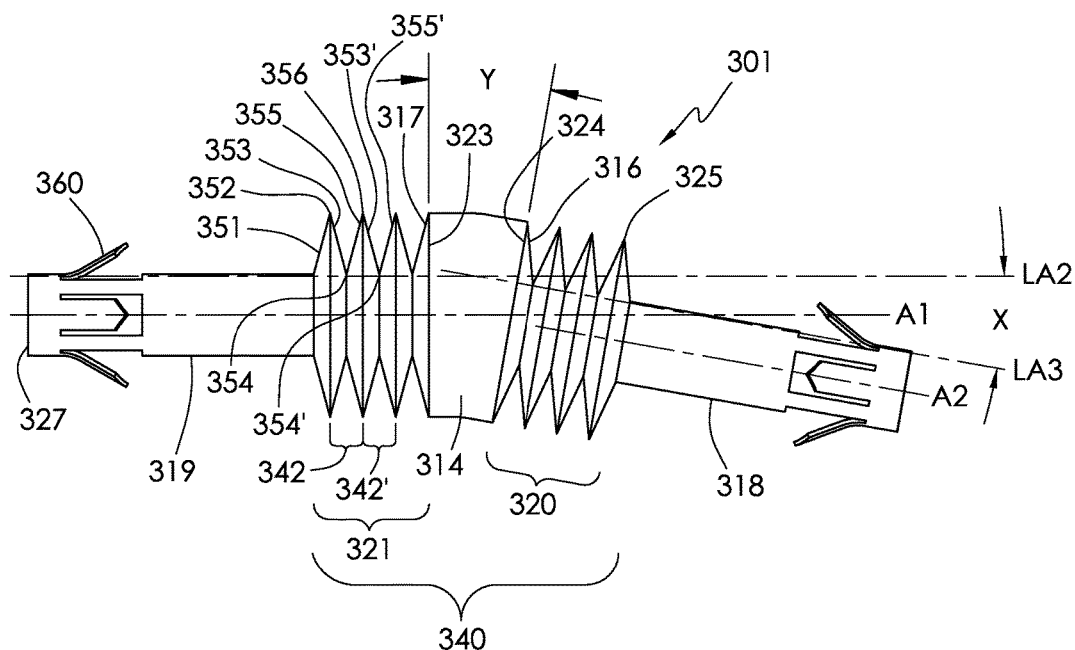
FIG. 6A is a side elevation view showing a third embodiment of the fastener wherein the fastener is angled to allow fusion of the proximal interphalangeal joint at an angle.

A third embodiment allows for angular positioning of the middle and proximal phalanx of the toe. As shown in FIG. 6A, a fastener 301 is not linear but rather angled and is seen here in its austenite phase, having shortened from an elongated position and a plurality of anchoring means or barbs 360 having expanded outward as already described hereinabove. In this figure, the angularity of the fastener occurs in the mid-portion of a bellows section 340. Situated substantially towards the middle of bellows section 340, a fold 325 has been replaced by a solid boss 314, wherein the respective ends 323 and 324 of this boss are angled relative to each other instead of being parallel. The boss 314 has an end face 316 that faces an anchoring sleeve 318 and an end face 317 that faces an anchoring sleeve 319. As shown, boss 314 may divide the accordion-like bellows section into approximately two equal half portions 320 and 321. However, boss 314 may instead replace the first fold or last fold or be situated anywhere between the first fold and the last fold. Both end faces 316 and 317 of boss 314 are preferably formed by leg-like zig or zag segments of these bellows portions. The two bellows portions 320 and 321 of this embodiment each have the same functional features as described for the bellows portion 140 of the first embodiment as shown best in FIG. 2C.

A boss end face 323 is preferably symmetrical about a central axis A1 of sleeve 319 and a boss end face 324 is preferably symmetrical about a central axis A2 of sleeve 318, which is inclined at an angle X relative to the axis A1 of sleeve 319, causing end faces 323 and 324 to slope away from each other at an angle Y. Sleeves 318 and 319 are thus no longer coaxial in this embodiment and the angularity of boss 314 is translated to the angular relationship X between the central sleeve axes. Angle Y preferably equals angle X. Most surgeons prefer to fuse a toe straight or at zero degrees while some may prefer a ten to fifteen degree angle. When it comes to fingers, the joints are often fused at greater angles and so the embodiment may need an angularity of greater than fifteen degrees, such as twenty degrees to fifty degrees for a functional result. It is further contemplated that sets of fasteners may be provided to give boss angularities at least between 1° to 15°, preferably ° to 20°, more preferably 1° to 45°, even more preferably 1° to 60°, and most preferably in increments of 5°.

Although the structural details of the accordion section and the anchoring members may differ, the third embodiment has the same functional features as described for the first embodiment and as shown best in FIG. 2C. Thus, the folds or pleats 325 are again formed by a plurality of zigzag elements as detailed in the first embodiment. In this third embodiment, an end leg-like zag segment 351 extends radially and acutely outward from a non-central long axis LA2 of sleeve 319 and is beset opposite a terminal end 327. Segment 351 extends outward preferably at an acute angle but also could possibly be perpendicular to the long axis LA2 of sleeve 319. A leg-like zig segment 353 joins the segment 351 acutely at a bendable interconnector 352. A zag segment 355 is joined to zig segment 353 acutely by a bendable connector 354 to form an outwardly facing acute angle (like angle Z in FIG. 2C). As in the first embodiment best seen in FIG. 2C, adjacent zigzag elements 342 and 342' are joined by a bendable interconnector 356 to form an inwardly facing acute angle (like angle Z') between zag segment 355 and a second zig segment 353' of adjacent zigzag element 342', and second zig segment 353' being joined to a second zag segment 355' by a second inner bendable connector 354'.

Also similar to the first embodiment and to later embodiments, the zig segments 353 and 353' extend inward toward the non-central long axis LA2 of sleeve 319, and the zag segments 355 and 355' extend outward away from the non-central long axis LA2 of sleeve 319. In the same fashion, the zig segments of the second bellows portion 320 extend inward toward a non-central long axis LA3 of sleeve 318, and the zag segments of this bellows portion extend outward away from the non-central long axis LA3 of sleeve 318. The axes LA1 and LA2 pass tangentially along the inner connectors 354 and are constructs to define the relative directions of the zig segments on the one hand and the zag segments on the other hand. In addition, each bendable connector or interconnector joining any two leg segments forms an acute angle between the joined segments. This angle can again increase or decrease when the closed accordion like bellows portion 340 changes between the martensite and austenite phases. Alternatively, each zigzag element making up a fold can be considered as formed from any two leg-like segments joined together acutely by either a bendable connection or interconnection. The plurality of zigzag segments can vary in number as described earlier.

Operation of Third Embodiment

Figure 6B:
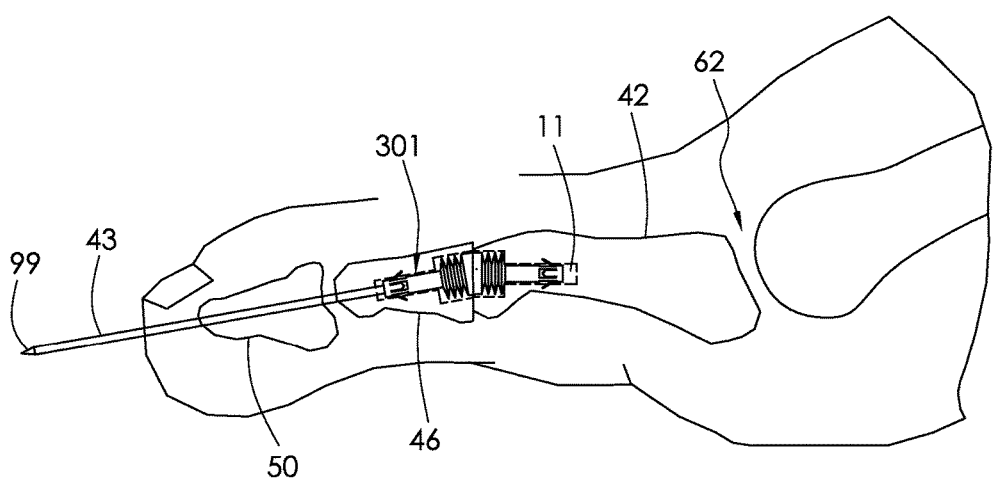
FIG. 6B is a side elevation view showing the alternative embodiment of FIG. 6A placed in the proximal interphalangeal joint, fusing the bones together at an angle.

The final placement of the fastener 301 is shown best in FIG. 6B. The application of the third embodiment requires the proximal phalanx and the middle phalanx to be prepared with angular cuts. The cut surface of the proximal or middle phalanx, instead of being cut perpendicular to the long axis of the bone, is cut at an angle to the long axis. The sum of the angles cut into both phalanxes is such that it matches the built-in angle of the embodiment; say ten to fifteen degrees for a toe or whatever the angle of the embodiment.

The step wise application of the embodiment is otherwise the same as in FIGS. 4A through 4F. The proximal phalanx 42 is cut and the middle phalanx 46 is cut, each at one-half of the desired full angle. A guide wire is placed axially into the proximal phalanx and the phalanx is then counterbored to create a bore hole 11 for the implant. The guide wire 43 is then removed and driven axially into the middle phalanx 46 and out the end of the toe. Guide wire 43 is positioned so that it is nearly flush with the cut surface of middle phalanx or slightly protruding. A counter-borer is then placed over the guide wire and a hole created to appropriate depth to match one-half the shape of the second embodiment. FIG. 6B shows the angled fastener in place in a toe with a slight angularity to the fusion site. The guide wire is then left in place or it can be removed at this point. Fastener 301 is inserted into matching bore hole 11 of proximal phalanx 42. Middle phalanx 46 is positioned onto the portion of fastener 301 that remains protruding from the proximal phalanx 42, all in similar fashion as described for the first embodiment.

As the middle phalanx 46 is installed onto fastener 301, guide wire 43 is free to pass along the central cannulation of the fastener up to the point where the angularity prevents it from passing any further and so this embodiment is more desirable when pinning of the MTPJ 62 is not necessary. Cut surface 78 of proximal phalanx 42 and cut surface 74 of middle phalanx 46 are manually held together such that they are in intimate contact with each other until fastener 301 goes through its shape change. Thus, other than the bone cuts and angular shape of fastener 301, the function of the embodiment is the same as the first embodiment.

Fourth Embodiment

Figure 7A:
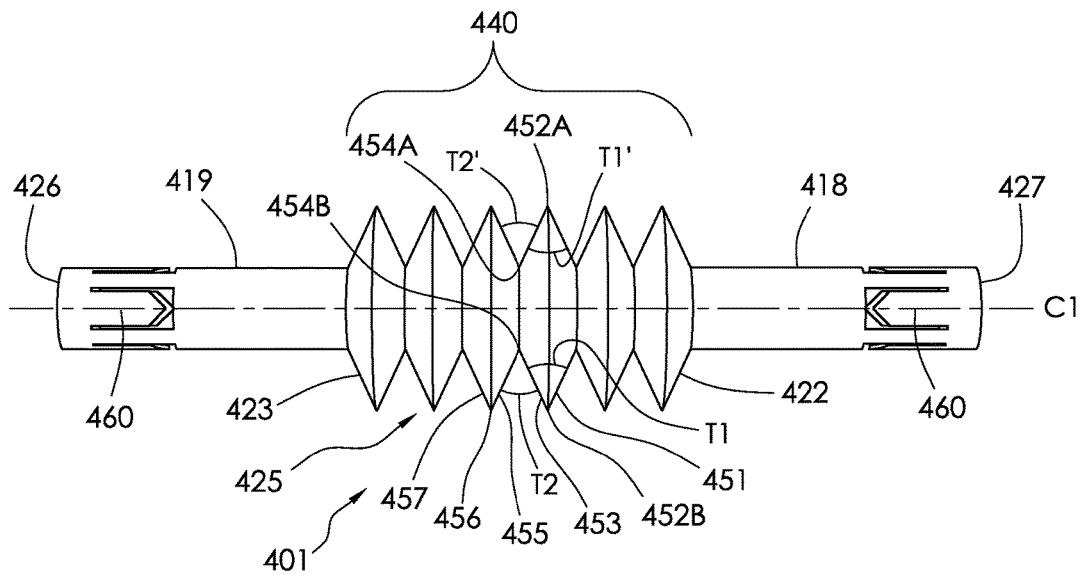
FIG. 7A is a side elevation view of a fourth embodiment of the fastener similar to the FIG. 6A embodiment and is shown in its martensitic phase. However, this alternative embodiment goes through an angular shape change built into the bellows as will be seen in FIG. 7B.
Figure 7B:
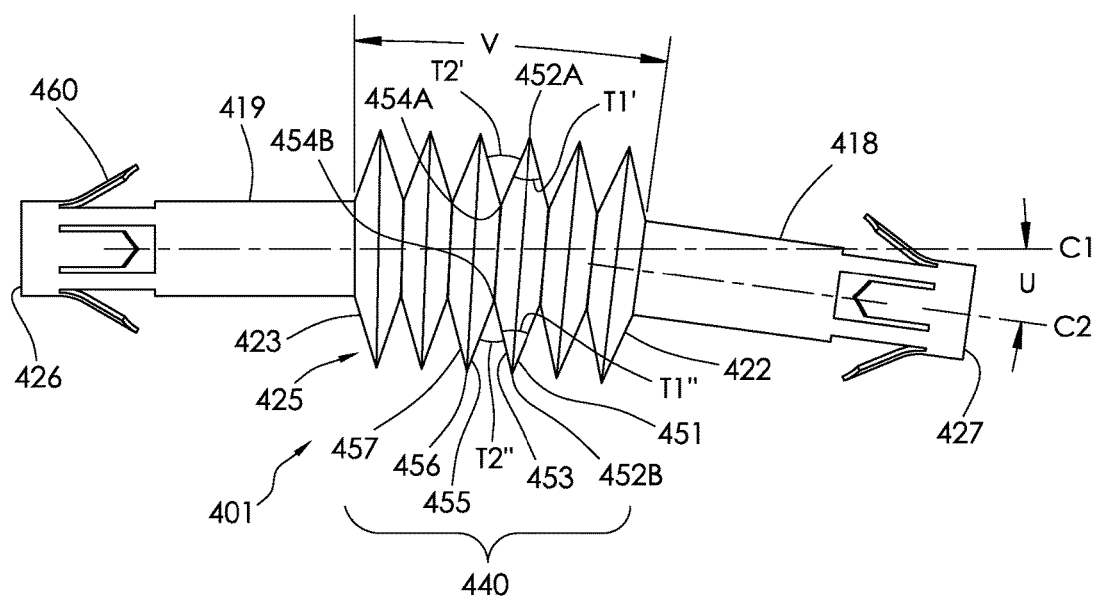
FIG. 7B is a side elevation view of the embodiment of FIG. 7A wherein the fastener is shown in its austenitic shortened phase and has also undergone an angular change for the purpose of fusing a toe in an angular position.

FIGS. 7A and 7B show an alternative embodiment wherein a fastener 401 again allows bone fusion in an angular fashion but this time, simultaneously with the axial shortening of the accordion-like section, which is in the form of a bellows 440, there is an angular shape change as shown in FIG. 7B. Fastener 401 is manufactured in its austenite phase, as shown in FIG. 7B, in which bellows 440 subtends an angle V between a plane defined by an inner end 426 of sleeve 418 and a plane defined by an inner end 427 of sleeve 419, angle V imparting an angle U between a central longitudinal axis C1 of sleeve 419 and a central longitudinal axis C2 of sleeve 418. In its martensite phase as shown in FIG. 7A, fastener 401 looks identical to the first embodiment (except fastener 101 as shown in FIGS. 2A-2C has seven folds) and a central longitudinal axis C1 extends along sleeves 418 and 419. In FIG. 7A, the central longitudinal axis C2 of FIG. 7B of sleeve 418 overlaps the central longitudinal axis C1 of sleeve 419 because the austenite fastener has been straightened by deformation, thereby eliminating the angularity of the fastener. Thus, although the structural details of the accordion section and the anchoring members may differ, the fourth embodiment has the same functional features as described for the first embodiment and as shown best in FIG. 2C. The difference is shown in FIG. 7B, wherein fastener 401 is originally manufactured in its austenite, resting, or unstressed, phase with a bend in bellows 440.

As seen in FIG. 7A, an end face 422, preferably formed by a zig segment of the bellows, and an end face 423, preferably formed by a zag segment of the bellows, are angled towards each other at a pre-determined acute angle, face 422 preferably being parallel to internal zig segment 455 and face 423 preferably being parallel to internal zag segment 453 such that the acute angle between faces 422 and 423 is equal to an acute angle T1 between zig segment 453 of one zigzag element and zag segment 451 of a contiguous zigzag element as joined by an interconnector 452. There is also an acute angle T2 between the zig segment 453 and a zag segment 455 as joined by an inner connector 454 to form an intermediate zigzag element. These acute angles are preferably from one degree to 60 degrees, more preferably from five degrees to fifty degrees, or anywhere within the other angle ranges as discussed above in regard to angles Z and Z' of the first embodiment. As in the other embodiments shown in the drawings and described herein, any single inner bendable connector will join a leg-like zig segment and a leg-like zag segment at an outward facing acute angle (such as T2), and any single outer bendable interconnector will join a leg-like zag segment and a leg-like zig segment at an inward facing acute angle (such as T1), these acute angles preferably being equal as in the martensitic phase of FIG. 7A. The acuteness of the inward facing angle of any one bendable interconnector and of the outward facing angle of any one bendable connector may vary from those of any adjacent zigzag element or fold.

As best seen in FIG. 7A, a plurality of anchoring means or barbs 460 are pressed flat in the martensite phase so that they are flush and in alignment with the walls of sleeves 418 and 419. The accordion-like section in the form of a bellows 440 is then stretched or elongated by deformation in the martensite phase and angles U and V are eliminated so that the fastener is now linear as shown in FIG. 7A, and not angular as shown in FIG. 7B. The shape is stable as long as it remains in its martensite phase. When the martensitic phase of the fastener 401 of FIG. 7A is implanted into the body and brought to body temperature, the fastener will deform back to its original austenitic shape of FIG. 7B, thereby shortening along the length of bellows 440. It will also bend through angle U along the length of the bellows so that the bones of the phalanx can be compressed and fused at the resulting angle V. In the martensite phase, angle U=V. The angularities provided by bellows 440 is at least between 1° to 15°, preferably between 1° to 20°, more preferably between 1° to 45°, and most preferably between 1° to 60°. Also, as shown in the third and fourth embodiments, the first and second embodiments and all others that follow the present embodiment may be angular in design to allow a joint to be fused in a position other than straight.

As shown in FIG. 7B, during the austenitic transformation, or phase change to austenite, each of the angles at opposing outer bendable interconnector portions 452A and 452B, and each of the angles at opposing inner bendable connector portions 454A and 454B, will become more acute (smaller) but the angular change will cause a greater acuteness, i.e., a smaller, sharper angle, to these angles at bendable interconnector portion 452B and bendable connector portion 454B on the shorter side of the accordion-like bellows 440 in its austenite state. This is illustrated in FIG. 7B by the acute angles T1" and T2" at interconnector portion 452B and connector portion 454B, respectively, relative to the larger acute angles T1' at bendable interconnector portion 452A and the larger acute angle T2' at bendable connector portion 454A on the longer side of this accordion-like bellows. It follows that the deformation in transitioning from the austenite phase to the martensite phase causes more tension in the 452B and 454B junctures than in the 452A and 454A junctures.

As an example, the plurality of zigzag elements of the bellows 440 may add up to form six folds 425 as shown in FIGS. 7A and 7B. In the martensite phase of FIG. 7A, each of the angles T1 and T2 formed respectively at the bendable interconnectors 452 and the bendable connectors 454 may for instance be 60°. Referring now to FIG. 7B, if the application of the fastener requires a 6° angulation to the fastener, then as the bellows 440 goes through its austenitic transformation into its austenite phase, the bellows portion will not only contract in length but also change angles T1', T1" and T2', T2" at the interconnector portions 452A and 452B and connector portions 454A and 454B, respectively, such that the plurality of angles T1" and T2" go through a total angle change greater by at least about 6° than the total angle change in the plurality of angles T1' and T2'. Thus, the T2" angle between each fold 425 and the T1" angle within each fold 425 may change by 0.5° more than the T1' and T2' angle changes to cause a total angle change difference of 6° across the length of the bellows 340 such that fastener angles V and U become 6°. This total angle change difference is approximate and assumes that there is a 0.5° charge difference between upper and lower portions of the bellows end faces 422 and 423 that define an acute angle as aforesaid. Alternatively, one fold may have a difference change between T1', T2' and T1", T2" of 0.5° and an adjacent fold may have a difference change of 1.5°, but ultimately adding up to 6° acres the plurality of folds. Alternatively, only one fold may change by the full 6° to create the needed total change angles U and V.

Operation of Fourth Embodiment

The joint surfaces are prepared as before for the first embodiment shown in FIGS. 4A-4D. Proximal phalanx 42 and middle phalanx 46 are surgically prepared as before as shown in FIGS. 4A-4D h Here abutment surface 78 of proximal phalanx 42 and abutment surface 74 of middle phalanx 46 are prepared so they are at an angle to the long axis of each phalanx respectively. If the surgeon or user wants to fuse the two bones at ten degrees, for instance, then the cut surfaces must be prepared so that the angle formed between the long axes of proximal phalanx 42 and middle phalanx 46 equals ten degrees when both cut surfaces are placed end to end. For example, one surface could be cut at zero degrees or perpendicular to the long axis of the phalanx while the surface of the other phalanx is cut at ten degrees. Alternatively, both phalanges could be cut equally at five degrees. The surgeon will need to choose the implant that is designed to bend ten degrees.

If the surgeon wants to fuse the two bones at fifteen degrees, then she or he would have to prepare the cut surfaces to equal fifteen degrees total angulation. For example, one surface could be cut at zero degrees or perpendicular to the long axis of the phalanx while the surface of the other phalanx is cut at fifteen degrees. Alternatively, both phalanges could be cut equally at seven and one-half degrees and the surgeon would need to use an implant designed to bend fifteen degrees.

After the respective cut surfaces are prepared, each phalanx is then counter-bored preferably to equal depths as in the first embodiment and the implant is then inserted into each phalanx as previously described. The middle and proximal phalanx are then manually held pressed together while fastener 401 goes through its shape change. Herein again barbs 460 deploy and expand outward, being embedded into the surrounding bone. Bellows 440 also goes through its shape change and shortens axially to draw the cut faces of the middle and proximal phalanx toward each other and to bring and compress together these surfaces of the proximal and middle phalanx. Simultaneously, bellows 440 bends along the length of the bellows to position the phalanxes in an angled arrangement. Referring again to FIG. 7B, folds or pleats 425 change their angles T1' and T1" at their bendable interconnector portions 452A and B, respectively, and their angles T2', T2" at their bendable connector portions 454A and B, respectively, angles T1" and T2" becoming more acute than angles T1' and T2'.

Fifth Embodiment

Although the structural details of the accordion section and the anchoring members may differ, the fifth embodiment has the same functional features as described for the first embodiment and as shown best in FIG. 2C. However, the fifth embodiment includes some substantial differences relative to the previously described embodiments. FIGS. 8A through 8F show a fastener 501 wherein an accordion-like section in the form of a bellows 540 again has an end face 522 and an end face 523. Extending axially from end faces 522 and 523 are male connectors or couplers 514 and 515, respectively. Male connector 515 is compromised of a sleeve 517 fixedly attached to an end face 523 of the according section. Male connector 514 is comprised of a sleeve 516 fixedly attached to an end face 522 of the accordion section.

As shown best in FIG. 8B, the accordion-like bellows section 540 is comprised of a series of contiguously connected zigzag elements 542, 542' to form a pleat or fold like structure 525 of the accordion like bellows. Herein, a first leg-like zig segment 553 extends radially inward relative to the non-central longitudinal axis LA5 and a first leg-like zag segment 555 extends radially outward relative to the longitudinal axis LA 5, and these two segments are joined at an acute angle S1 by a first inner bendable connector or juncture 554 to form a first zigzag element 542. A second zigzag element 542' is formed adjacent to the first element 542 by a second zig segment 553' joined to a second zag segment 555' by a second inner bendable connector 554'. First element 542 is joined at an acute angle S2 to the adjacent second zigzag element 542' by an outer bendable interconnector 556 to form a series of contiguously connected zigzag elements 542, 542'. Thus, connectors 554, 554' on the one hand, and interconnector 556 on the other hand, are angled connectors that face in opposite directions and are fixedly interconnected to the segments joined thereby.

Each bendable connector or interconnector joining any zig and zag segments forms either an acute angle S1 or an acute angle S2, angles S1 and S2 preferably being equal. An end zag segment 551 extends radially inward from the first zigzag element 542 to join this element and henceforth the bellows section of the fastener to an end of male connector 515 opposite an integral ring 504. Zag segment 551 forms the end face 523 of the bellows, and an end zig segment 557 extends radially inward to an end of male connector 514 opposite an integral ring 503 to form the end face 522 of the bellows.

Alternatively, the zigzag structure of bellows 540 can be considered as a series of alternating zig and zag segments joined by a series of alternating outward and inward or upper and lower bendable connectors. As further alternatives, each zigzag element can be considered as formed by two leg-like segments joined to form a bendable connection. A single folder or pleat 525 is subsequently formed by two leg-like segments or a zig segment joined by a bendable connector to a zag segment. The acuteness (sharpness) of angles S1 and S2, as described for similar angles in the prior embodiments, can increased to provide a smaller acute angle when the accordion-like section of the fastener transforms from the martensite phase to the austenite phase upon a change in temperature, or the acuteness of angles S1 and S2 can decrease to provide a larger acute angle when deformed while in the martensite phase. Again, the total number of folds in this and all of the other embodiments can vary from one or two, to 10 or more, or to a hundred or more, depending on the demands required of the fastener and is not limited to what is shown in the drawings. Also, as shown in the third and fourth embodiments, the present embodiment and all others that follow may be angular in design to allow a joint to be fused in a position other than straight.

Passing axially down the center axis of fastener 501 through male connectors 514 and 515 and thus sleeves 516 and 517 is a cannulation 530 to again accommodate guide wire 43. Except for being at opposite ends of the bellows section 540, connectors 514 and 515 are essentially identical. As best shown in FIGS. 8A and 8D, male connector 514 is formed as a hollow cylindrical tube or sleeve 516 which extends axially from end face 522 of bellows 540. As shown in FIG. 8D, flaring or extending radially outward from the end of sleeve 516 opposite its attachment to end face 522 is a collar 519 forming integral ring 503. A similar collar 520 is formed by an integral ring 504 on sleeve 517 as best seen in FIG. 8C.

The sleeve 516 has two cross-cuts along its length to form four slots 506 passing through and extending from ring 503 along sleeve 516 a substantial distance towards end face 522. Four sections of a spring collet are thus formed out of male connector 514 wherein the sections of the collet can be compressed together towards the center axis of sleeve 516 and will spring back to their original position with removal of any compressive force. Male connector 514 can then be used to couple the closed accordion like bellows 540 to a female connector or coupling 549 integrally formed as the proximate end portion of a threaded anchoring means or member 550, as best seen in FIGS. 8A and 8B. Anchoring member 550 is used twice in this embodiment in that, for the operation of the embodiment, one member 550 is positioned at one end of bellows 540 and a second anchoring means or member 550' is used at the opposite end of bellows 540. Anchoring member 550, 550' may be made from shape memory metal though it is not absolutely necessary because they need not undergo any change in its shape. Therefore they may be made from a material that is compatible with the shape memory alloy to avoid any corrosion and should also be biocompatible for implantation into a human or animal body. For instance, if bellows 540 is made from a nickel-titanium shape memory alloy, then member 550, 550' may be of titanium and therein fit the aforementioned criteria. Member 550, 550' could also be made from a biocompatible polymer that may or may not be bio-absorbable.

Figure 8C:
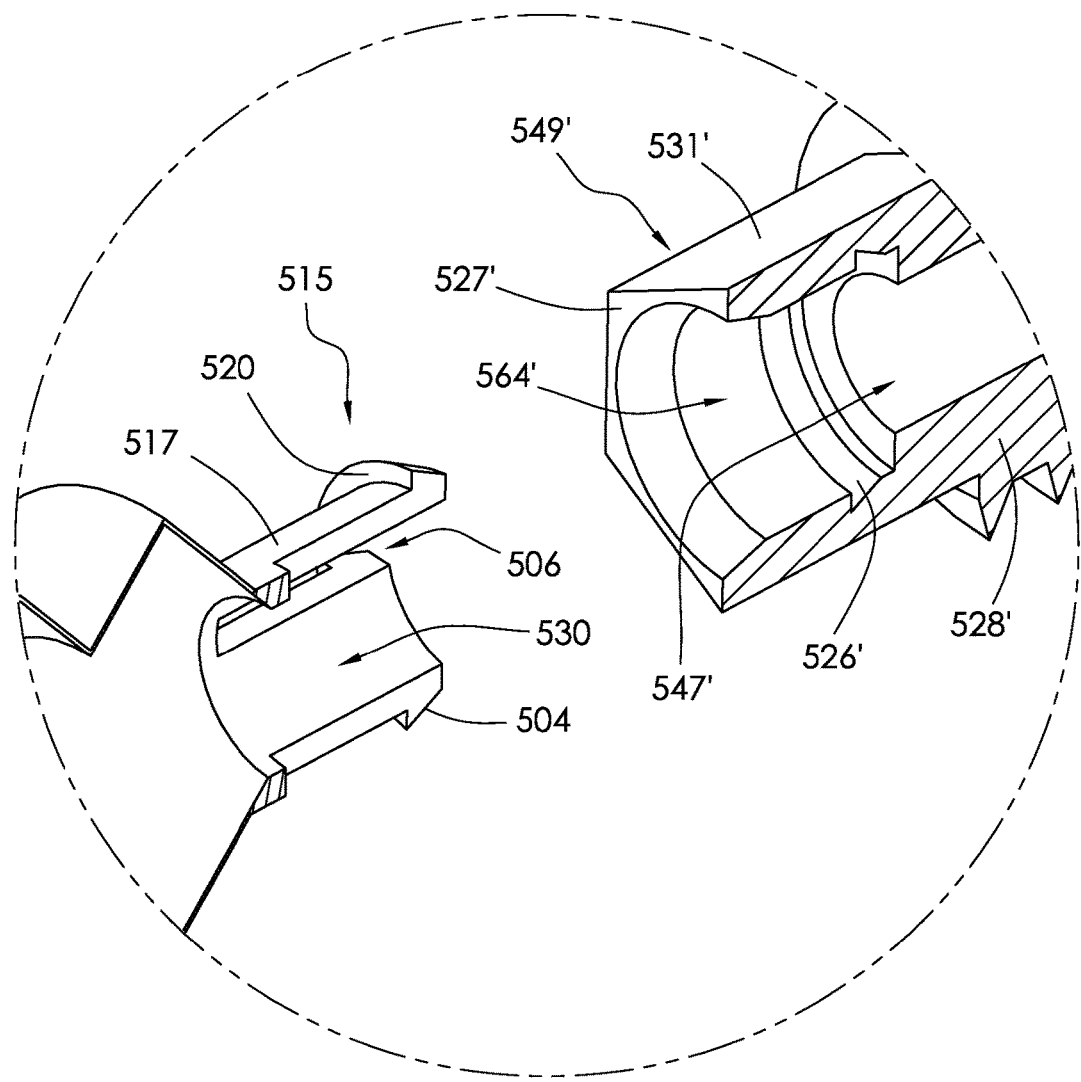
FIG. 8C is an enlarged profile perspective and cut-away view showing details of the coupling mechanism for joining one end of the bellows to the proximal end of one of the screws of FIG. 8B.
Figure 8D:
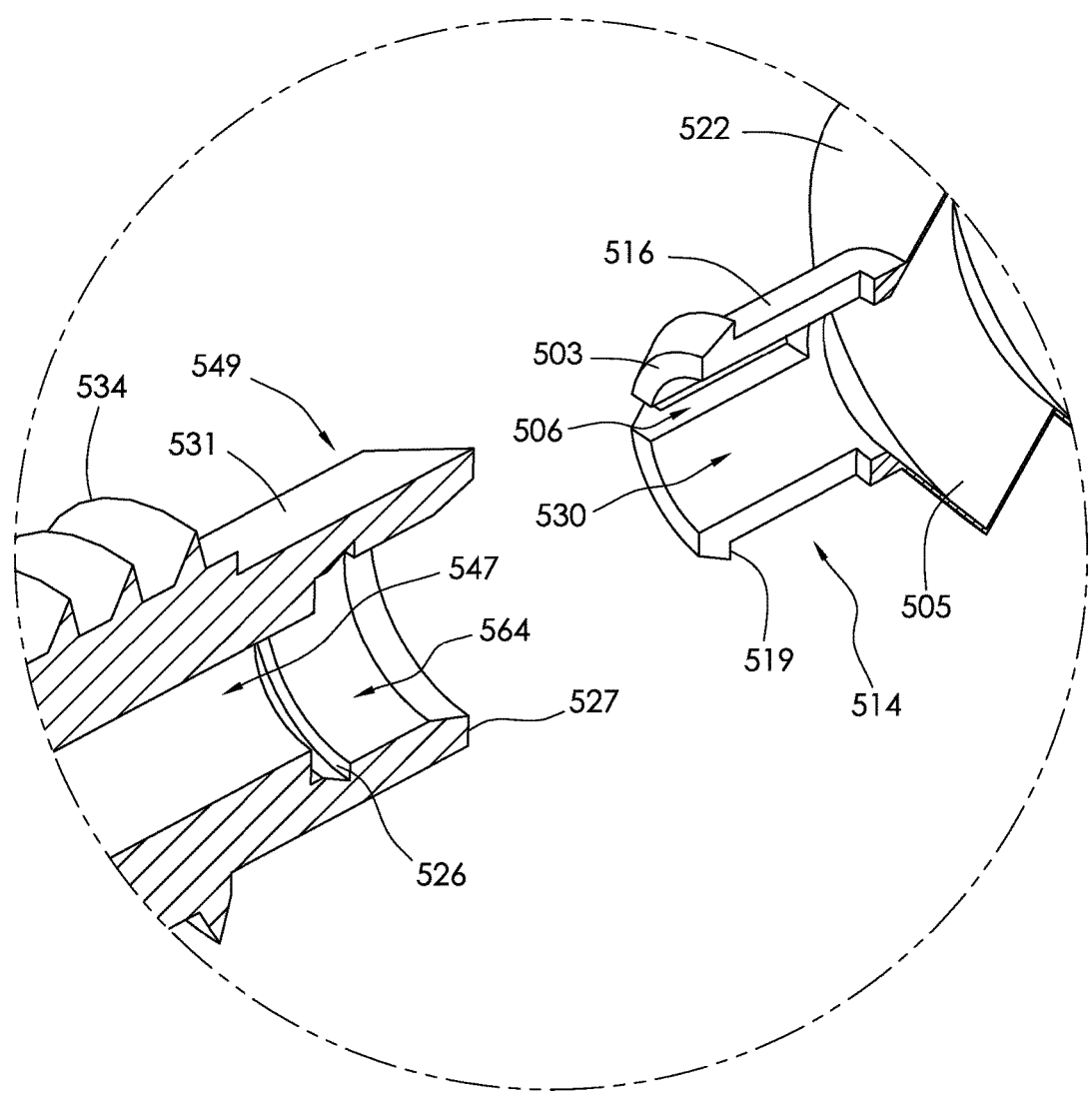
FIG. 8D is an enlarged profile perspective and cut-away view showing details of the coupling mechanism for joining the other end of the bellows to the proximal end of the other screw of FIG. 8B.

As shown best in FIGS. 8A-8C, each member 550, 550' has a tubular body 528, 528' and its female connector 549, 549' has an end face 527, 527'. Male connector 515 is used to couple bellows 540 to member 550' by engaging female connector 549', female connector 549' being the proximate end portion of member 550'. As shown in FIGS. 8C and 8D, a central longitudinal cylindrical cavity 564, 564' extends longitudinally into female connector 549, 549' through the end face 527, 527'. Passing axially through body 528, 528' is a cannulation 547, 547', as seen best in FIGS. 8A through 8D, to allow passage of guide wire 43. Cavity 564, 564' has an internal diameter and length to accommodate male connectors 514 and 515. Again referring to FIGS. 8C and 8D, to allow for coupling to occur, cavity 564 has a circular recess 526 set radially around its inner wall. It is positioned and extends substantially along the circumference of the wall of the cavity opposite end face 527, 527'. Collars 519 and 520 will, respectively, snap into recess 526, 526' when male connectors 514 and 515 are inserted forcefully into cavity 564, 564'. Upon insertion of male connectors 514 and 515 into cavity 564, 564', the internal wall of these cavities will maintain the sections of the spring collets compressed together until collars 519 and 520 reach recess 526, 526'. Thereat, rings 503 and 504 seat themselves into recess 526 locking together the bellows 540 and the two threaded members 550.

Bellows portion 540 and male connectors 514 and 515 are generally all made from the shape memory metal, although the male connectors themselves are not cold deformed and therefore do not undergo a shape memory change.

There is motion across the male connectors when the spring collet is compressed by the internal diameter of anchoring member 550 but this is due to force applied on the spring collet and not action of the shape memory metal. However, collars 519 and 520 could be designed to change shape. For example, the collar could be designed such that in the austenite phase, the collar is angled or bent axially in the direction of bellows 540. In the martensite phase, the collar would be in a position where it is angled axially away from the bellows. Then, upon implantation into the body and warming of the metal, phase change from martensitic back to austenitic would cause collars 519 and 520 to change its shape. This would cause the collars to bend or angle back toward their original positions, directed substantially in the direction of the bellows. When bellows 540 is coupled to member 550, the phase change in the collar would help to further pull together the two devices, adding to the compression provided by the fastener.

Figure 8E:
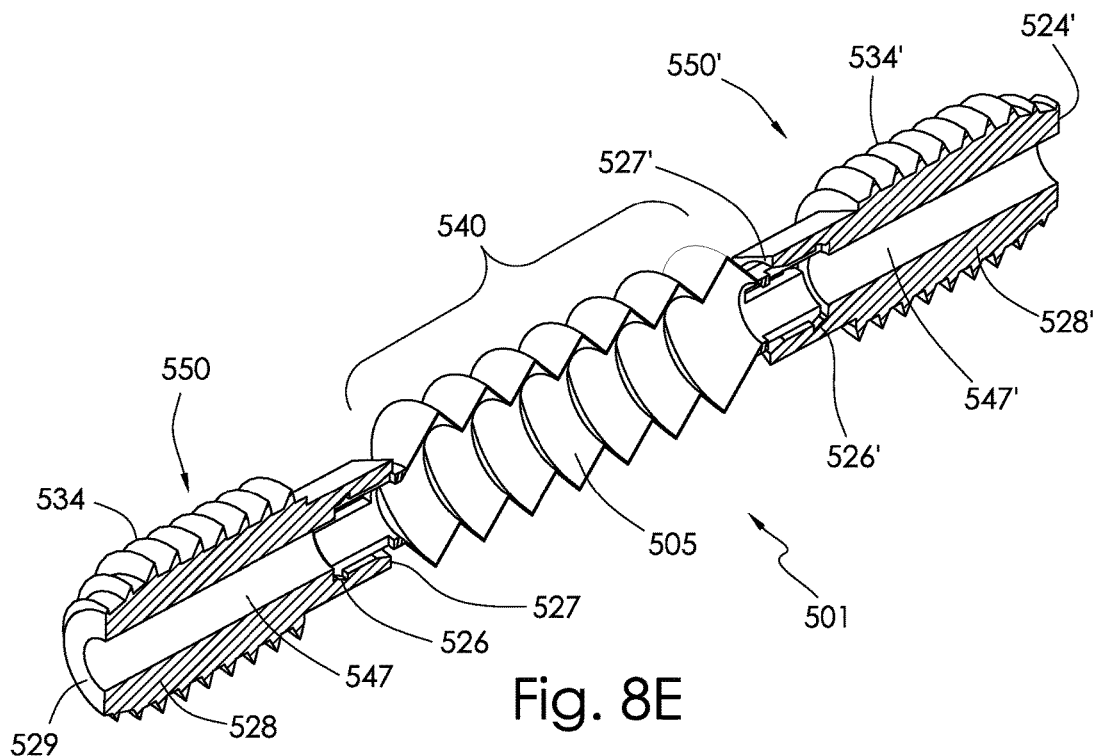
FIG. 8E is a perspective cut away view showing the alternative embodiment of the fastener of FIG. 8A in its martensitic phase with each end of the bellows-like portion joined to a screw.

When each anchoring member 550 and bellows 540 are coupled together, cannulation 547 are axially aligned with a bellows chamber 505 as shown best in FIGS. 8B, 8D and 8E. FIGS. 8A, 8C, 8D, and 8F show the female connectors 549 having an outer hexagonal shape that functions as a tool receiving surface 531 for engagement by a tool such as a hexagonal shaped screw driver Tool receiving surface 531 extends axially away from anchoring member 550, forming the outer periphery of female connector 549, and ends substantially away from member 550 at end face 527. Tool receiving surface 531 has a hexagonal cross-sectional shape in this embodiment, although square, star-shaped, torx, or cruciate cross sectional shapes would also be acceptable as these are other common shapes for screwdrivers available in an operating room. In this embodiment with the hexagonal shaped tool surface 531, a screwdriver (not shown) with a hexagonal receptacle may be slid over surface 531 for the purposes of turning member 550 axially into a bone. Member 550 includes a thread or plurality of threads 534, 534' spiraling around each body 528 and extending the length of body 528 from a terminal surface 529, 529' at one end of each body 528 to the juncture where each female connector 549 fixedly attaches to body 528 opposite each terminal end 529. These threads are for anchoring member 550 into a middle or proximal phalanx. As stated earlier, member 550 does not go through a shape change and therefore does not necessarily need to be made from a shape memory metal.

However, member 550 can be made from a shape memory metal which would allow some modifications of the anchoring method into bone. For instance, instead of body 528 having threads 534, the body could have barbs, similar to the prior embodiments, that expand when implanted into a proximal or middle phalanx or other substrate. Male connector 514 of bellows 540 would then be inserted into cavity 564 and coupled with member 550, effectively achieving the same goal. Other anchoring methods could be used as well. Two different types of screws could be used or two members that are only differentiated by the thread patterns going in opposite directions. One screw would be screwed into the bone clockwise, the other counterclockwise. Furthermore, as alternatives to these designs, bellows 540 can be made in a similar angular manner as that shown for bellows 340 in FIG. 6A or bellows 440 of FIG. 7B.

Other coupling arrangements besides the spring collet design could also be used to join together anchoring member 550 and bellows 540. A strike-and-latch type coupling mechanism or push-lock mechanism could be employed in the design as well for any of the embodiments hereinafter described. Also, although the male couplings 514 in 515 and the female coupling 549 are not designed to be detachable after being joined, other coupling arrangements designed to be detachable after joinder are well known in the coupling art. In addition, the coupling mechanisms of other coupling arrangements could have shape memory capabilities as described above for the collars 519 in 520 on the spring collets of this embodiment.

Operation of Fifth Embodiment

As seen in FIGS. 4A and 4B, the joint surfaces of proximal phalanx 42 and middle phalanx 46 are again prepared as previously described for the first embodiment. The cut surfaces 78 and 74 are prepared so that their surfaces are perpendicular to the long axis of the bones. Herein again guide wire 43 is driven axially into proximal phalanx 42 using wire driver 38. A counter-borer or drill, as in the first embodiment in FIG. 4C, that matches the thread root diameter of member body 550 is placed over guide wire 43 and used to make matching bore holes in proximal phalanx 42 and middle phalanx 46. The counter-borer is removed from the guide wire. Member 550 is then placed over guide wire 43 followed by a screwdriver (not shown) having a hexagonal shaped cannulation. This screwdriver is then mated with tool surface 531, shown best in FIG. 8A, and then member 550 is screwed into proximal phalanx 42 to appropriate depth. A similar procedure is then performed on middle phalanx 46 and a second member 550 is screwed into middle phalanx 46.

Figure 8F:
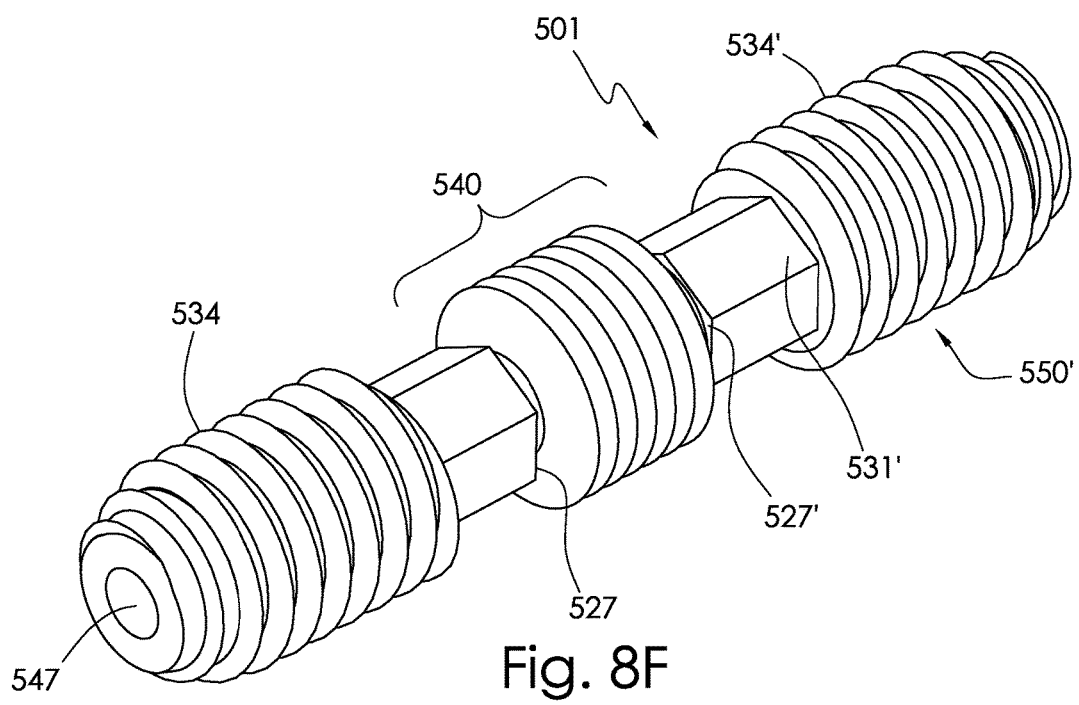
FIG. 8F is a profile perspective view of the embodiment of FIG. 8A showing the bellows-like portion in its austenite phase with each end of the bellows joined to a screw.

Refrigerated bellows 540 is now manually implanted into the proximal phalanx 42 and the middle phalanx 46 per the following. Male connector 514, again shown best in FIGS. 8A and 8D, is pushed into cavity 564. The spring collet is compressed by the walls of cavity 564 until collar 519 of ring 503 slips into recess 526, locking male connector 514 and bellows 540 to member 550. Proximal phalanx 42 and middle phalanx 46 are grasped by the surgeon's hands, just as in the main embodiment, and male connector 515 is manually inserted into cavity 564 of the second member 550 in middle phalanx 46. Collar 520 of ring 504 snaps into recess 526 locking together bellows 540 and the second member 550. At this point, bellows 540 is connected on both its ends to a member 550 in proximal phalanx 42 and a member 550 in middle phalanx 46. FIG. 8F shows fastener 501 as assembled with bellows 540 situated between each anchoring means or members 550 and coupled together with them. The fastener is shown here in its austenite phase with bellows 540 contracted and shortened, while FIG. 8E shows bellows 540 in its martensite phase, elongated by deformation.

Figure 9:
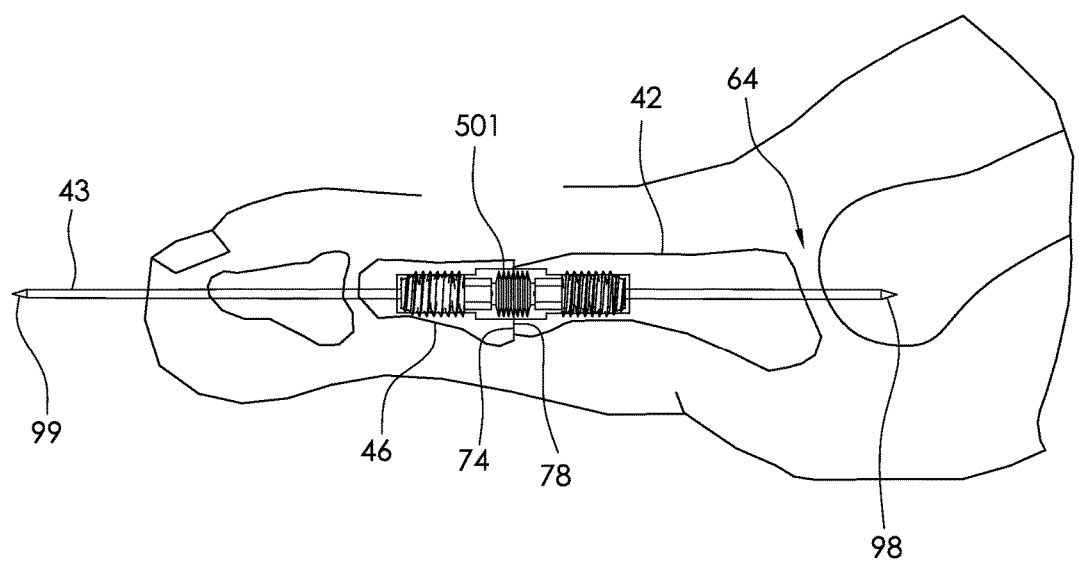
FIG. 9 is a side elevation view of the alternative embodiment of FIG. 8F showing the fastener implanted into a proximal interphalangeal joint. The bellows is in its austenitic shortened phase with a guide wire implanted through the toe and into the metatarsal, passing through the cannulation of the fastener.

As the temperature of shape memory bellows 540 increases to body temperature, it undergoes a change in shape from its annealed elongated martensite phase to its shortened austenite phase, drawing together surface 78 of proximal phalanx 42 and surface 72 of middle phalanx 46. In so doing, as shown in FIG. 8B, acute angle S1 and acute angle S2 become more acute (smaller). Also, leg-like zig segment 553 and leg-like zag segment 555, as well as corresponding segments along the length of bellows 540, draw closer together through the shape changes in those segments and in the bendable connectors 554' and 554, as well as in the corresponding bendable interconnections 556 along the length of bellows 540. After the two surfaces become compressed, the surgeon may then decide whether he or she needs to place proximal end 98 of guide wire 43 across MTPJ 64, and leave it within fastener 501, or remove guide wire 43 entirely from the fastener and the toe. Wire driver 38 is used to place the guide wire in the appropriate position. After removal of the guide wire, the surgeon then closes the wound utilizing a standard surgical technique. FIG. 9 shows fastener 501 implanted into a PIPJ and in its austenite phase.

Sixth Embodiment

Figure 10:
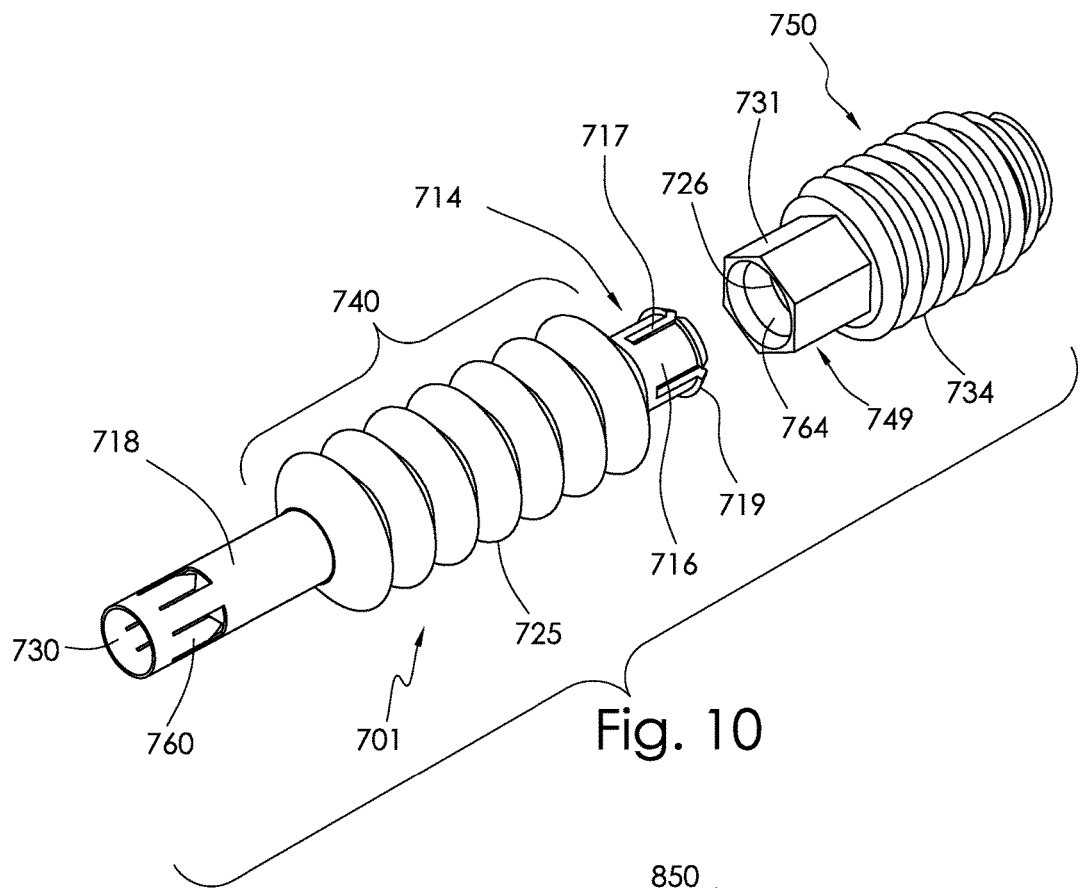
FIG. 10 is an exploded profile perspective view of a sixth embodiment of the fastener showing two separated component parts of the embodiment. There is a central accordion-like bellows portion and one end of the bellows portion has an integral sleeve with barbs for fastening into bone. The other end of the bellows portion has a coupling mechanism for attaching to a screw for implanting into bone.

A sixth embodiment is shown in FIG. 10 wherein this embodiment shows combinations of components of the previous embodiments. Although the structural details of the accordion section and the anchoring members may differ, the sixth embodiment has the same functional features as described for the first embodiment and as shown best in FIG. 2C. Herein, a fastener 701 has a sleeve 718 which extends axially outward from an accordion like section in the form of a bellows 740. Accordion section 740 is made up of zigzag elements that again form a fold-like structure as previously described in prior embodiments. A plurality of anchoring means or barbs 760 are substantially positioned outward from the bellows along the length of sleeve 718. Extending axially outward from accordion section 740 opposite sleeve 718 is a male connector 714 as described in the previous embodiment. A cannulation 730 passes along the internal central axis of the sleeve and bellows. An anchoring means or member 750 is the same as described in the fourth embodiment. Member 750 may be made from a shape memory metal alloy, shape memory polymer, or other biocompatible alloy or polymer. Again, spiraling circumferentially around member 750 is a plurality of threads 734 for screwing anchoring member 750 into bone or another substrate. Female connector 749 again has a hexagonal tool receiving surface 731 to seat a similarly shaped hexagonal screwdriver.

Male connector 714 has similar design and makeup as male connectors 514 and 515 from the fifth embodiment as shown in FIG. 8A-8F. Male connector 714 again has two cross-cuts 717 down its length to form four sections of a spring collet 716. A collar 719 is beset opposite bellows 740 at the end of male connector 714 and collar 719 engages the internal diameter of an anchoring means or member 750, as described for the fifth embodiment, when the male connector 714 is inserted into a cavity 764. Herein, collar 719 snaps into a recess 726 inside the female connector 749. The collar may have shape memory action as previously described or may be made without it and the collar and the entire male connector may or may not be made from shape memory materials. The action of the male connector is likewise the same as previously described for the fifth embodiment. Here again the coupling mechanism of this embodiment need not be based on a spring collet design. A strike and latch mechanism or a push-lock mechanism, either one with or without shape memory action, could be employed to achieve coupling of screw member 750 to bellows 740 of the fastener 701. Also, as shown in the third and fourth embodiments, the present embodiment and all others that follow may be angular in design to allow a joint to be fused in a position other than straight.

Operation of Sixth Embodiment

In using fastener 701, the bones of a toe are prepared as previously described in FIGS. 4A and 4B. Here again a guide wire 43 is driven axially into proximal phalanx 42 using a wire driver 38. A counter-borer 88, as in the first embodiment in FIG. 4C, that matches the thread root diameter of member 750 is placed over guide wire 43 and used to make a bore hole 11 in proximal phalanx 42. The counter-borer is removed from the guide wire. Member 750 is then placed over guide wire 43 followed by a hexagonal or appropriately shaped screwdriver or socket drive to fit over hexagonal shaped tool surface 731 of member 750. This screwdriver is then mated with tool surface 731 and then member 750 is screwed into proximal phalanx 42 to appropriate depth. Next the guide wire is placed into middle phalanx 46 and a counter-borer is used to create a matching bore hole 12 in abutment surface 74 of the middle phalanx.

The chilled martensite phase accordion like bellows 740 is now manually implanted into the proximal phalanx 42. Male connector 714 is pushed into cavity 764 of member 750. The spring collet is compressed by the walls of cavity 764 until collar 719 slips into recess 726 (not shown) of member 750, locking male connector 714 and bellows 740 to member 750. Proximal phalanx 42 and middle phalanx 46 are grasped by the surgeon's hands, just as in the main embodiment, and sleeve 718 of the fastener is slid into matching bore hole 11 in middle phalanx 46. The two abutment surfaces are brought together and the bellows is warmed by body heat. This allows the bellows and the barbs to change shape. The barbs expand radially outward into the surrounding bone and the bellows contracts axially by angular changes in the zigzag elements of the bellows as described in prior embodiments to compress the abutment surfaces together.

Seventh Embodiment

Figure 11:
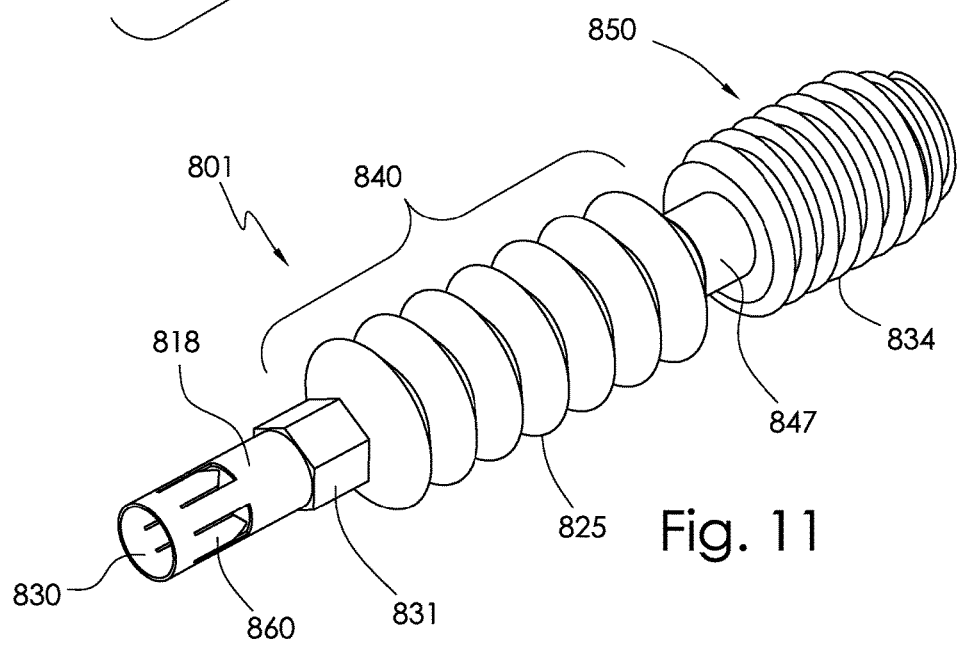
FIG. 11 is a profile perspective view of a seventh embodiment similar to that of FIG. 10 but showing a single piece construct with integral sleeves. The central accordion-like bellows portion has an integral screw at one end as a means for implanting and securing the fastener into bone and the opposite end has an integral sleeve with barbs for anchoring the fastener into another bone.

FIG. 11 shows a seventh embodiment where again there is a single construct for implantation into bone. A fastener 801 is shown having components of the previous embodiments and is generally tubular. A bellows 840 is again centrally positioned along a longitudinal axis of fastener 801 and is comprised of a plurality of folds or pleats 825, again created by repeating zigzag elements formed by a series of zig segments connected to zag segments by bendable connectors and interconnected by bendable interconnectors as described in previous embodiments. Thus, although the structural details of the accordion section and the anchoring members may differ, the seventh embodiment has the same functional features as described for the first embodiment and as shown best in FIG. 2C.

Extending axially outward away from bellows 840 is again an integral sleeve 818 with a plurality of anchoring means or barbs 860. Extending axially outward away from bellows 840 and substantially in the opposite direction of sleeve 818 is an anchoring means or screw member 850 Member 850 has a plurality threads 834 spiraling inward from a terminal end 829 substantially toward bellows 840. Member 850 is similar in shape and design as that of the prior two embodiments. In this embodiment, however, screw member 850 is fixedly attached to bellows 840 either directly or via a small tubular or cylindrical arm 847 situated between the bellows 840 and member 850. Again, sleeve 818, bellows 840, arm 847, and member 850 are all generally axially aligned and there is a longitudinal central cannulation 830 extending the length of the entire fastener as noted in the first embodiment. Situated substantially opposite barbs 860 and adjacent bellows 840, sleeve 818 is modified into a tool receiving surface 831 where sleeve 818 joins bellows 840. Tool surface 831 is generally hexagonal shaped to allow a hex screwdriver or socket drive to slide over sleeve 818 and engage the tool surface. A screwdriver or socket drive may then be used to turn the entire fastener 801 to first drive screw member 850 end first into a bone.

Being a single construct, the entire fastener 801 is preferably made of a shape memory alloy though it is still possible that screw member 850 could be made of a non-shape memory metal like titanium. As with embodiments one to six above, an angularity could be imparted to this seventh embodiment so that the bones to be fused are set at an angle to one another. Also, the entire construct need not necessarily be entirely made up of shape memory metal or polymer as long as the parts of the embodiment needing to undergo a shape change are made of shape memory material. As previously indicated, when the fasteners described above change shape from an extended state to a contracted state upon being heated, they are considered to be heat responsive and may be referred to as heat responsive fasteners. The screw part and the bellows part could be integral or instead made independently and then welded together to form a single construct. Again, this embodiment may also be made angularly instead of straight as set forth in prior embodiments. Conceivably the sleeve end of fastener 801 could be made as a separate piece from bellows 840. A coupling arrangement as previously described, say a spring collet mechanism, a push-lock mechanism or a strike and latch mechanism, could then be used as a way of joining together the barbed sleeve 818 and bellows 840 with its attached screw member 850 after both segments of the embodiment have been separately implanted into the bones to be fused.

Operation of Seventh Embodiment

In using fastener 801, the bones of a toe are prepared as previously described in FIGS. 4A and 4B. Here again a guide wire 43 is driven axially into proximal phalanx 42 using a wire driver 38. The counter-borer 88 matches the thread root diameter of member body 850 It is placed over guide wire 43 and used to make a bore hole 11 in proximal phalanx 42. The counter-borer is removed from the guide wire. Fastener 801 is then placed over guide wire 43 followed by a screwdriver having a hexagonal shaped cannulation to fit over the tool surface 831 of fastener 801 This screwdriver is then mated with tool surface 831 and the entire fastener 801, not just body 850, is screwed into proximal phalanx 42 to appropriate depth. Next the guide wire is removed and placed into middle phalanx 46 and a counter-borer is used to create a matching bore hole 12 in abutment surface 74 of the middle phalanx that will match the half of fastener 801 that encompasses sleeve 818 and barbs 860. Proximal phalanx 42 and middle phalanx 46 are grasped by the surgeon's hands, just as in the main embodiment, and sleeve 818 of the fastener is slid into matching bore hole 12 in middle phalanx 46. The two abutment surfaces are brought together and the bellows is warmed by body heat. This allows the bellows and the barbs to change shape. The barbs expand radially outward into the surrounding bone and the bellows contracts axially to compress the abutment surfaces together.

Eighth Embodiment

Figure 12:
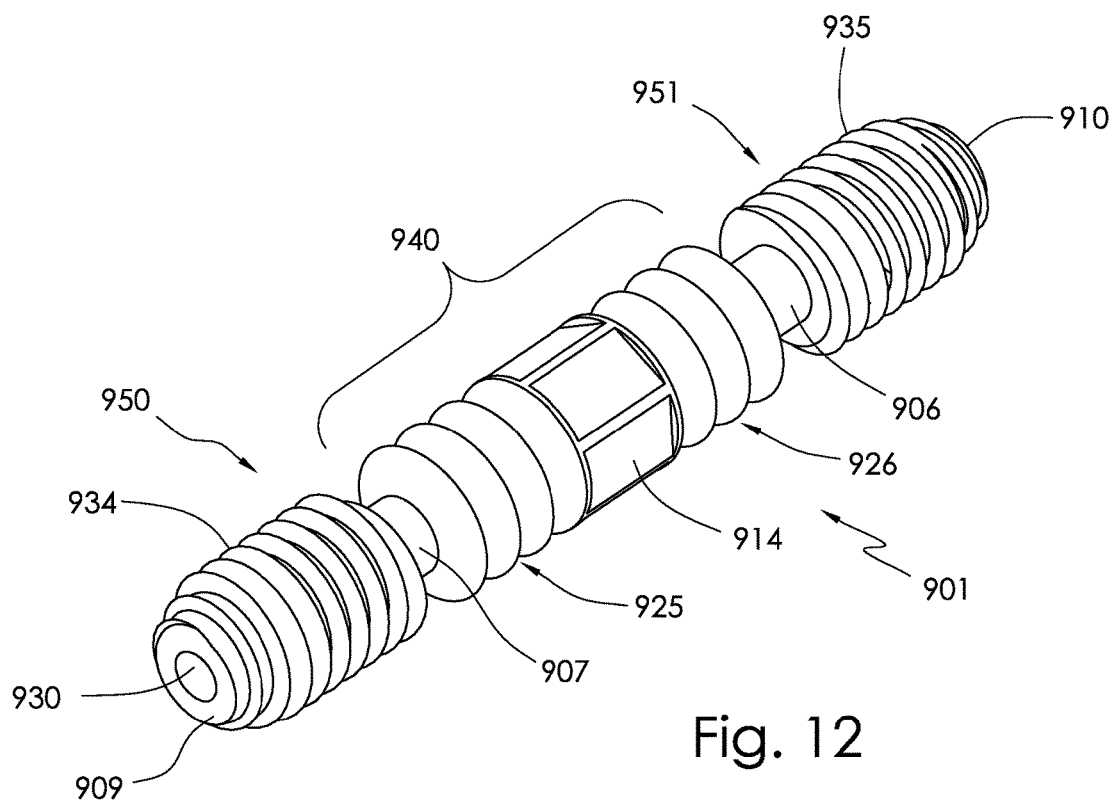
FIG. 12 is a profile perspective view of an eighth embodiment of the fastener showing a single piece construct wherein the central bellows portion of the fastener is integrally connected at each end to a screw. One screw has right hand turning threads while the other screw has left hand turning threads.

FIG. 12 shows an eighth embodiment similar in appearance to the fifth embodiment. The most notable differences in a fastener 901 are a first anchoring means or member 950 and a second anchoring means or member 951 fixedly attached to each end of a bellows 940 wherein members 950 and 951 have oppositely handed thread patterns to each other. Member 950 has an end face 909 on the end of the member 950 substantially opposite the centrally positioned bellows 940. A plurality of threads 934 spiral axially inward from end face 909 and surrounds the periphery of screw member 950. Threads 934 are left hand turning in their operation. A set of threads 935 spiral axially inward from an end face 910 and surrounds the periphery of member 951. Threads 935 are right hand turning in their operation. A cylindrical or tubular arm 907 fixedly joins member 950 to bellows 940 and a cylindrical or tubular arm 906 fixedly joins member 951 to bellows 940. Member 950, arm 907, bellows 940, arm 906, and member 951 are all axially aligned.

Fastener 901 has a cannulation 930 running centrally down the long axis of the fastener for passage of a guide wire as in prior embodiments. The cannulation extends from end face 909 of member 950 to end face 910 of member 951. Bellows 940 is again comprised of a series of zig segments and zag segments joined by bendable connectors to form zigzag elements which create a pleated or fold-like structure 925, these zigzag elements in turn being fixedly joined in series by bendable interconnectors to form the bellows section. Thus, although the structural details of the accordion section and the anchoring members may differ, the eighth embodiment has the same functional features as described for the first embodiment and as shown best in FIG. 2C.

The central pleat of bellows 940 is modified into a hexagonal shaped tool receiving surface 914, or hex nut, dividing the bellows in half. One half portion of the bellows is integrally connected to one side of the hex shaped tool receiving surface 914 whereas the other half portion of the bellows is integrally connected or fixedly joined to the opposing side of the hex shaped tool receiving surface. Alternatively, the hex tool receiving surface 914 could be omitted from the bellows portion and instead be fixedly attached to the end of member 950 or 951 effectively replacing either arm 907 or 906 respectively. It would then serve as a replacement for arm 907 or 906

Bellows 940 is again preferably made entirely of a shape memory material but those parts that do not undergo shape change do not necessarily need to be. Since the tool surface 914 does not undergo a change in its shape, it could be made from an alternative biocompatible alloy or metal and the two halves of the bellows may be welded to it. Members 950 and 951 also could be made from a metal or alloy other than a shape memory alloy since this portion of the embodiment also need not undergo a shape change. These too could be welded to the bellows directly or via arms 907 and 906. As with the previously described embodiments, when the bellows changes shape from an extended state to a contracted state upon being heated, the fastener is considered to be heat responsive and may be referred to as a heat responsive fastener.

Though FIG. 12 represents an embodiment where members 950 and 951 are solidly attached, a mechanism could conceivably be used for detachably coupling the screws to the bellows. Here a strike and latch coupling mechanism may be appropriate or some similar design such that the coupling mechanism permits the transfer of torque to member 950 and 951, described below in the operation of fastener 901 If the screws are not integral to the bellows, then they could be made from a biocompatible polymer which could again be detachably coupled to the bellows 940. Furthermore, members 950 or 951 could be fixedly attached but encompass a ratcheting or one-way rotation capability of the entire fastener when turned one direction but only one member turns when the fastener is turned in the opposite direction. This would effectively allow the fastener to be screwed into a proximal phalanx, and when insertion is complete, reversing the direction of screwing motion of a screwdriver would allow the distal end of the fastener to screw into a middle phalanx due to the opposite turning threads between the proximal member 950 and distal member 951 of the fastener and an associated ratcheting mechanism would prevent the member in the proximal phalanx from backing out.

Operation of Eighth Embodiment

Placing the embodiment across the PIPJ for joint fusion is not unlike the prior embodiments. The joint surfaces are again prepared as before. A guide wire and counter-borer are again used in the proximal phalanx and a matching bore hole is made. Again, one end of fastener 901 is slid over the guide wire in the proximal phalanx and placed inside the phalanx. The guide wire is then removed and directed into the middle phalanx and out the end of the toe. A matching bore hole is then made in the middle phalanx. The middle phalanx is then slid over the other end of the fastener and the guide wire allowed to slide down cannulation 930. Once the fastener is in position spanning the joint space, the design and operation of the embodiment is such that the hexagonal tool surface is centrally aligned over the joint space with the screws and bellows inside the bones. There is some space or gapping between the abutment surfaces of the proximal and middle phalanx. A hex shaped wrench is then placed over the hex tool surface 914 and used to turn the fastener. This transmits torque to members 950 and 951 such that, coupled with the action of the left and right hand screws, turning the fastener in only one direction drives both of the screws into the respective bones thereby embedding them therein and anchoring them into the phalanges. This then draws the proximal and middle phalanx closer together. The hex wrench is then removed and the shape change of bellows 940, upon warming up in response to body heat, completes the process of drawing and compressing together the opposing abutment surfaces of the proximal and middle phalanx. Subsequently the surgeon may then decide whether to drive the guide wire across the MTPJ, leave it where it is, or remove it altogether prior to closure of the surgical wound.

Alternatively, if tool surface 914 is instead fixedly attached to an end face 909 and arm 907 has a built-in ratcheting mechanism, then fastener 901 could be implanted into boreholes 11 and 12 of the proximal and middle phalanx and a hex driver could be slid over the guide wire at the PIP joint level and coupled over the tool surface 914. The tool receiving surface could be of other shapes as well if fixedly attached to end face 909. Hex, cruciate, star or torx shaped tool receiving surfaces could be employed. Fastener 901 could be turned and member 951 is screwed into the proximal phalanx. Member 950 of the fastener could then be inserted into the middle phalanx and hex screwdriver slid over the guide wire through the distal phalanx into the middle phalanx onto a tool receiving surface 914 fixedly attached to the end of member 940. By turning member 950 in the opposite direction that member 951 was turned, member 950 could be screwed into the middle phalanx without simultaneously turning bellows 940 and member 951. This could be done through a ratcheting mechanism of arm 907 if so incorporated.

Ninth Embodiment

Figure 13C:
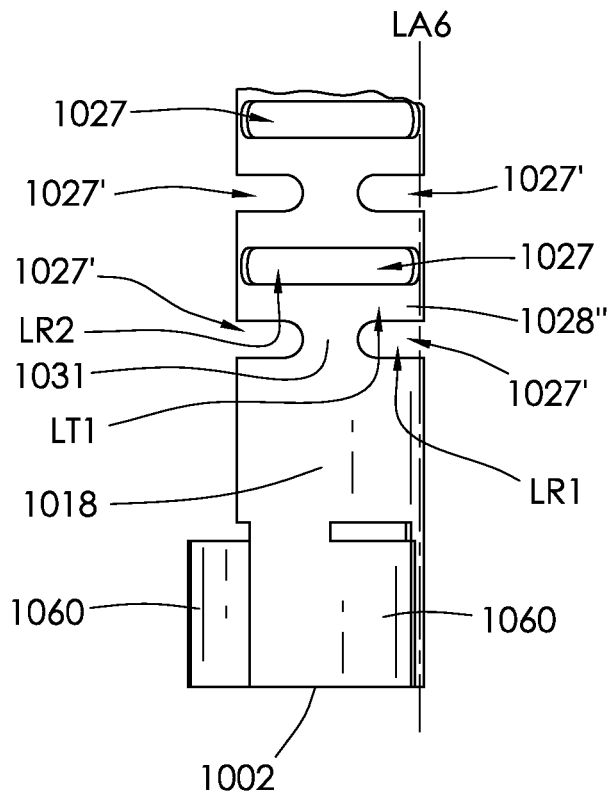
FIG. 13C is a top profile view of one end of the fastener embodiment of FIG. 13B showing details of the structure in the austenite phase. The view shows the barbs of the embodiment expanded outward and the accordion section in its shortened state.

A ninth alternative embodiment, as shown in FIGS. 13A-13D, reveals another variation of the bellows section of the invention, as well as a variation on the previously described barbs. FIGS. 13A and 13B show a fastener 1001 wherein the shape of a contractible accordion section 1040 has been modified to an "open" accordion-like section. Although the structural details of the accordion section and the anchoring members differ, the ninth embodiment has the same functional features as described for the first embodiment and as shown best in FIG. 2C.

Figure 13D:
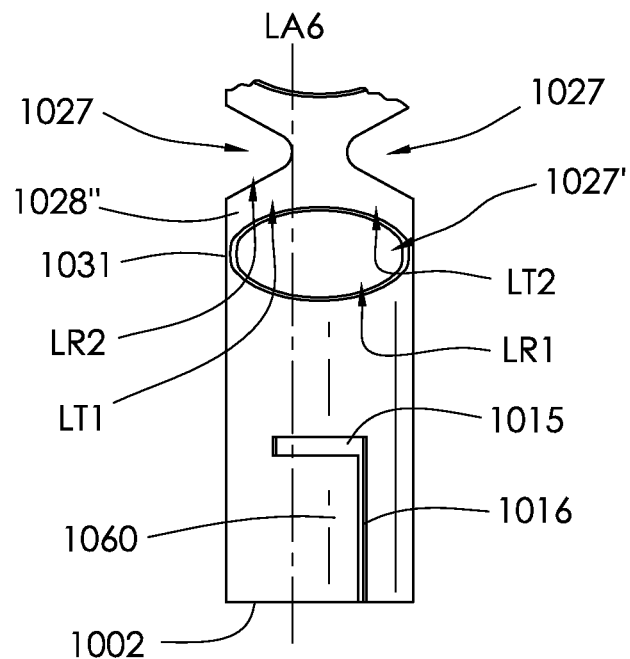
FIG. 13D is a side profile view of one end of the fastener embodiment of FIG. 13A showing details of the structure in the martensitic phase with the accordion section extended by deformation and the barbs lying flush by deformation to the surface of the fastener. This view shows the embodiment from a 90 degree angle relative to the view of FIG. 13C.

Fastener 1001 is shown in its extended martensite phase in FIG. 13A and in its contracted austenite phase in FIG. 13B. Fastener 1001 has a terminal end 1002 and a terminal end 1003 as in prior embodiments. Terminal ends 1002 and 1003 are generally tubular and constitute the very ends of the fastener similar to other embodiments. Extending axially inward from terminal ends 1002 and 1003 are elongated tubular sleeves 1018 and 1019, again as in prior embodiments. Cut within the surfaces of sleeves 1018 and 1019 and extending inward from terminal end 1002 are a plurality of first anchoring means or barbs 1060, which again serve to anchor the fastener within the pieces to be connected. Extending inward from terminal end 1003 is a plurality of second anchoring means or barbs 1060'. The anchoring barbs shown here are in a different shape from prior embodiments to show that they can be any of a number of shapes or designs, both inclusive and exclusive of the other embodiments, and are not limited to what is described herein. In this instance, as shown in FIG. 13A, the barbs are designed via an L-shape cut 1017 into sleeves 1018 and 1019. FIG. 13D shows one end of a fastener 1001 in its martensite phase wherein a long arm 1016 of the L-shaped cut extends substantially inward from terminal end 1002 axially along the sleeve. A short arm 1015 is a continuation of the long arm, set at a right angle or any other angle, to the fastener's long axis and the long arm 1016. Both arms are cut full thickness through the wall of fastener 1001 into a central cannulation 1030, seen in FIGS. 13A and 13B. Cannulation 1030 extends through the fastener from the terminal end 1002 exiting the opposite terminal end 1003. This embodiment shows three barbs 1060, best seen in FIG. 13B, at each end of the fastener, but other pluralities would be acceptable. FIGS. 13A and 13D show barbs 1060 substantially flush with the external periphery of the martensite fastener 1001. FIGS. 13B and 13C show the austenite fastener with the barbs 1060 having opened radially outward from the central axis of the fastener.

Substantially further inward along fastener 1001 from terminal ends 1002 and 1003, and set between sleeves 1018 and 1019 lies the "open" contractible accordion section 1040. In this embodiment, a zigzag element 1004 and a zigzag element 1004' lie within the circular surface of the tubular cylindrical wall of the fastener. A first leg-like zig segment 1026 extends spirally in the martensite phase and semi-circumferentially in the austenite phase toward a non-central longitudinal axis LA6. A first leg-like zag segment 1028 spirals in the martensite phase and semi-circumferentially in the austenite phase outward and away from the longitudinal axis LA6. These two segments are joined at an acute angle R1 by a first inner bendable connector 1025 to form a first zigzag element 1004. A second zigzag element 1004' is formed by a second zig segment 1026' joined to a second zag segment 1028' by a second inner bendable connector 1025', first zigzag element 1004 being joined at an acute angle R2 to the adjacent second zigzag element 1004' by an outer bendable interconnector 1029. Thus, inner bendable connectors 1025 and 1025' on the one hand, and outer bendable interconnector 1029 on the other hand, are angled connectors that face in opposite directions and are fixedly interconnected to the segments joined thereby. Also, each bendable connection joining any zig and zag segments forms either an acute angle R1 or an acute angle R2, angles R1 and R2 preferably being equal. A zag segment 1028" also constitutes an end segment that is fixedly attached to sleeve 1018 by way of a final bendable interconnector 1031 at one end of section 1040. Zig segment 1026 also constitutes an end segment that is fixedly attached to end sleeve 1019 by way of a final bendable interconnector 1031' at the other end of section 1040.

Alternatively, the zigzag structure of open accordion section 1040 can be considered as a series of alternating zigzag elements joined by a series of alternating outward bendable interconnectors and inward bendable connectors relative to the non-central long axis LA6. As further alternative, each zigzag element can be considered as joined together with an adjacent zigzag element to form a bendable interconnection. Thus, a series of contiguously connected zigzag elements extending from sleeve 1018 to sleeve 1019 can be considered as a longitudinal tier LT1 forming a multiple fold-like wall structure of the open accordion section 1040. A second series of contiguously connected zigzag elements constitutes a second longitudinal tier LT2 forming a second multiple fold-like wall structure of accordion section 1040. Longitudinal tier LT1 and longitudinal tier LT2 each have the appearance of out of phase sine waves that are stacked semi-circularly around the circumference of the accordion section 440, wherein the series of bendable connectors joining the zig and zag segments of longitudinal tier LT1 is fixedly joined to the series of bendable interconnectors joining the zigzag elements of longitudinal tier LT2. Third and fourth longitudinal tiers (not shown) are similarly stacked semi-circularly around the circumference of the accordion section 1040 with each tier being out of phase or out of sync with any single adjacent tier. For example, longitudinal tier LT1 is out of phase with longitudinal tier LT2 (as well as out of phase with a fourth longitudinal tier that is not shown, but would be in phase with a third longitudinal tier that is not shown).

In an alternative description, the fold-like wall structure of longitudinal tier LT1 is inverted relative to the fold-like wall structure of longitudinal tier LT2, and the inverted longitudinal tiers are joined in back-to-back fashion to each other along the bendable connectors. The combination of circumferentially stacked and fixedly joined longitudinal tiers defines a plurality of apertures arranged in a plurality of longitudinal rows, such as apertures 1027' in row LR1 and apertures 1027 in row LR2. In this embodiment, four longitudinal rows of apertures are defined by the four longitudinal tiers of the accordion section 1040. As seen best in FIGS. 13B and 13C, the apertures 1027' of longitudinal row LR1 are offset 90° to the apertures 1027 of longitudinal row LR2. The apertures of a third longitudinal row (not shown) are 180° to longitudinal row LR1. Any one aperture preferentially has an aperture opposite thereto by 180° circumferentially across the fastener.

FIG. 13A again shows the fastener in its extended martensite phase. More importantly, it shows the accordion like section 1040 stretched or elongated by deformation. Angles R1 and R2 are preferentially equal in the martensite phase. As the accordion section goes through the austenitic transformation and contracts from its elongated position in FIG. 13A, angles R1 and R2 will become more acute, and will still be preferentially equal as seen best in FIG. 13B.

All embodiments, including this ninth embodiment, can incorporate any of the design features of previous or subsequent embodiments, including but not limited to angular changes in body shape and variations in plurality, shape or operation of the accordion section or of the barbs or other anchoring means, such as using threaded ends to the fastener instead of barbs.

Operation of Ninth Embodiment

The operation of the ninth embodiment is the same as the first embodiment of FIGS. 2A-2C. Implantation is identical to the first embodiment. A guide wire is again used in the phalanges for alignment and positioning of the fastener and bore holes again drilled into the bones. Thereafter, the implant is imparted first into the proximal phalanx and then aligned on the guide wire that rests within the middle phalanx. The guide wire is then slid down cannulation 1030, best seen in FIGS. 13A and 13B, as fastener 1001 is imparted into the bore hole 12 in the middle phalanx. The cut surfaces of the middle and proximal phalanx are manually held together by the surgeon while the fastener changes phases and further compresses the surfaces together. In FIG. 13A the fastener is in an elongated martensitic phase, the phase it would be in just prior to insertion into the body or other substrate. Barbs 1060 lay substantially flush with the outer perimeter of the fastener. Upon implantation into a substrate and warmed, phase change occurs to the implant from the martensite state to the austenite state, which is seen in FIG. 13B and FIG. 13C. Barbs 1060 open and expand outward in radial fashion as an anchoring means to embed themselves into the surrounding substrate or bone. Also during the phase change, each angle R1, R2 along the length of the accordion section will become more acute as the accordion section contracts via angular change of the bendable connectors drawing a zig segment closer to an adjacent zag segment. This will subsequently narrow the width of the apertures 1027 as the fastener goes through austenitic transformation.

Tenth Embodiment

Figure 14A:
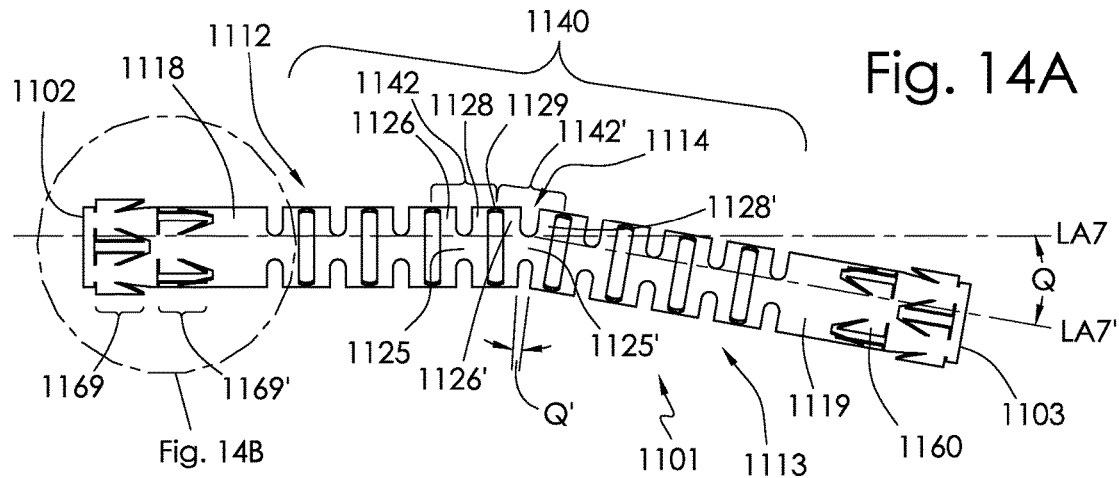
FIG. 14A is a profile view of a tenth embodiment showing a single piece construct similar to that of FIG. 13B but wherein the fastener has a shape set angled open accordion portion shown in its contracted shortened austenite phase. Herein the barbs of the integral sleeves are deployed outward and are of different design than previously described.
Figure 14B:
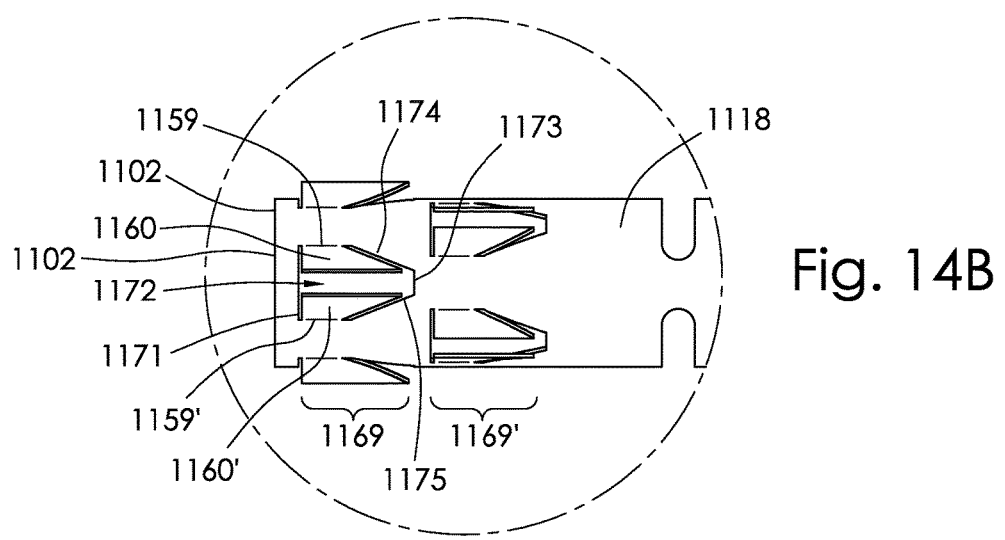
FIG. 14B is an enlarged profile view of one end of the embodiment of the fastener shown in FIG. 14A detailing the barbs of the fastener deployed outward in their austenite phase.

FIGS. 14A and 14B show a tenth embodiment. As shown in FIG. 14A, a fastener 1101 has an open accordion structure similar to that shown in the ninth embodiment of FIGS. 13A and 13B, but here the fastener goes through a shortening or contraction during its transition from the martensite phase to the austenite phase and at the same time an angular change occurs. Fastener 1101 again has a generally straight tubular body in the martensite phase, similar to that shown in the ninth embodiment of FIG. 13B, but takes on an angled tubular body in its austenite phase as shown in FIG. 14A. The description of the zigzag elements of the accordion section 1140 has been given previously in the description of the accordion section 1040 of the embodiment of FIGS. 13A-13D. Also, although the structural details of the accordion section and the anchoring members may differ, the tenth embodiment has the same functional features as described for the first embodiment and as shown best in FIG. 2C.

Fastener 1101 has a terminal end 1102 and a terminal end 1103 and beset substantially inward from the terminal ends are a sleeve 1118 and a sleeve 1119, respectively. As shown in FIG. 14A, and detailed in FIG. 14B, sleeves 1118 and 1119 have a plurality of barbs 1160 fixedly attached and arranged around the circumference of the sleeves. Seen best in FIG. 14B, this tenth embodiment shows a plurality of anchoring means or barbs 1160 in two circumferential courses or rows 1169 and 1169', the courses being staggered in relationship to one another circumferentially around sleeves 1118 and 1119. Each course has four sets of barbs, each set having a pair of barbs 1160 and 1160'. The arrangement shown could allow for any plurality of barbs and these figures show sixteen barbs in eight sets at each end of the fastener. Adding more or less rows could substantially increase or decrease the total number of barbs and therefore affect the holding power of the implant in bone or other substrate. Here the barbs and fastener are shown in the deployed austenite phase. FIG. 14B shows details of barbs 1160 and 1160' which have not been described previously in this application. This shows an alternative system for anchoring the fastener into a surrounding substrate and could be used on any other embodiment just as any other barb or screw design could be used on this embodiment of the fastener. They are all interchangeable and not mutually exclusive. Different barb designs or anchoring systems can be used on the same fastener either at the same end or opposite ends of the fastener depending on the needs of the application.

Referring again to FIG. 14B, beset substantially inward from terminal end 1102, a plurality of transverse linear cuts 1171 is made full thickness through the wall of sleeve 1118. This transverse cut extends part way around the circumference of the sleeve and this embodiment shows two columnar stacked rows with each row having four transverse linear cuts. Intersecting the transverse linear cut at approximately its midpoint is a linear longitudinal cut 1172 that is also full thickness through the wall of the fastener. The linear longitudinal cut 1172 extends lengthwise substantially opposite terminal end 1102 towards the accordion section parallel to the long axis of the fastener. The length of linear longitudinal cut 1172 will determine the overall length of the barbs. The end of the linear longitudinal cut opposite terminal end 1102 intersects an apex 1173 of a V-shaped full thickness cut 1174. The intersection occurs at the internal aspect of the apex 1173 and the arms of the V-shape cut extend obliquely from the apex substantially back toward terminal end 1102 The intersection thus divides the V-shaped cut into two halves each forming a barb with a sharp culmination or point 1175 on each of two barbs 1160 and 1160'. The culminations 1175 point in the direction substantially opposite terminal end 1102 toward the accordion structure. In the martensite phase, barbs 1160, 1160' lie flush with the internal and external walls of the fastener. As the phase changes from martensite back to austenite, the barbs bend outward along a neck portion 1159, 1159' connecting each barb to the tubular body of the sleeve 1118. As the accordion structure 1140 changes phase and thereby draws terminal ends 1102 and 1103 towards each other, the outwardly bent culminations or points 1175 are driven into the surrounding substrate, anchoring the fastener.

As seen best in FIG. 14A, the accordion structure 1140 is like the austenite phase of the accordion structure 1040 of the fastener 1001 shown in FIG. 13B. However, here structure 1140 has been shape set or trained to not only undergo shortening for compression of the bone ends, but also to undergo an angular change from a straight or 0° angle to an angle Q. The angle change can be shape set to occur across any single one of the bendable connectors 1125, which join a zig segment 1126 and a zag segment 1128 to form a first zigzag element 1142 as shown in FIG. 14A, or could be shape set to occur across numerous consecutive or non-consecutive connectors and interconnectors along the length of the accordion section, allowing greater angles to be achieved as needed by the demands of the particular application. As in the prior embodiments of FIGS. 13A-13D, a plurality of bendable connectors join zig segments and zag segments to form a plurality of zigzag elements 1142, 1142', which are in turn are joined by a plurality of bendable interconnectors, such as a bendable interconnector 1129, to form a plurality of zigzag elements contiguously connected to form each half portion 1112, 1113 of the accordion section 1140. More precisely, a bendable connector 1125 joins a zig segment 1126 to a zag segment 1128 to form a first zigzag element 1142, and an interconnector 1129 joins the zag segment 1128 of this element to the zig segment 1126' of the adjacent element 1142' to form a plurality of zigzag elements 1142, 1142' that are contiguously connected together. The arrangement of these fixedly connected elements again forms a plurality of apertures similar to apertures 1027 in FIG. 13B.

In this embodiment, a bendable connector 1125' joins an inward zig segment 1126' (relative to a first long axis LA7 of the first portion 1112 of the accordion section 1140) to an outward zag segment 1128' (relative to a second long axis LA7' of the second portion 1113 of the accordion section 1140) to form the second zigzag element 1142'. Here, bendable connector 1125' has a bend 1114 that forms an angle Q' between zig segment 1126' and zag segment 1128' in the austenite phase of the fastener. The bend 1114 also forms an angle Q between the long axis LA7 and LA7', which is equal to angle Q' between zig segment 1126' and zag segment 1128' as connected by the bent connector 1125'. In the martensite phase, longitudinal axes LA7 and LA7' overlie each other and are synonymous lines. In the austenite phase as the fastener subtends angle Q, long axes LA7 and LA7' diverge, decreasing the acuteness (sharpness) of the angles Q and Q'.

Eleventh Embodiment

Figure 14C:
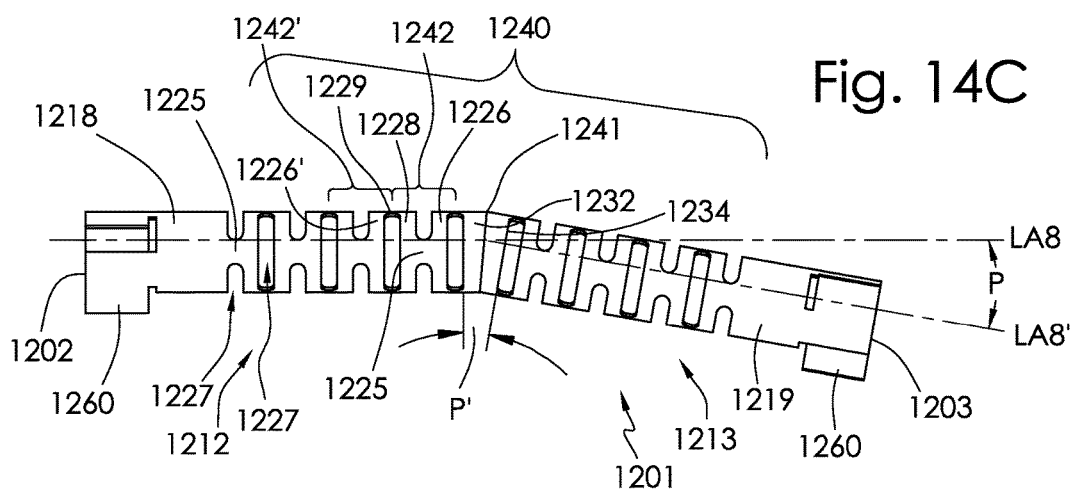
FIG. 14C is a profile view of an eleventh embodiment of the fastener somewhat similar to the embodiment of FIG. 14B and showing a single piece construct wherein a different angled open structure is shown in its shortened austenite phase. This angled design of open structure is achieved by welding together two halves of the open accordion design of FIG. 13B at an angle to each other.

An eleventh embodiment is shown in FIG. 14C wherein fastener 1201 is shown in its shortened austenite phase and again has an angled shape. Herein again, the description of the contiguously connected zigzag elements that comprise an accordion portion 1240 have been detailed in the embodiment of FIGS. 13A-13D. Also, although the structural details of the accordion section and the anchoring members may differ, the eleventh embodiment has the same functional features as described for the first embodiment and as shown best in FIG. 2C. The angled design of FIG. 14C differs slightly from that of FIG. 14A in that the two halves of fastener 1001 from FIGS. 13A and 13B are welded together end to end to form an angle P. This embodiment shows a weld 1241 placed centrally within accordion structure 1240, but could be substantially biased towards an anchoring sleeve 1218 or an anchoring sleeve 1219. Thus instead of the embodiment being shape set to take on the angled shape, fastener 1201 is manufactured by welding two halves of fastener 1001 together at an angle P.

Accordion section 1240 has a first portion 1212 with a first non-central longitudinal axis LA8 and a second portion 1213 with a second non-central longitudinal axis LA8'. Herein, an outward zag segment 1232 relative to the longitudinal axis LA8 of the first portion of the accordion section is fixedly connected at weld 1241 to an inward zig segment 1234 relative to the longitudinal axis LA 8' of the second portion of the accordion section, the two halves being joined at angle P' between these two zig and zag segments. As in the prior embodiments of FIGS. 13A-13D and 14A, bendable connector 1225 joins a zig segment 1226 to a zag segment 1228 to form a zigzag element 1242, and an interconnector 1229 joins the zag segment 1228 of this element to the zig segment 1226' of an adjacent element 1242' to form a plurality of zigzag elements 1242, 1242' contiguously connected to form each half portion of the accordion section. The arrangement of these fixedly connected elements again forms a plurality of apertures 1227. Angle P' imparts an angle P to the embodiment as represented by the longitudinal axis LA8 of a first portion of the fastener and longitudinal axis LA8' of the second portion of the fastener. Therein, the angle of the fastener is the same in both the martensite and the austenite phases. Alternative to welding them together, the embodiment could have a boss in the accordion structure similar to FIG. 6A wherein boss 314 is an angled expansion of fold 325. Fastener 1201 shows a plurality of barbs 1260 cut into integral sleeves 1218 and 1219 but remain fixedly attached to the sleeves. These barbs are similar in design and function as the barbs noted in the embodiment of FIGS. 13A and 13B.

The embodiments of FIGS. 14A and 14C can incorporate any of the designs of the previous embodiments including but not limited to an angular change in shape, variations in plurality, shape, or operation of the barbs or anchoring means, such as using threaded ends to the fastener instead of barbs.

Operation of Tenth and Eleventh Embodiment

Fasteners 1101 and 1201 are used in the same manner as fasteners 301 and 401 as shown in FIGS. 6A-7B respectively and described earlier under the second embodiment.

Twelfth Embodiment

Figure 15A:
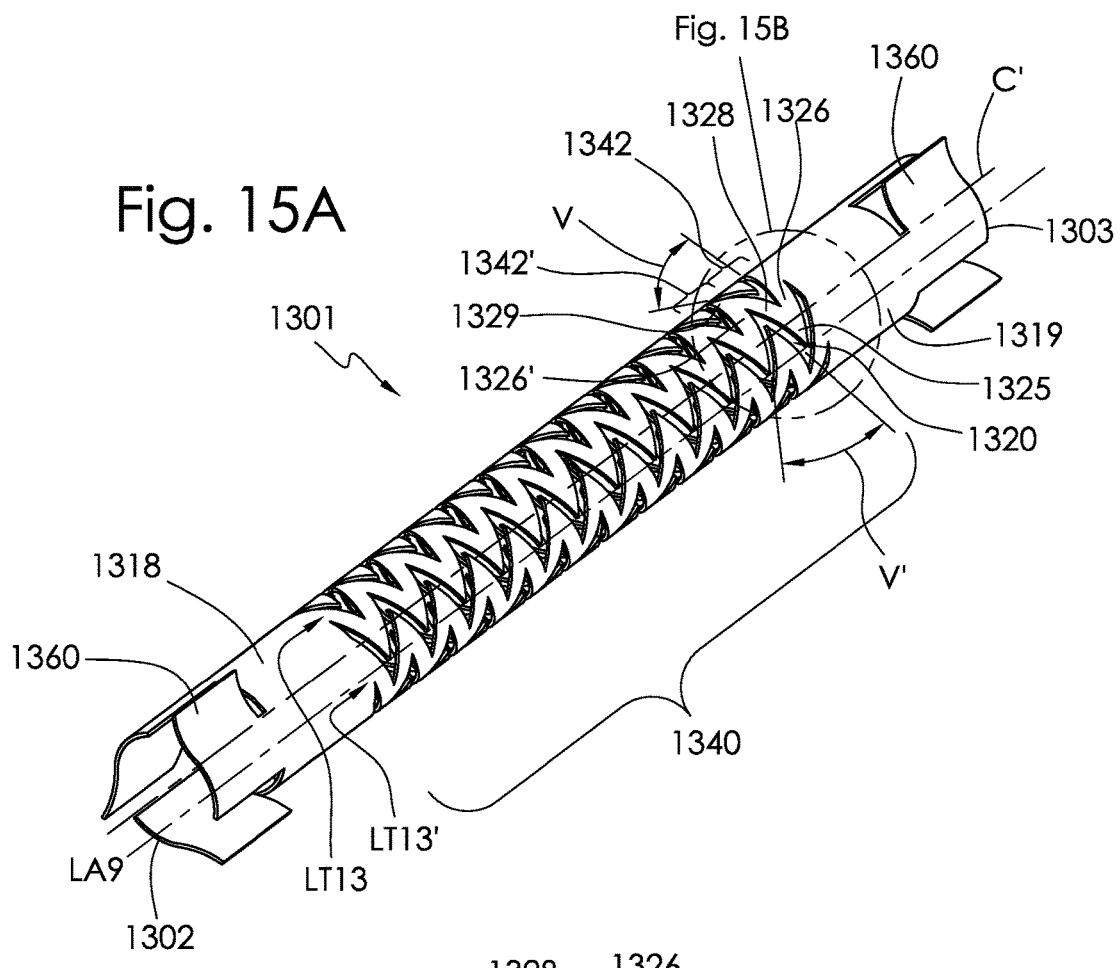
FIG. 15A is a profile perspective view of a twelfth embodiment showing a single piece construct wherein an open accordion section is shown in its contracted shortened austenite phase. The accordion section is made up of a plurality of longitudinally extending elongated zigzag openings each in the form of a series of contiguous V-shaped openings cut transversely through the wall of a tubular fastener body. The elongated opens are beset side by side and arranged in parallel around the circumference of the fastener body.

FIG. 15A shows a fastener 1301 in its shortened austenite phase in a twelfth embodiment wherein the fastener has a generally tubular body, has a terminal end 1302 and a terminal end 1303, and has a sleeve 1318 and a sleeve 1319 extending substantially inward from the terminal ends as in prior embodiments. Within sleeves 1318 and 1319 are a plurality of anchoring means or barbs 1360 similar to barbs 1060 as described previously in the embodiments of FIGS. 13A and 13B. Beset centrally between sleeves 1318 and 1319 is an alternative open accordion section 1340. Although the structural details of the accordion section and the anchoring members differ, the twelfth embodiment has the same functional features as described for the first embodiment and as shown best in FIG. 2C.

Figure 15B:
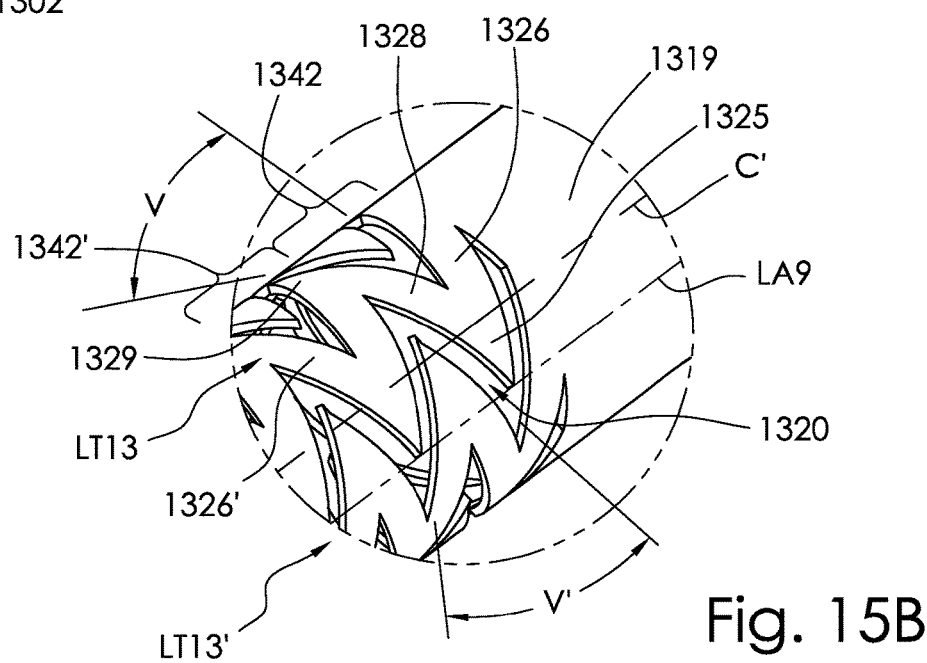
FIG. 15B is an enlarged profile view of one end portion of the embodiment of FIG. 15A showing details of the zigzag segmentation of the accordion section of the fastener in its austenite phase.

As shown in FIG. 15B, a first leg-like zig segment 1326 extends spirally inward relative to a longitudinal axis LA9 of the tubular fastener body and a first leg-like zag segment 1328 extends spirally outward relative to the longitudinal axis LA9 and these two segments are joined at an acute angle V, as shown in FIG. 15A, by an inner bendable connector or juncture 1325 to form a zigzag element 1342, as seen in FIGS. 15A and 15B. Each zigzag element 1342, as formed by zig segment 1326 joined to zag segment 1328 by inner bendable connector 1325, is joined at an acute angle V' to an adjacent zigzag element 1342' by an outer bendable interconnector 1329 to form a longitudinal tier LT13 from a series of contiguously connected zigzag elements 1342, 1342', interconnector 1329 being joined to the adjacent element 1342' via its zig segment 1326'. A second series of contiguously connected zigzag elements form a second longitudinal tier LT13'. Thus, bendable connectors 1325 and bendable interconnectors 1329 are angled connectors that face in opposite directions and are fixedly interconnected to the segments joined thereby. Inner bendable connector 1325 and outer bendable interconnector 1329 are also V-shaped connections wherein each bendable connection joining any zig and zag segments forms either an acute angle V or an acute angle V', angles V and V' preferably being equal. Zig segment 1326 is fixedly attached to sleeve 1319, as shown in FIGS. 15A and 15B.

Longitudinal tier LT13 is fixedly attached at either end by, a zig segment 1326 connected to a sleeve 1319 and a zag segment connected to sleeve 1318, as shown in FIG. 15A. Alternatively, the accordion section 1340 could be attached by a zag segment to sleeve 1319 and a zig segment to sleeve 1318, or by a zig segment to each sleeve, or a zag segment to each sleeve. Further alternatively, a single zigzag element could form the accordion section with the zig segment connected to sleeve 1318 and the zag segment connected to sleeve 1319. These alternative attachment arrangements apply to all preceding and subsequent embodiments disclosed herein. Longitudinal tiers LT13, LT13' are arranged spirally inward and spirally outward relative to longitudinal axis LA 9 in parallel around the tubular fastener body, and remaining in plane and everywhere tangent with the tubular fastener wall. This arrangement provides the shape of a spirally inward and spirally outward similarly shaped zigzag aperture 1320 along the length of the accordion section and separating one longitudinal tier LT13 from an adjacent longitudinal tiers LT13' around the fastener. Alternatively still, the zigzag structure of bellows 1340 can be considered as a series of alternating zig and zag segments joined by a series of alternating outward and inward V-shaped bendable connections. As further alternatives, each zigzag element can be considered as formed by two leg-like segments joined to form a V-shaped bendable connection The acuteness (sharpness) of angles V and V' can increase to provide a smaller acute angle when the accordion like portion of the fastener transitions from the martensite phase to the austenite phase upon a change in temperature, or the acuteness of angles V and V' can decrease to provide a larger acute angle when deformed from the austenite to the martensite phase. The plurality of zigzag elements therefore creates the plurality of folds seen in the accordion-like section of the fastener. The total number of folds can vary from one or two to hundreds or more depending on the demands required of the fastener and is not limited to what is shown in the drawings.

Thirteenth Embodiment

Figure 16:
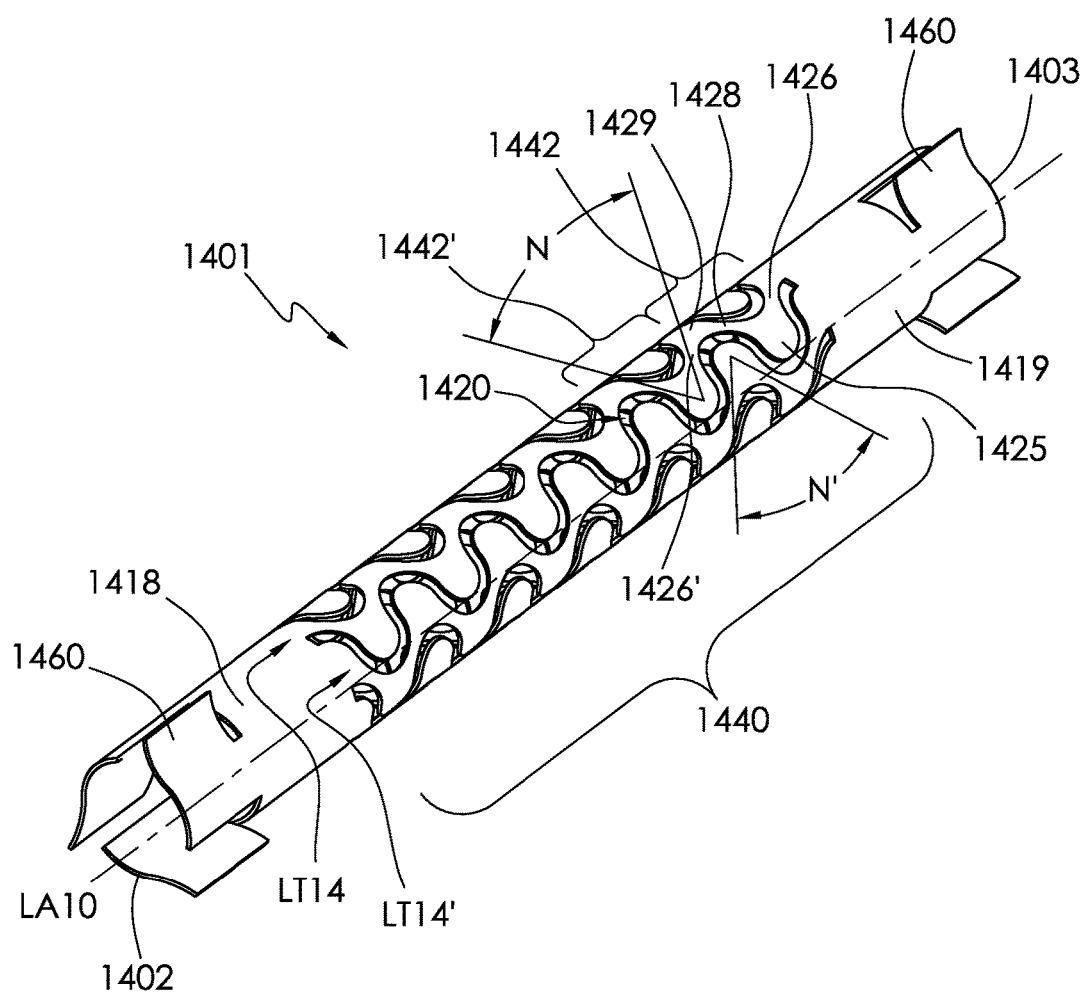
FIG. 16 is a profile perspective view of a thirteenth embodiment showing a single piece construct wherein an open accordion section is shown in its contracted shortened austenite phase. The accordion section is made up of a plurality of longitudinally extending elongated sine wave-shaped openings cut transversely through the wall of a tubular fastener body and beset side by and arranged in parallel around the circumference of the fastener body.

FIG. 16 shows a fastener 1401 in its shortened austenite phase as a thirteenth embodiment wherein the fastener has a generally tubular body, has a terminal end 1402 and a terminal end 1403, and has a sleeve 1418 and a sleeve 1419 extending substantially inward from the terminal ends as in prior embodiments. Within sleeves 1418 and 1419 are a plurality of anchoring means or barbs 1460 similar to barbs 1060 as described previously in the embodiments of FIGS. 13A and 13B. Beset centrally between sleeves 1418 and 1419 is an alternative open accordion section 1440. Although the structural details of the accordion section and the anchoring members differ, the thirteenth embodiment has the same functional features as described for the first embodiment and as shown best in FIG. 2C.

As shown in FIG. 16, a first leg-like zig segment 1426 extends spirally inward relative to a non-central longitudinal axis LA10 of the tubular fastener body and a first leg-like zag segment 1428 extends spirally outward relative to the longitudinal axis LA10 and these two segments are joined at an acute angle N by an inner bendable connector or juncture 1425 to form a zigzag element 1442. Each zigzag element 1442, as formed by zig segment 1426 joined to zag segment 1428 by inner bendable connector 1425, is joined at an acute angle N' to an adjacent zigzag element 1442' by an outer bendable interconnector 1429 to form a longitudinal tier LT14 from a series of contiguously connected zigzag elements 1442, 1442', interconnector 1429 being shown joined to the adjacent element 1442' via its zig segment 1426'. Thus, bendable connectors 1425 and bendable interconnectors 1429 are angled connectors that again face in opposite directions and are fixedly interconnected to the segments joined thereby. Inner bendable connector 1425 and outer bendable interconnector 1329 are U-shaped or sine wave shaped connections wherein each bendable connection joining any zig and zag segments forms either an acute angle N or an acute angle N', angles N and N' preferably being equal. Zig segment 1426 is fixedly attached to sleeve 1419.

Longitudinal tier LT14 is fixedly attached at either end by a zig segment 1426 connected to sleeve 1419 and a zag segment connected to sleeve 1418 as shown in FIG. 16. Alternatively, the accordion section 1440 could be attached by a zag segment to sleeve 1419 and the zig segment to sleeve 1418, or a zig segment to each sleeve, or by a zag segment or a zig segment to each sleeve. Further alternatively, a single zigzag element could form the accordion section with the zig segment connected to sleeve 1418 and the zag segment connected to sleeve 1419. Longitudinal tiers LT14, LT14' are arranged spirally inward and spirally outward relative to longitudinal axis LA10 in parallel around the tubular fastener body, and remaining in plane and everywhere tangent with the tubular fastener wall. This arrangement provides the shape of a spirally inward and spirally outward similarly shaped zigzag aperture 1420 along the length of the accordion section and separating one longitudinal tier LT14 from an adjacent longitudinal tiers LT14' around the fastener. Alternatively still, the zigzag structure of bellows 1440 can be considered as a series of alternating zig and zag segments joined by a series of alternating outward and inward U-shaped bendable connections. As further alternatives, each zigzag element can be considered as formed by two leg-like segments joined to form a U-shaped bendable connection The acuteness (sharpness) of angles N and N' can increase to provide a smaller acute angle when the accordion like portion of the fastener transitions from the martensite phase to the austenite phase upon a change in temperature, or the acuteness of angles N and N' can decrease to provide a larger acute angle when deformed from the austenite to the martensite phase. The plurality of zigzag elements therefore creates the plurality of folds seen in the accordion-like section of the fastener. The total number of folds can vary from one or two to hundreds or more depending on the demands required of the fastener and is not limited to what is shown in the drawings.

Fourteenth Embodiment

Figure 17:
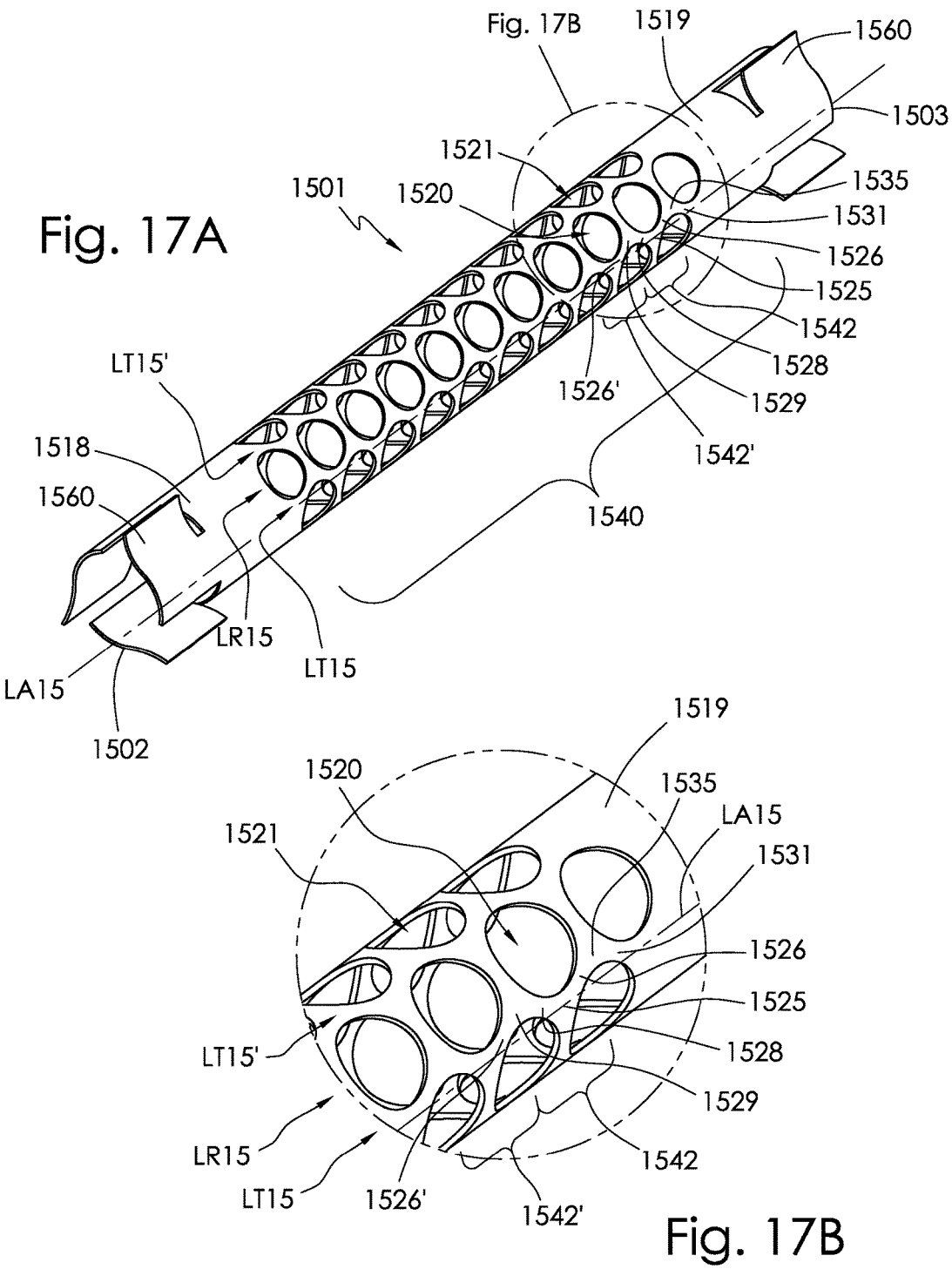
FIG. 17A is a profile perspective view of a fourteenth embodiment showing a single piece construct wherein an open accordion portion is shown in its contracted shortened austenite phase. The accordion portion is made up of a plurality of longitudinally aligned rows of circular openings cut transversely through the wall of a tubular fastener body and beset side by side, but also slightly staggered or offset to any adjacent row of circular openings to form a tessellation pattern.
FIG. 17B is an enlarged profile view of a central portion of the embodiment of FIG. 17A showing details of the accordion portion in its austenite phase.

FIG. 17A shows a fourteenth embodiment of a fastener wherein the fastener 1501 again has an elongated tubular body, has a terminal end 1502 and a terminal end 1503, and has a sleeve 1518 and a sleeve 1519 extending substantially inward from the terminal ends as in the embodiments previously described. Within sleeves 1518 and 1519 are a plurality of anchoring means or barbs 1560 similar to barbs 1060 as described previously in the embodiments of FIGS. 13A and 13B. Substantially further inward along fastener 1501 from terminal ends 1502 and 1503, and set between sleeves 1518 and 1519 lies an open accordion section 1540 shown here in its shortened austenite phase. Herein, the wall of the accordion structure 1540 has a plurality of openings or apertures 1520 defined therein and being cut full thickness through the wall of the fastener. Although the structural details of the accordion section and the anchoring members differ, the fourteenth embodiment has the same functional features as described for the first embodiment and as shown best in FIG. 2C.

As shown in FIGS. 17A and 17B, apertures 1520 are circular in the shortened austenite state instead of having an oval extended shape similar to that shown in FIGS. 13A and 13D for the ninth embodiment. However, apertures 1520 take on a different shape in the martensite phase. As the fastener is elongated by deformation and changed to its martensite phase, the circular shape of the apertures will also deform and take on a more oval or elongated circular shape. This shape will then be maintained as long as the fastener remains in martensite phase, the apertures returning to a circular shape upon implantation into the body, and heat acting as a catalyst returns the fastener to its austenite phase. A first spirally arcing leg-like zig segment 1526, as shown in FIG. 17A and further detailed in FIG. 17B, arcs spirally inward relative to a longitudinal axis LA15 of the tubular fastener body and a first arcing zag like segment 1528 arcs spirally outward relative to longitudinal axis LA15. These two segments are joined by a transversely oriented inner bendable connector 1525, to form a zigzag element 1542. Each zigzag element 1542, as formed by zig segment 1526 joined to a zag segment 1528 by a transversely oriented inner bendable connector 1525, is joined to an adjacent zigzag element 1542' by a transversely oriented outer bendable interconnector 1529 between each of the zigzag elements, interconnector 1529 being shown joined to the adjacent element 1542' via its zig segment 1526'. Thus, bendable connectors 1525 and bendable interconnectors 1529 face in opposite directions relative to the longitudinal axis LA15 and are fixedly connected to the segments joined thereby. As shown in FIG. 17B, zigzag element 1542 is joined to sleeve 1519 as a final zigzag element via an outer interconnector 1535 and a zag segment 1531, this arrangement being repeated to connect sleeve 1518 to the accordion section at the opposite end thereof. Alternatively, the zigzag structure of section 1540 can be considered as a series of alternating zig and zag segments joined by a series of alternating outward and inward transversely oriented bendable connectors. As further alternatives, each zigzag element can be considered as formed by two spirally arcing leg-like segments joined to form a bendable connection wherein the shapes of the zig segments and the zag segments and the transversely oriented bendable connectors and interconnectors fixedly attached there between form a plurality of circular apertures 1520.

Furthermore, a longitudinal tier LT15 is formed by a series of contiguously connected zigzag elements 1542, 1542', each longitudinal tier LT15 spanning the length of the accordion section and fixedly attached at either end to sleeve 1518 and 1519 by either a zig segment or a zag segment. Each longitudinal tier LT15 is fixedly attached to an adjacent longitudinal tier LT15', such that a series of these longitudinal tiers are connected circumferentially around the tubular fastener body to form the accordion section 1540. A zigzag element 1542 of one longitudinal tear LT15 is joined by its transversely oriented outer bendable interconnector 1529 back-to-back to the bendable connector of an adjacent zigzag element from an adjacent longitudinal tier, such that the zigzag elements of any longitudinal tier is out of sync, out of phase, or reversed in polarity to the zigzag element to which it is joined thereby on the adjacent longitudinal tier. The arcing zig segments contiguously connected to the arcing zag segments at the bendable connectors, and the bendable interconnectors and the connections of the zigzag elements of one longitudinal tier to the zigzag elements of an adjacent longitudinal tier, form the apertures 1520 and thereby form the tessellated pattern of the accordion section. In other words, any single longitudinal row LR15 is offset from any adjacent longitudinal row such that a diameter drawn through any aperture 1520 from any longitudinal row and passing circumferentially around the tubular fastener body will not pass through a similarly drawn diameter through any aperture 1520 from an immediately adjacent longitudinal row passing around the fastener body.

As described in prior embodiments, zig segments connected to zag segments by inner bendable connectors and zigzag elements connected to adjacent zigzag elements by outer bendable interconnectors are joined at angles such that during austenitic transformation those angles become more acute (smaller) in the austenite phase to shorten the length of the elongated tubular fastener body. This type of shortening is illustrated best in FIGS. 19B and C showing such a transformation of the sixteenth embodiment as described below.

Fifteenth Embodiment

Figure 18:
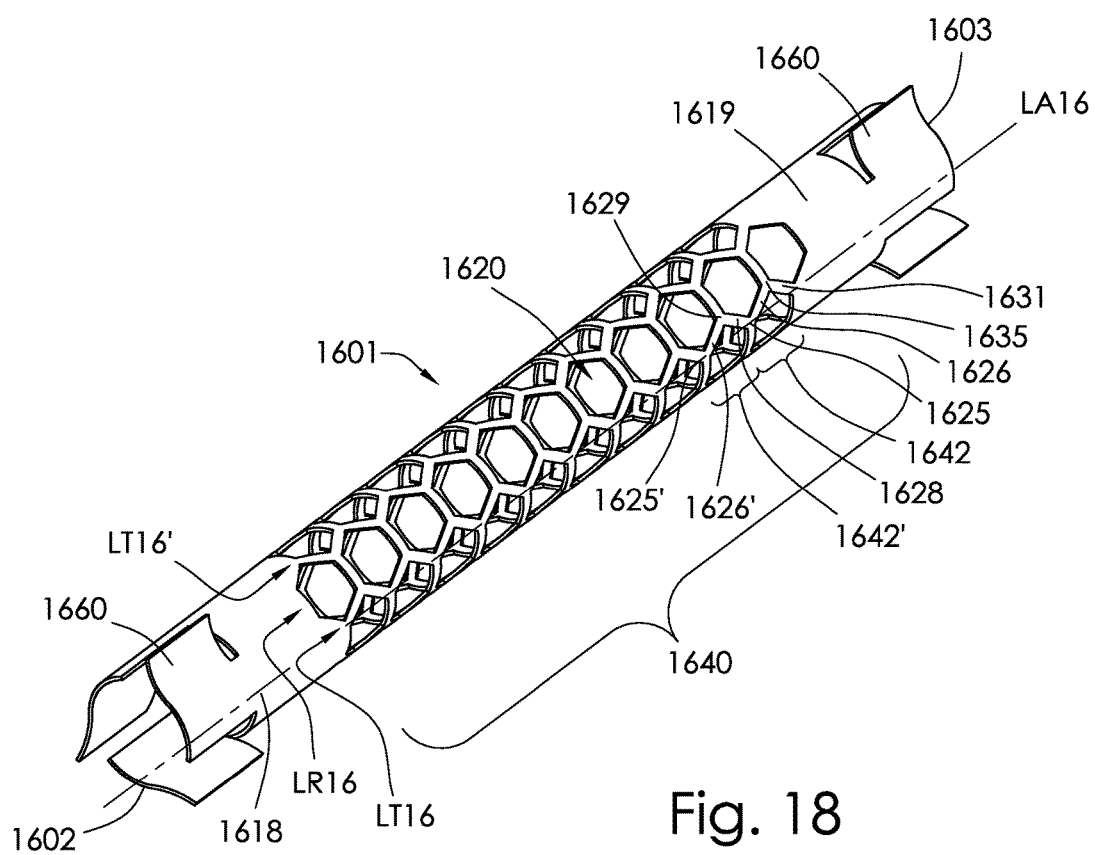
FIG. 18 is a profile perspective view of a fifteenth embodiment showing a single piece construct wherein fastener has an open accordion portion in its shortened austenite state. The accordion structure is made up of a plurality of longitudinally aligned rows of hexagonal openings cut transversely through the wall of a tubular fastener body and beset side by side but also slightly staggered or offset to any adjacent row of hexagonal openings to form a tessellation pattern.

FIG. 18 shows a fifteenth embodiment of a fastener 1601 wherein the fastener is again a cylindrical tubular structure, has a terminal 1602 and a terminal end 1603, and has a sleeve 1618 and a sleeve 1619 extending substantially inward from the terminal ends. Within sleeves 1618 and 1619 are a plurality of anchoring means or barbs 1660 similar to barbs 1060 as described previously in the embodiments of FIGS. 13A and 13B. Substantially further inward along fastener 1601 from terminal ends 1602 and 1603, and set between sleeves 1618 and 1619, is an open accordion-like structure 1640 shown here in its shortened austenite phase. Herein, the wall of the fastener has a plurality of openings or apertures 1620 defined therein and being cut full thickness through the wall of the fastener. Although the structural details of the accordion section and the anchoring members differ, the fifteenth embodiment has the same functional features as described for the first embodiment and as shown best in FIG. 2C.

As shown in FIG. 18, apertures 1620 are hexagonal in the extended state instead of the extended oval shape as shown in FIGS. 13A and 13D, or the extended round shape as shown in FIG. 17A and FIG. 17B. However, apertures 1620 take on a different shape in the martensite phase. As the fastener is elongated by deformation and changed to its martensite phase, the hexagonal shape of the apertures will also deform and take on a more rectangular shape. Herein, the rectangular shape may or may not be a perfect rectangle as the long sides of the rectangle may or may not have a curved or bowed shape to them when the hexagon is stretched out. In other words, the angles formed by the joining of zig and zag segments are more obtuse in the martensite phase and could be 0 degrees, making the longitudinally extending sides of the rectangle generally straight, or more obtuse at say 170 degrees, making the long wall of the rectangle to have a slightly angled or bowed shape. This shape will then be maintained as long as the fastener remains in martensite phase, the apertures returning to a hexagon shape upon implantation into the body, and heat acting as a catalyst returns the fastener to its austenite phase. A first spirally arcing leg-like zig segment 1626, as shown in FIG. 18, arcs spirally inward relative to a longitudinal axis LA16 of the tubular fastener body, and a first arcing zag like segment 1628 arcs outward relative to longitudinal axis LA16. These two segments are joined by a transversely oriented inner bendable connector 1625 to form a zigzag element 1642. Each zigzag element 1642, as formed by zig segment 1626 joined to a zag segment 1628 by a transversely oriented inner bendable connector 1625, is joined to an adjacent zigzag element 1642' by a transversely oriented outer bendable interconnector 1629 between each of the zigzag elements, interconnector 1629 being shown joined to the adjacent element 1642' via its zig segment 1626'. Thus, bendable connectors 1625 and bendable interconnectors 1629 face in opposite directions relative to the longitudinal axis LA16 and are fixedly connected to the segments joined thereby. Zigzag element 1642 is joined to sleeve 1619 as a final zigzag element via an outer interconnector 1635 and a zag segment 1631, this arrangement being repeated to connect sleeve 1618 to the accordion section at the opposite end thereof. Alternatively, the zigzag structure 1640 can be considered as a series of alternating zig and zag segments joined by a series of alternating outward and inward transversely oriented bendable connectors. As further alternatives, each zigzag element can be considered as formed by two arcing leg-like segments joined to form a bendable connection, wherein the shapes of the zig segments and the zag segments and the transversely oriented bendable interconnectors and connectors fixedly attached there between, form hexagonal apertures 1620. Most any shape opening could be used to form the accordion structure inclusive of but not limited to square, triangular, octagonal, or diamond.

Furthermore, a longitudinal tier LT16 is formed by a series of contiguously connected zigzag elements 1642, 1642' each longitudinal tier LT16 spanning the length of the accordion section and fixedly attached at either end to sleeve 1618 and 1619 by either a zig segment or a zag segment. Each single longitudinal tier LT16 is fixedly attached to an adjacent longitudinal tear LT16', such that a series of these longitudinal tiers are connected circumferentially around the tubular fastener body to form the accordion section 1640. A zigzag element 1642 of one longitudinal tear LT16 is joined by its transversely oriented outer bendable interconnector 1629 back-to-back to the bendable connector of an adjacent zigzag element from an adjacent longitudinal tier, such that the zigzag elements of any longitudinal tier is out of sync, out of phase, or reversed in polarity to the zigzag element joined to thereby on the adjacent longitudinal tier. The arcing zig segments contiguously connected to the arcing zag segments at the bendable connectors, and the bendable interconnectors and the connections of the zigzag elements of one longitudinal tier to the zigzag elements of an adjacent longitudinal tier, form the apertures 1620 thereby form the tessellated pattern of the accordion section. In other words, any single longitudinal row LR16 is offset from any adjacent longitudinal row such that a circumferential transverse line drawn through the center of any aperture 1620 around the tubular fastener body will not pass through a similar circumferential transverse line drawn through the center of any aperture 1620 from an immediately adjacent longitudinal row passing around the fastener body.

As described in prior embodiments, zig segments connected to zag segments by inner bendable connectors and zigzag elements connected to adjacent zigzag elements by outer bendable interconnectors are joined at angles such that during austenitic transformation those angles become more acute (smaller) in the austenite phase to shorten the length of the elongated tubular fastener body. This type of shortening is illustrated best in FIGS. 19B and C showing such a transformation of the sixteenth embodiment as described below.

Sixteenth Embodiment

FIGS. 19A and 19B show a sixteenth embodiment of a fastener wherein the fastener 1701 is again a cylindrical tubular structure, has a terminal end 1702 and a terminal end 1703, and has a sleeve 1718 and a sleeve 1719 extending substantially inward from the terminal ends. As seen best in FIG. 19A, set substantially further inward along fastener 1701 from terminal ends 1702 and 1703, and set between sleeves 1718 and 1719 is an open accordion section 1740. For further clarification, the fastener as shown in FIGS. 19B and 19C is the austenitic fastener, this being the fastener that is manufactured and wherein the barbs are flared outward and the accordion section is in its contracted state, the state it turns to once implanted into the body. Herein the accordion section as described later has folds which, when manufactured, are flared, buckled or expanded outward radially away from a central longitudinal axis which is different than the folds of the accordion sections of the embodiments in FIGS. 13-18. In FIGS. 19B and 19C, the apertures 1720 are more rectangular due to the contraction of the accordion, and when the fastener is deformed out to the elongated martensite phase of FIG. 19A, the apertures take on a more square shape and the barbs are folded flush with the wall of the fastener. FIG. 19A shows the fastener in its martensitic phase with the open accordion-like section 1740 extended by deformation and a plurality of anchoring means or barbs 1760 and 1760' lying substantially flush by deformation to the surface of the fastener. Barbs 1760 and 1760' are similar to barbs 1060 and 1060' as described previously in the embodiments of FIGS. 13A and 13B and are beset within sleeves 1718 and 1719. Herein, the wall of the fastener has a plurality of rectangular-shaped apertures 1720 defined therein and being cut full thickness through the wall of the fastener. Although the structural details of the accordion section and the anchoring members differ, the sixteenth embodiment has the same functional features as described for the first embodiment and as shown best in FIG. 2C.

As shown in FIG. 19A, apertures 1720 are rectangular instead of the oval, circular, or hexagonal shape as shown in prior embodiments. Apertures 1720 are arranged in a longitudinal row LR17 and a plurality of longitudinal rows are set side by side in parallel fashion around the circumference of fastener 1701. The adjacent longitudinal rows are not staggered or offset from each other as they are in some of the prior embodiments. In other words, the longitudinal rows are aligned with each other such that a circumferential transverse line drawn through the center of any aperture 1720 around the tubular fastener body will pass through a similar circumferential transverse line drawn through the center of any aperture 1720 from an immediately adjacent longitudinal row passing around the fastener body As shown in FIG. 19B and detailed in FIG. 19C the contractible accordion section 1740 in its austenite phase is made up of a plurality of folds or pleats 1735, again both terms being interchangeable. These folds are created by a series of contiguously connected zigzag elements 1742, 1742'. In this embodiment, a first leg-like zig segment 1726 extends radially inward relative to a longitudinal axis LA17 and a first leg-like zag segment 1728 extends radially outward relative to the longitudinal axis LA17, and these two segments are joined at an acute angle M by an inner bendable connector or juncture 1725 to form the first one of the zigzag elements 1742. Each zigzag element 1742, as formed by zig segment 1726 joined to zag segment 1728 by inner bendable connector 1725, is joined at an acute angle M' to a second zig segment 1726' of an adjacent zigzag element 1742' by an outer bendable interconnector 1729 to form the series of contiguously connected zigzag elements 1742, 1742'. Thus, bendable connector 1725 and interconnector 1729 are angle connectors that face in opposite directions and are fixedly interconnected to the segments joined thereby. Also, each bendable connection joining any zig and zag segments forms either an acute angle M or an acute angle M', angles M and M' preferably being equal. An end leg-like zag segment 1731 extends radially outward to join the sleeve 1719 to the final zigzag element 1742 of the accordion section 1740.

Alternatively, the zigzag structure of the accordion section 1740 can be considered as a series of alternating zig and zag segments joined by a series of alternating outward and inward bendable connections. As further alternatives, each zigzag element can be considered as formed by two leg-like segments joined to form a bendable connection.

The acuteness (sharpness) of angles M and M' can increase to provide a smaller acute angle when the accordion like portion of the fastener transitions from the martensite phase to the austenite phase upon a change in temperature, or the acuteness of angles M and M' can decrease to provide a larger acute angle when deformed from the austenite to the martensite phase. In other words, each foldable portion 1725, 1725' of the tubular wall between adjacent aperatures 1720 in different rows need not be completely flat wherein M and M' are at 180° as illustrated by the martensitic tubular body 1710 in FIG. 19A, but instead may have greater obtuseness than that shown in FIG. 19C. The plurality of zigzag elements 1742, 1742' therefore creates the plurality of folds seen in the contracted accordion-like section of the fastener as shown in FIGS. 19B and 19C. The total number of folds can vary from one or two to hundreds or more depending on the demands required of the fastener and is not limited to what is shown in the drawings. The sharper (more acute) angles M and M' become the greater the amount of contracture or shortening of the accordion portion of the fastener.

A longitudinal tier LT17 is formed by a series of contiguously connected zigzag elements 1742, 1742', each longitudinal tier LT17 spanning the length of the accordion section and fixedly attached at either of its ends to sleeves 1718 and 1719 by either a zig segment or a zag segment.

Any one inner bendable connector 1725 of a zigzag element within any one longitudinal tier LT17 is fixedly joined to the inner bendable connector of a zigzag element within an adjacent longitudinal tier LT17' by a transversely arcing bar 1786. Thus, a plurality of transversely arcing bars 1786, 1786' joins the longitudinal tiers together and these bars, along with the zigzag elements joined thereby, form the generally rectangular shape of apertures 1720, as seen in FIG. 19A, in the martensite phase of the fastener 1701. In the austenite phase of FIG. 19B, the aperatures 1720' are also essentially rectangular.

Alternatively, the accordion section 1740 may be considered as formed by a series of longitudinal tiers LT17, LT17' around the circumference of the tubular fastener body 1710 wherein the longitudinal tiers are joined by the transversely arcing bars 1786 at the inner bendable connectors 1725 of the zigzag elements.

Compared to the ninth through fifteenth embodiments, wherein the change in the accordion structure occurs axially and circumferentially and wherein the accordion portion remains in plane with the wall of the fastener, the pleats or folds 1735 of the accordion structure of the sixteenth embodiment is formed by the zigzag elements being expanded or buckled radially outward, as seen in FIG. 19B and detailed in FIG. 19C. The expanding or buckling is away from a long axis LA17 of the fastener in a corrugated fashion similar to a more traditional bellows structure to cause shortening of the fastener, thus drawing closer together terminal ends 1702 and 1703 during the phase change from martensite to austenite. As in other embodiments as well, anchoring means or barbs 1760, 1760', as best seen in FIG. 19B, expand outward from the wall of the fastener during the martensite to austenite phase change. The zigzag segmentation of the sixteenth embodiment is shown best in FIG. 19C. Herein the fastener 1701 and open accordion section 1740 are in the austenite phase wherein the longitudinal tiers LT17 and LT 17' have changed from an essentially flat longitudinally surface to a zigzag corrugated fold-like wall structure. This martensite to austenite phase change has caused the bendable interconnector 1729 to buckle or bend radially outward away from the longitudinal axis LA17 of the fastener. There is less tendency for any bending of the inner connectors 1725 because they are reinforced by the transverse bars 1786.

Any plurality of longitudinal tiers LT17 as needed for the application required of the fastener can be built into the accordion section. This embodiment shows four but as few as one or as many as eight or more could conceivably exist per tier. Furthermore, any plurality of zigzag elements 1742 can be formed along the length of the longitudinal tier as needed for the application of the fastener, with as little as one zigzag element, to possibly hundreds or thousands of zigzag elements.

Operation of the Tenth Through Sixteenth Embodiments

Fasteners 1101 through 1701 are used in the same manner as fastener 1001 as shown in FIGS. 13A and 13B and described earlier under the ninth embodiment.

Seventeenth Embodiment

FIG. 20 shows a seventeenth embodiment of a fastener 1801 in its austenite phase, the fastener being comprised of segments that form a longitudinally extending fold-like contractible wall structure 1840, hereinafter called accordion section 1840. The contractible accordion section 1840 is made up of a plurality of folds, pleats, or zigzag elements 1842, 1842', these terms being interchangeable. Zigzag elements 1842, 1842' are contiguously connected together in series along the length of the accordion section by bendable interconnectors 1829. This fold-like wall structure of the accordion section subsequently forms and can alternatively be considered a longitudinal tier LT18 of contiguously interconnected zigzag elements 1842, 1842'. Although the structural details of the accordion section and the anchoring members differ, the seventeenth embodiment has the same functional features as described for the first embodiment and as shown best in FIG. 2C.

In this embodiment, a first leg-like zig segment 1828 extends inward relative to a non-central longitudinal axis LA18 of the fastener and a first leg-like a zag segment 1826 extends outward relative to the longitudinal axis LA18 and these two segments are joined at an acute angle J' by an inner bendable connector 1825 relative to longitudinal axis LA18 to form a first one of the zigzag elements 1842. Each zigzag element 1842, as formed by a zig segment 1828 joined to a zag segment 1826 by inner bendable connector 1825, is joined at an angle J to a second zag segment 1826' of an adjacent zigzag element 1842' by an outer bendable interconnector 1829 to form the series of contiguously connected zigzag elements 1842, 1842'. Thus bendable connectors 1825 and interconnectors 1829 are angled connectors that face in opposite directions and are fixedly interconnected to the segments joined thereby. Also, each bendable connection joining any zig and zag segments forms either an acute angle J or an acute angle J', angles J and J' preferably being equal.

An end interconnector 1831 and end leg-like zig segment 1832 of the final fold element 1842" has an anchoring member 1864' with outthrust prongs 1853 and 1852 extending axially relative to long axis LA18, outthrust prongs 1853 and 1852 being fixedly joined to the accordion section 1840 by a final inner bendable connector 1825' of a final zigzag element 1842" having a zig segment 1832 joined to a zag segment 1824 by the connector 1825'. Alternatively, outthrust prong 1853 is fixedly joined to the final zag segment 1824 at the final inner bendable connector 1825' of the according section. Furthermore, the second outthrust prong 1852 extends substantially outward axially, again in relation to longitudinal axis LA18, from the final zag segment 1824 in parallel to the first outthrust prong 1853, both being fixedly attached to the final zag segment at bendable connector 1825'. This anchoring means is repeated by the anchoring member 1864 at the opposite side of the fastener wherein, in this embodiment, a pair of outthrust prongs 1850 and 1851 extend axially from an end zig segment 1823 of the accordion section. The outthrust prongs 1850 and 1851 have terminal ends 1802 and 1804, respectively, whereas at the opposite end of the fastener, the ends of the outthrust prongs 1853 and 1852 have terminal ends 1803 and 1805 respectively. Furthermore, protruding perpendicularly and radially away from each prong relative to long axis LA18 are quills 1854 and 1857 that serve to anchor the fastener into surrounding substrate. Quills 1857 and 1854 are triangular when viewed in profile but extend the width of the prongs 1850 and 1851.

An elongatedly transverse apex 1853 spans the width of the quill 1854 from an outermost corner 1855 to a widthwise opposite outermost corner 1855', an apex 1853 is beset substantially axially inward on outthrust prong 1851 away from its terminal end 1804. A face 1856 slopes from apex 1853 radially outward from the long axis LA18 in the direction opposite terminal end 1804. A parabolic meniscus 1861 ellipses inward from prong terminal ends 1802 and 1804 along an underside or internal surface 1858 of the prongs. The prongs join the accordion section 1840 at a first bendable connector 1825" of a zig segment 1823.

The acuteness (sharpness) of angles J and J' can increase to provide a smaller acute angle when the accordion like portion of the fastener transitions from the martensite phase to the austenite phase upon a change in temperature, or the acuteness of angles J and J' can decrease to provide a larger acute angle when deformed from the austenite to the martensite phase. The plurality of zigzag elements therefore creates the plurality of folds seen in the accordion-like section of the fastener. The total number of folds can vary from one or two to hundreds or more depending on the demands required of the fastener and is not limited to what is shown in the drawings. The less (smaller) acute angles J and J' become, the greater the amount of contracture or shortening of the accordion section of the fastener.

A longitudinal central cannulation 1860 passes through the length of the accordion section from the first zig segment 1823 through the last zag segment 1824, cannulation 1860 again used for passage of a guide wire as previously described. Cannulation 1860 therefore passes through each zig segment and each zag segment of the accordion section whether there is one zigzag element or hundreds. Cannulation 1860 lies parallel to longitudinal axis LA18 of the fastener body and each cannulation through each zig and each zag segment is axially aligned.

Operation of the Seventeenth Embodiment

Fastener 1801 of FIG. 20 is utilized in a similar manner as previously described in other embodiments. The surgical procedure and implantation are also the same as previously described and a broach matching the shape of the fastener is used to fashion holes in the proximal and middle phalanx after placing the guide wires. After placing the austenite fastener across the interphalangeal joint, heat acting as a catalyst cause the fastener to contract and shorten. Angles J and J', less acute (larger) in the martensite phase, are decreased to a more acute (smaller) angle in the austenite phase as the accordion section contracts. This angular change of J, J' across the zigzag elements draws the anchoring members 1864 and 1864' closer together, compressing the proximal and middle phalanx together.

Eighteenth Embodiment

FIG. 21 shows an eighteenth embodiment of a fastener 1901 with an open accordion section 1940 in the austenite phase, wherein the overall shape of the fastener is not cylindrical or rectangular but instead longitudinally octagonal. It could also be of other shapes such as hexagonal, square, rectangular, diamond, fusiform, or any other such geometrical shape. Running longitudinally down the center of fastener is a central cannulation 1960 as in prior embodiments and parallels a long axis LA19 of the fastener. Each of the embodiments disclosed herein has a labeled cannulation with a central longitudinal axis that provides an axis of symmetry. This central axis is labeled only for some embodiments, such as for example A1 in FIG. 6A, C1 in FIG. 7A, C' in FIGS. 15A and C" in FIG. 21. Furthermore, these central longitudinal axes differ from the series of LA long axes that are constructs used in this disclosure to define the relative directions of the zig segments versus the zag segments of the zigzag elements.

A sleeve 1919 extends inward along the fastener from a terminal end 1903. Beset centrally within fastener 1901 is an open accordion section 1940 comprised of a plurality of transversely oriented diamond shaped openings or apertures 1920 arranged in longitudinal rows and extending through the width of the fastener body. The shape of the apertures do not need to be diamond shaped as shown but instead could be of any number of possible geometries, such as circular, octagonal, hexagonal, rectangle or any other that allows the fastener 1901 to shorten, change length, or change shape during a phase change. Although the structural details of the accordion section and the anchoring members differ, the eighteenth embodiment has the same functional features as described for the first embodiment and as shown best in FIG. 2C.

Apertures 1920 in this embodiment are not arranged around the perimeter of the fastener but instead are full thickness through the fastener from a lateral side plane P1 to an opposite lateral side plane P2 (not seen), planes P 1 and P 2 forming the lateral outer surfaces of sleeves 1919 and 1918 and extending the length of the fastener. A fold-like wall structure or longitudinal first tier W1, wall structure and longitudinal tier being synonymous, extends the length of the accordion section 1840. Wall structure W1 is like the accordion section 1840 of fastener 1801 in FIG. 20 except there is no central cannulation. As in the accordion section 1840 of fastener 1801, the wall structure W1 of the accordion section 1940 in the eighteenth embodiment is formed by a series of contiguously connected zigzag elements 1942, 1942'. The whole of the accordion section 1940 is formed from a series of stacked layers of more than one accordion section like accordion section 1840 from the seventeenth embodiment in FIG. 20, such that the arrangement of stacked wall structures, each like accordion section 1940, gives the appearance of an accordion style elevator gate. As seen in the accordion section 1940 in FIG. 21, the first longitudinal tier or wall structure W1 is stacked on a second tier or wall structure W2, the second wall structure W2 being stacked on a third tier or wall structure W3. The third wall structure W3 is stacked on a fourth tier or wall structure W4. Each wall structure is fixedly and bendably joined to any one wall structure above or below it. As few as one fold-like wall structures as represented in FIG. 20 or as few as two or three wall structures as represented by walls W1 and W2 and W3 in FIG. 21, to potentially tens or hundreds of stacked wall structures, could be used in the accordion section depending on the application or needs of the fastener, and therefore the embodiment is not restricted to four stacked walls.

For further conciseness, as seen in FIG. 21, the first wall structure W1 makes up a first stacked layer of accordion portion 1940. The wall is a longitudinally extending folded or zigzag structure which is best exemplified in FIG. 20 as accordion portion 1840. Accordion section 1940, as seen in FIG. 21, consists of the first wall W1 stacked on top of a second wall W2 and second wall W2 is reversed in polarity to that of the first wall W1. In other words, the zigzag segments 1942, 1942' of wall W1 are not in phase or in sync with the zigzag segments 1942, 1942' of wall W-2. Furthermore, a first leg-like zig segment 1926 extends inward relative to a long axis LA 19 of the fastener and a first leg-like zag segment 1928 extends outward relative to a longitudinal axis LA19 and zig segment 1926 and zag segment 1928 are joined by a bendable connector 1925 of wall structure W1 to form a first zigzag element 1942. Contiguously connected zigzag elements 1942, 1942' form the first wall W1 of the accordion section 1940, zag segment 1928 being joined by a bendable interconnector 1929 to a second zig segment 1926' of second zigzag element 1942'. A third leg-like zig segment 1933 of the second wall W2 extends inward relative to long axis LA19 and a third leg-like zag segment 1931 of the second wall W2 extends outward relative to the longitudinal axis LA19, these two segments being joined by an inner bendable connector 1927 of a third zigzag element 1942L of the second wall W2. Element 1942L is attached to sleeve 1919 by an outer bendable interconnector 1937 joined to zag segment 1931. This second wall of contiguously connected zigzag elements is thus fixedly attached to the first wall of zigzag elements at the inner bendable connectors relative to longitudinal axis LA19, each wall being out of phase or inverted to the wall that is stacked on top of it.

The second wall W2 is stacked on top of the third wall W3. Hereinagain, wall W3 is reversed in polarity, out of sync, or inverted to wall W2 but polarized or in sync with the first wall W1. Furthermore the zigzag elements 1942 of wall W3 are not in sync with the zigzag elements of wall W2. However, the zigzag elements of wall W3 are in sync with those of the zigzag elements of wall W1. The bendable connectors of wall W3 that are polarized or in sync with wall W1 are fixedly attached to the bendable connectors of wall W2 that are out of sync or out of phase with the bendable connectors of wall W1. The fourth wall W4 in this embodiment is connected to wall W3 in a similar manner.

A final zigzag element 1942" of wall W1 is fixedly attached to sleeve 1919 at the end of the sleeve opposite terminal end 1903 by a final bendable interconnector 1952, element 1942" having a zag segment 1932 and a zig segment 1923 joined by an inner bendable connector 1935. The final zag segment 1931 of wall W-2 is fixedly attached to the sleeve 1919 at a final bendable interconnector 1937. The same arrangement also forms the connections of the final zig and zag segments of wall W3 and wall W4 to sleeve 1919 and the final zig and zag segments of walls W1, W2, W3 and W4 to sleeve 1918 at the opposite end of the fastener. Each zigzag element is joined to an adjacent zigzag element at an acute angle L by a bendable interconnector and each zig segment is joined to an adjacent zag segment by a bendable connector at an acute angle L'. Angles L and L' are preferably equal. Furthermore, due to the out of phase stacked walls, any zig segment of one wall is joined to a zig segment of the wall beneath it at an inner bendable connector at an angle K. Thus, inner bendable connectors join a zig segment of one wall to a zig segment of an adjacent wall and are fixedly interconnected to the segments joined there by at angle K.

FIG. 21 shows the shortened austenite phase of the fastener. Angles L and L' in the martensite phase will be less acute (larger), possibly even obtuse, this angle becoming more acute (smaller) as the accordion section changes through austenitic transformation to the austenite phase and the accordion section contracts and shortens along its length. In contrast, angle K is generally obtuse in the austenite phase, as shown in FIG. 21 and less obtuse or maybe acute in the martensite phase depending on how much the accordion section is elongated by deformation. Thus, in the transition of the accordion sections from the martensite phase to the austenite phase, angles L and L' become more acute and angle K becomes less acute.

Beset within sleeve 1919 is a first anchoring means in the form of upper and lower barbs 1970 that serve again to anchor fastener 1901 into its surrounding substrate. In forming barbs 1970, sleeve 1919 has a generally L-shaped or lazy L-shaped cut 1971 extending from an oblique lateral side plane P3 which runs the length of the octagonal fastener body to an opposite oblique lateral side plane P4 (not seen). A short arm 1972 of the L-shaped cut 1971 extends from the superior side plane P5 depthward towards and perpendicular to the central axis C" of the cannulation 1960 into adjacent oblique lateral side planes P3 and P4 of the octagonal fastener towards the opposing inferior side plane P6 (not seen) on the underside of the fastener. A long arm 1973 of the L-shaped cut 1971 then extends longitudinally parallel to the central axis C" of the fastener 1901 substantially towards terminal end 1903. L-shaped cut 1971 is full thickness through oblique lateral side plane P3 to the opposite oblique lateral side plane P4, and does not extend far enough longitudinally to reach terminal end 1903. As seen in FIG. 21, the barbs are in their austenite phase, expanded outward in the necessary position to anchor the fastener into its substrate.

Opposite terminal end 1903, a sleeve 1918 is fixedly attached to accordion portion 1940 by a zig segment or a zag segment of each wall W1-W4 as previously described for the zig and zag segments on the opposite end of the accordion section 1940 at sleeve 1919, longitudinally extending in near axial alignment to central axis C" of cannulation 1960 in a substantially opposite direction from accordion section 1940. An anchoring member 1964 comprised of a pair of out-thrust prongs 1950, 1951 extends from sleeve 1918, each prong ending at a terminal end 1902 or 1904, respectively. More prongs could be added as needed for the application and therefore not limited to just a pair. Terminal ends 1902 and 1904 exist at the end of each prong and are beset substantially farthest away from the accordion structure and sleeve 1918. The lateral oblique side plane P3 forms one-eighth of the sides of the prongs and fastener. Four of these lateral oblique side planes exist per fastener, one extending along both sides of each prong and the accordion section, all the way between the terminal ends 1903 and 1902. The superior side plane P5 makes up another surface along the out-thrust prongs and length of the fastener. Extending outward from prongs 1950 and 1951 from superior side plane P5 and substantially perpendicular to the side plane adjacent to each of the terminal ends 1902 and 1904, is a pair of quills 1954 and 1954', respectively, that serve to anchor fastener 1901 into the surrounding substrate. Any plurality of quills is acceptable. Herein the quills 1954 and 1954' are triangular in shape when viewed in profile.

An elongatedly transverse apex 1953 spans quill 1952 from an outermost corner 1955 to a widthwise opposite outermost corner 1955'. A face 1956 slopes from apex 1953 baseward towards the quill's origin off of its corresponding prong in the direction of it corresponding terminal end. A parabolic meniscus 1959 ellipses inward from prong terminal ends 1902 and 1904 along an underside or internal surface 1958 of the prongs. Meniscus 1959 joins the underside 1958 of each prong. Cannulation 1960 passes through fastener 1901 traveling from terminal end 1903, through the accordion section 1940 and through sleeve 1918, where its path ends at meniscus 1959.

Operation of the Eighteenth Embodiment

The operation of the eighteenth embodiment is again similar to previously described embodiments. If being used for a hammertoe correction or other joint fusion procedure, the joint surfaces are again prepared as demonstrated in FIGS. 5A and 5B and as described in the first embodiment. The guide wire 43 is then inserted into the abutment surface 78 of proximal phalanx 42 and down the center of proximal phalanx 42. Herein an octagonal broach would be used over the guide wire to ream out some of the bone in the proximal phalanx to match the octagonal shape of fastener 1901. Inclusive of the octagonal shape a broach would also be used to make allowance for prongs 1950 and 1951 such that a pathway is cleared through the intramedullary canal of the proximal phalanx to accommodate the prongs. The guide wire is then removed from the proximal phalanx and driven down the middle phalanx. An octagonal broach is used to remove bone from the middle phalanx 46. Thereafter, the martensitic fastener 1901 is inserted prong and quill end first into proximal phalanx 42. Herein the prongs 1950 and 1951 may be fabricated to function in one of two ways, either through the superelastic properties or the shape memory properties of the material from which the fastener is made. With the former, the prongs are simply clamped or pinched toward one another prior to insertion in the proximal phalanx. Once the terminal ends 1902, 1904 are placed into the medullary canal of the proximal phalanx, the clamping force is released allowing the superelastic prongs to spring outward to their resting position. This imparts the quills into the surrounding bone or substrate, anchoring the fastener into the proximal phalanx. With the latter, the prongs are shape set outward away from each other in the austenite phase. When cooled in the austenite phase, the prongs are deformed inward toward the longitudinal axis and stay this way after the deforming force is removed. They therefore do not require a mechanical clamping or pinching force prior to insertion. Upon insertion into the proximal phalanx, as the fastener warms to body temperature, the prongs will deploy outward impacting the barbs into the surrounding bone or substrate effectively anchoring the fastener.

For further clarification prongs 1950 and 1951 and quills 1954 and 1954' are merely representative of an alternative anchoring mechanism to previously described barbs and anchoring methods. The prong could be fabricated to utilize the shape memory properties of nitinol as the accordion portion does, or it could utilize the superelastic properties of nitinol. If the shape memory properties were being utilized, prongs 1950 and 1951 in the austenite phase, as shown in FIG. 21, would be expanded outward away from the longitudinal axis of cannulation 1960. In the martensite phase, prongs 1950 and 1951 would be, by deformation, bent towards each other and cannulation 1960. Upon phase change back to austenite prongs 1950 and 1951 would expand outward. If utilizing the superelastic properties of nitinol for prongs 1950 and 1951, the prongs would maintain their shape as shown in FIG. 21, but upon implantation, instrumentation could be used to compress the prongs together while the fastener is inserted. Once implanted and the instrumentation remove, prongs would spring outward to provide constant outward pressure against bone or substrate once implanted.

The remainder of the operation is the same as for the first embodiment. The tip 98 of guide wire 43, sitting just proud of abutment surface 74, is then placed into cannulation 1960. The martensitic fastener is then imparted into middle phalanx 46 along the broached medullary canal as the guide wire 43 passes down central cannulation 1960. The abutment surfaces 74 and 78 of middle phalanx 46 and proximal phalanx 42 are then manually approximated such that they are contacting each other and held in this position while fastener 1901 warms and goes through its martensite to austenite phase change. In so doing, barbs 1970 deploy outward and anchor fastener 1901 into the surrounding substrate, in this case the middle phalanx, and as the prongs 1950 and 1951 also have been shape set, they too deploy outward and the quills 1954 and 1954' anchor into the bone.

As this occurs, the open accordion-like section 1940 goes through its phase change as well, shortening fastener 1901 and further compressing together the abutment surfaces of the middle and proximal phalanx as is done with previous embodiments. In so doing, angle K of the accordion section changes from its more acute (smaller) angle of the martensite phase to the less (larger) acute angle of the austenite phase during martensitic transformation as the zigzag segments making up fold-like wall structures change shape. Furthermore, angles L and L' changes from the less (larger) acute angles of the martensite phase to the more acute (smaller) angles of the austenite phase during martensitic transformation.

Nineteenth Embodiment

Figure 22:
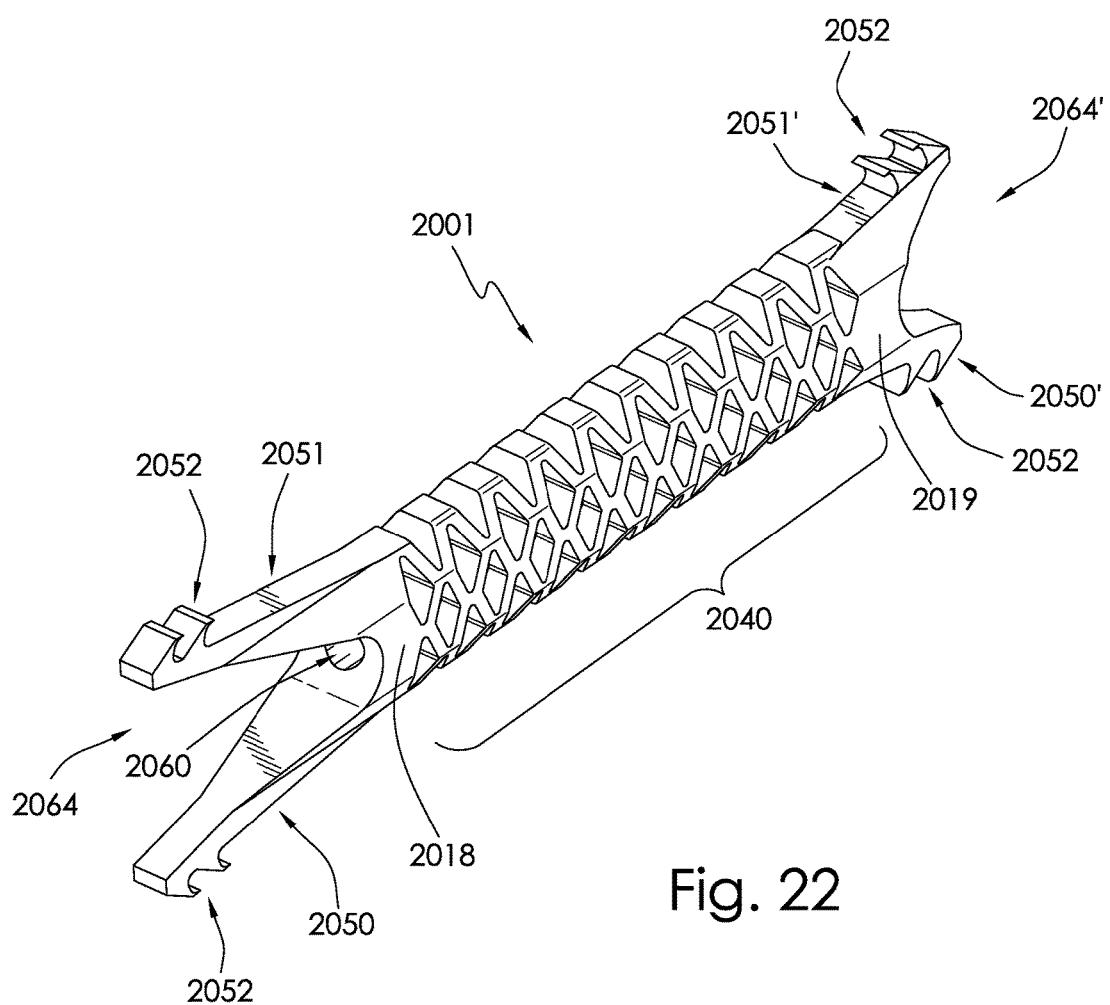
FIG. 22 is a profile perspective view of a nineteenth embodiment in its austenite phase and is similar to that of FIG. 21 but showing two further alternative anchoring means wherein the anchoring means at both ends of the embodiment are similar in shape and function to each other.

FIG. 22 shows a nineteenth embodiment wherein a fastener 2001, shown in the austenite phase, is similar to the eighteenth embodiment of FIG. 21 but shows a modification of the anchoring means at one end of the fastener. Beset centrally within fastener 2001 lies an open accordion-like section 2040 that has the same structure as accordion-like section 1940. Fastener 2001 again has a central longitudinal cannulation 2060 passing along the long axis of the fastener. There is again a sleeve 2018 and a sleeve 2019 as an extension fixedly attached on each end of the accordion section 2040. Similar to the previous embodiment of FIG. 21, anchoring members 2064 and 2064' have a first pair of prongs 2050, 2051 and a second pair of prongs 2050',2051' respectively, the prongs 2050 and 2051 being thrust axially outward from sleeve 2018 and the prongs 2050' and 2051', at the opposite end of the fastener, being thrust axially outward from sleeve 2019. Each prong at both ends of the fastener again has a pair of quills 2052, 2052. Each quill extends outward and away from a central axis of the cannulation 2060 of the fastener. The quills again serve to anchor the fastener into the surrounding substrate as in the previous embodiment. Herein the prongs are preferably similar in shape to the prongs 1950 and 1951 of the eighteenth embodiment shown in FIG. 21, but the prongs of the nineteenth embodiment are generally shorter or smaller to fit the smaller anatomy of the middle phalanx of the toe. The function and operation of the fastener 2001 is again similar to the eighteenth embodiment shown in FIG. 21.

What is claimed is:

1. A shape changing fastener for joining together two separate pieces, each having an internal bore extending axially inward from a contact surface, said fastener comprising:
    an elongated accordion section comprising at least one zigzag element;
    a first anchoring section connected to a first end of said accordion section and comprising a first anchoring means for fixedly engaging the internal bore of one of said pieces; and,
    a second anchoring section connected to a second end of said accordion section and comprising a second anchoring means for fixedly engaging the internal bore of the other of said pieces;
    each of said anchoring means comprising at least one prong element made of a material that changes shape when activated by a catalyst such that said prong element is capable of moving laterally from a contracted position out of fixed engagement with a wall of the bore to an extended position fixedly engaged with the bore wall;
    said elongated accordion section comprising a material that changes shape when activated by a catalyst such that said accordion section is capable of contracting axially from an extended state to a contracted state to move said first anchoring means toward said second anchoring means while each said anchoring mean is fixedly engaged with the bore wall of a respective one of the pieces, said accordion section in its contracted state extending laterally for less than the lateral extent of the internal bore such that the bore wall does not interfere with said axial contraction;
    and said zigzag element comprising at least one zig segment and at least one zag segment extending inwardly toward each other in opposing relation when said accordion section is in its contracted state, an inward portion of said zig segment being joined to an inward portion of said zag segment by a connector such that, during said axial contraction, said zig and zag segments converge toward said connector to form an angle that decreases to provide at least a portion of said axial contraction.

2. A shape changing fastener according to claim 1, wherein said accordion section comprises an elongated wall in which said zig segment and said zag segment form a fold of said wall when said accordion section is in its contracted state.

3. A shape changing fastener according to claim 2, wherein said elongated wall comprises a plurality of said zigzag elements, and wherein a zag segment of one of said elements is joined to an adjacent zig segment of another of said elements by an interconnector such that said elongated wall has multiple folds when said accordion section is in its contracted state.

4. A shape changing fastener according to claim 2, wherein said elongated wall comprises a plurality of said zigzag elements, and wherein a zag segment of one of said elements is integrally joined to an adjacent zig segment of another of said elements by an interconnector to form an elongated wall having multiple folds when said accordion section is in its contracted state and also when said accordion section is in its extended state.

5. A shape changing fastener according to claim 1, wherein said accordion section comprises a tubular body having at least one pair of opposing apertures passing transversely through a tubular wall, each of said apertures being formed by two zigzag elements in opposing relation.

6. A shape changing fastener according to claim 5, wherein said tubular body has a plurality of opposing aperture pairs, and wherein a zag segment of one of said zigzag elements is integrally joined to an adjacent zig segment of another of said zigzag elements by an interconnector to form a tubular body having multiple accordion-like folds when said accordion section is in its contracted state.

7. A shape changing fastener according to claim 1, wherein said accordion section has a fold-like wall element formed by said zig segment and said zag segment when said accordion section is in its contracted state.

8. A shape changing fastener according to claim 7, wherein said accordion section is elongated and comprises a plurality of said zigzag elements, and wherein a zag segment of one of said elements is integrally joined to an adjacent zig segment of another of said elements by an interconnector to form at least one zigzag wall extending longitudinally along said elongated accordion section and having multiple fold-like wall elements when said accordion section is in its contracted state.

9. A shape changing fastener according to claim 8, wherein said accordion section comprises at least two of said longitudinally extending zigzag walls arranged adjacent to each other to form two tiers of a stack, said two adjacent walls being inverted relative to each other to define a plurality of apertures passing transversely through said accordion section and arranged in a row extending longitudinally along said elongated accordion section.

10. A shape changing fastener according to claim 9, wherein said accordion section comprises at least four of said longitudinally extending zigzag walls arranged to form four tiers of a stack with said two inverted adjacent walls forming intermediate walls between a top wall and a bottom wall of said stack, one of said intermediate walls being adjacent and inverted relative to said top wall and the other of said intermediate walls being adjacent and inverted relative to said bottom wall to define a plurality of apertures passing transversely through said accordion section and arranged in three rows each extending longitudinally along said elongated accordion section.

11. A shape changing fastener according to claim 1, wherein the shape changing material is activated by a change in temperature, wherein said accordion section has a cool state corresponding to its extended state and a warm state corresponding to its contracted state, and wherein said section is shortened axially when heated from said cool state to said warm state.

12. A shape changing fastener according to claim 11, wherein each of said prong elements comprises one or more barbs made of said material that changes shape when activated by a change in temperature, and has a structure causing said one or more barbs to expand outwardly for engaging the bore in a respective one of the pieces when implanted therein and said shape changing material is heated to a warm state from a cool state.

13. A shape changing fastener according to claim 1, wherein said accordion section and each of said anchoring means has a central cannulation, said cannulation being sized and aligned so as to receive a guide wire for guiding a distal end of each of said anchoring means into a bore engaging position within a respective one of the pieces, and said accordion section and both of said anchoring means being arranged so that said guide wire may remain in place after the distal ends of said anchoring means are in their bore engaging positions.

14. A shape changing fastener according to claim 1, wherein each of said prong elements comprises one or more barbs made of a material that changes shape when activated by a catalyst, and has a structure causing said barbs to expand outwardly for engaging the bore in a respective one of the pieces when implanted therein and said shape changing material is activated by said catalyst.

15. A shape changing fastener according to claim 1, wherein:
    said accordion section extends along a longitudinal axis;
    and said at least one zig segment extends radially inward toward said longitudinal axis and said at least one zag segment extends radially outward from said axis when said accordion section is in its contracted state.

16. A shape changing fastener according to claim 1, wherein each of said prong elements comprises a structure capable of penetrating the bore wall to fix the anchoring means thereto during said axial contraction of the accordion section.

17. A shape changing fastener according to claim 1, wherein said shaping material is such that said movement provided by the axial contraction of said accordion section is capable of bringing into abutment and compressing together with spring biasing characteristics the contact surfaces of the respective pieces.

* * * * *